(12) United States Patent
Tomes et al.

(10) Patent No.: US 8,173,867 B2
(45) Date of Patent: May 8, 2012

(54) METHODS AND COMPOSITIONS FOR MODULATING FLOWERING AND MATURITY IN PLANTS

(75) Inventors: Dwight T. Tomes, Van Meter, IA (US); Silvio Salvi, Bologna (IT); Michele Morgante, Udiune (IT); Giorgio Sponza, Bologna (IT); Edward Bruggemann, West Des Moines, IA (US); Xiaomu Niu, Johnston, IA (US); Bailin Li, Hockessin (DE); Roberto Tuberosa, Bologna (IT)

(73) Assignee: Pioneer Hi Bred International Inc, Johnston, IA (US)

( * ) Notice: Subject to any disclaimer, the term of this patent is extended or adjusted under 35 U.S.C. 154(b) by 564 days.

(21) Appl. No.: 12/276,961

(22) Filed: Nov. 24, 2008

(65) Prior Publication Data
US 2009/0158467 A1  Jun. 18, 2009

Related U.S. Application Data

(63) Continuation of application No. 11/190,339, filed on Jul. 27, 2005, now Pat. No. 7,479,584.

(60) Provisional application No. 60/592,268, filed on Jul. 29, 2004.

(51) Int. Cl.
*C12N 15/82* (2006.01)
(52) U.S. Cl. .......................... 800/285; 800/278; 800/290
(58) Field of Classification Search .......................... None
See application file for complete search history.

(56) References Cited

U.S. PATENT DOCUMENTS

| | | | |
|---|---|---|---|
| 6,077,994 A | 6/2000 | Coupland |
| 6,140,085 A | 10/2000 | Dean |
| 6,265,637 B1 | 7/2001 | Coupland |
| 6,307,126 B1 | 10/2001 | Harberd |
| 6,573,430 B1 | 6/2003 | Bradley |
| 6,670,526 B1 | 12/2003 | Coupland |
| 6,762,348 B1 | 7/2004 | Harberd |
| 6,794,560 B2 | 9/2004 | Harberd et al. |
| 6,830,930 B2 | 12/2004 | Harberd |
| 6,887,708 B1 | 5/2005 | Coupland |
| 6,949,694 B2 | 9/2005 | Simpson |
| 7,045,682 B1 | 5/2006 | Dean et al. |
| 7,268,272 B2 | 9/2007 | Harberd |
| 2003/0101481 A1 | 5/2003 | Zhang et al. |
| 2004/0019927 A1 | 1/2004 | Sherman et al. |
| 2004/0045049 A1 | 3/2004 | Zhang et al. |
| 2004/0214272 A1 | 10/2004 | LaRosa et al. |
| 2005/0039227 A1 | 2/2005 | Harberd |
| 2005/0066394 A1 | 3/2005 | Danilevskaya |
| 2005/0071897 A1 | 3/2005 | Harberd |
| 2006/0053661 A1 | 3/2006 | Van Duyne |
| 2006/0059586 A1 | 3/2006 | Cheng et al. |

FOREIGN PATENT DOCUMENTS

| | | |
|---|---|---|
| EP | 1586652 A | 10/2005 |
| WO | WO02/33091 A | 4/2002 |

OTHER PUBLICATIONS

Colliver et al (1997, Plant Mol. Biol. 35:509-522).*
Montgomery et al (Trends in Genetics, Jul. 1998, 14(7):255-258).*
European Supplemental Search Report, EP 05 77 7342, Pioneer HI-Bred International, Inc. et al., PCT/US2005/026641, Mar. 10, 2009, 14 pages.
Database EMBL [online], XP-002518399, "OGLAX04TV ZM_0.7_1.5_KB *Zea mays* Genomic Clone ZMMBMa0312B08, Genomic Survey Sequence", Jun. 20, 2003, 2 pages.
Database EMBL [online], XP-002518400, "PUHKSO7TB ZM_0.6_1.0_KB *Zea mays* Genomic Clone ZMMBTa473B13, DNA Sequence", May 20, 2003, 2 pages.
Database EMBL [online], XP-002518401, "PUHKSO7TD ZM_0.6_1.0_KB *Zea mays* Genomic Clone ZMMBTa473B13, DNA Sequence", May 20, 2003, 2 pages.
Database EMBL [online], XP-002518402, "OG1DY21TV ZM_0.7_1.5_KB *Zea mays* Genomic Clone ZMMBMa0740D17, Genomic Survey Sequence", Aug. 25, 2003, 2 pages.
Aukerman, Milo J. et al., "Regulation of Flowering Time and Floral Organ Identity by a MicroRNA and its APETALA2-Like Target Genes" The Plant Cell, vol. 15, No. 11, pp. 2730-2741, Nov. 1, 2003. XP-002323691.
Chuck, George et al., "The control of maize spikelet meristem fate by the APETALA2-like gene indeterminate spikelet1", Genes & Development, 12:1145-1154, No. 8, Jan. 1, 1998, XP-000907506.
Okamuro, Jack K. et al., "The AP2 domain of APETALA2 defines a large new family of DNA binding proteins in Arabidopsis", Proc. Natl. Acad. Sci. USA, vol. 94, No. 13, pp. 7076-7081, Jun. 1, 1997 Plant Biology.
Riechmann, Jose Luis et al., "The AP2/EREBP Family of Plant Transcription Factors", Biol. Chem. vol. 379, pp. 633-646, Jun. 1, 1998. XP002938736.
Salvi, Silvio et al., "Toward positional closing of Vgt1, a QTL controlling the transition from the vegetative to the reproductive phase in maize", Plant Molecular Biology 48:601-613, Mar. 2002. XP-002518248.

(Continued)

*Primary Examiner* — Stuart F. Baum
(74) *Attorney, Agent, or Firm* — Pioneer Hi-Bred Int'l, Inc.

(57) ABSTRACT

The present invention provides compositions and methods for modulating flowering time in plants. Maize RAP2.7 nucleotide sequences are disclosed which upon overexpression cause later flowering and when inhibited cause earlier flowering. Also disclosed is a DNA sequence which acts as a regulator/enhancer of RAP2.7, termed VGT1. This sequence does not code for any known protein, but acts as either a RNAi element or a regulatory DNA or RNA element that either directly regulates expression of flowering genes such as Rap2.7 or specifically targets expression of other genes which control flowering genes such as Rap2.7. This element this can be used as a sequence-based marker to identify inbred and hybrids which have altered maturity. Methods for expressing these nucleotide sequences in a plant for modifying maturity and flowering in plants are provided as well as expression constructs, vectors, transformed cells and plants.

6 Claims, 24 Drawing Sheets

OTHER PUBLICATIONS

Vahala, Tiina et al., "Two APETALA2-like genes of *Picea abies* are differentially expressed during development", Journal of Experimental Botany, vol. 52, No. 358, pp. 1111-1115, May 2001. XP-002518246.

09/890,475, filed Nov. 13, 2001—Johanson, Urban.

Bowle, J.U., et al., "Deciphering the Message in Protein Sequences: Tolerance to Amino Acid Substitutions," Science 247:1306-1310, American Association for the Advancement of Science (1990).

McConnell, J.R., et al., "Role of Phabulosa and Phavoluta in determining radial patterning in shoots", Nature, vol. 411: p. 709-713, (2001).

Okamuro, Jack K., "The AP2 domain of APETALA2 defines a large new family of DNA binding proteins in Arabidopsis", Proc. Natl. Acad. Sci. USA, Jun. 1997, pp. 7076-7081, vol. 94.

BLAST search for rap2.7, Dec. 17, 2003.

\* cited by examiner

MQLDLNVAEAPPPVEMEASDSGSSVLNASEAASAGGAPAPAEEGSSSTPAVLEFSILIRS
DSDAAGADEDEDATPSPPPRHRHQHQQQLVTRELFPAGAGPPAPTPRHWAELGFFRADLQ
QQQAPGPRIVPHPHAAPPPAKKSRRGPRSR*SSQYRGVTFYRRTGRWESHIWDCGKQVYLG
GFDTAHAAARAYDRAAIKFRGVDADINFNLSDYEDDMKQMGSLSKEEFVHVLRRQSTGFS
RGS*SRYRGVTLHKCGRWEARMGQFLGKKAYDKAAIKCNGREAVTNFEPSTYHGELPTEVA
DVDLNLSISQPSPQRDKNSCLGLQLHHGPFEGSELKKTKIDDAPSELPGRPRRLSPVVAE
HPPAWPAQPPHPFFVFTNHEMSASGDLHRRPAGAVPSWAWQVAAAAPPPAALPSSAAASS
GFSNTATTAATAAPSASSLRYCPPPPPPPSSHHHPR

FIG. 3

```
   1 ............................caagacttgagctcgaa   17
                                  ||| ||    | |
 601 tagaatatataatctagagcaaactagttagtccaaatatttgtgttggg 650

18 aagtagcacagagagttcacaactcgaacggagctcaaatcactaacaca   67
     || |    ||    |  | |    |||    | || |  |    | |
 651 aattcaaccaccaaaattatttataggaaaaggttaaaccctatttccct  700

68 atcgatcaaatgcgaggaggcggagtgtgggagtcttagaatgcttagtg  117
     ||  | |         | ||     | | | ||||||        | |||
 701 ttcactaattaattggaagaacttgaggtgtagtcttcttcgtcgtcgtg  750

118 gatgcttagatgtttcctccatgcgcctagaggtcccttttatagcccca  167
      |  ||         |   |  |     ||    |    |    |  |||
 751 ccgttaatggggtcctagcacagtacttgctctaccgaggttgggtacca  800

168 agacacctaagagccgttggagatcaaca.......tggaatgctatcct  210
     ||   | |  |    | |  | |   |||       |||   |   | ||
 801 aggttcttttgttttgcttttgttagacaccccatgtggggagggtact   850

211 tgccttctgtcgagtggcgcaccggacaggtcctgtagattgttcggtgc  260
      || |       ||| |||||    |  ||    | ||    | |
 851 atgtttatcaaactgtagaaacctaacaggcgactttgacctctggagaa  900

261 gcgatctccttccaaatttggcatatccgaccgttgctcctctgggctga  310
     | | |   |   | | | | | |  | |    |   | ||   ||   ||
 901 tctttgtaaatgctacatagtgaaaccttgttgactcaccataggagtgt  950

311 ttggcg....................caccggacacagtccggtgcac   338
     || |                      || ||| |   ||
 951 ttaagggtttgatcgacttatggcaaaaagggggtcacggctcgtagta  1000

339 accggacagtccggtgcaccagct....gaccgttggagcagtccacgtg  384
      |   |  || || | ||    | |    || || | | ||||| |   |
1001 aagtgtaagacctttgcatagggttagaaactgatatatcagtcatgctc  1050

385 tcgcgcgaagattgc...gtggccgaccgttgctcaggcgaccgttggct  431
      |  |  |  ||| |    |    | |  |  |   |   | || || ||
1051 acaattaagaacggccttgggagctcctttgattagagatactgtagata  1100

432 caccggacagtccggtgcaccaccggacagtc...cggtgaattatagtc  478
     ||     |    |||       ||    | ||   |||  || || ||||
1101 cattcatgatgatggtttgatgatggtgcctctaattatgatttctagta  1150

479 gtacgccgccgtcgaaacccgagagcggcgagttcacagtggaccagcct  528
      |     |  ||  ||    ||   |  || ||  |       |    |
1151 ttttctctacgaggaggtactatttgggataataagctaggttttaagat  1200

529 ggcgcaccggacactgtccggtgcaccattggacattgtccggtgcacca  578
        |   |       || | || |   |       | | | |||   |||
1201 aaatttggcttatattaatgattaaaacctgataaagtaaaagcaacct   1250
```

FIG. 4A

```
 579 ccggacagtcccgtgtgcgaga................ccgagcacaag  611
     |   |||          | |                 || | || |
1251 gctatcagcttaactccacataaagctagtccattttagccaaacaagat 1300

612 attggctgcacagagccaagctttccttttctcccttcttttttagt  661
     ||| ||||    |     ||| |       |     | || | || |
1301 atttgctgagtacgttgatgtgtgcaaaatggagaacttttatcttaaaa 1350

662 cactgtttctagcacttggataaccatgttagtacataaaacaattcacc  711
     |||    |    |||    |   |    ||  |   |    |  ||  | 
1351 caccaggttgtccacactgcaaccactgctcaagcgaggatgaaggcaac 1400

712 aagtctagaaacataccttttgccttgattttcacttctcactttatttg  761
     | |  ||||   |    |  || || ||  |  |            |
1401 a..tgaagaactttcaggagtttctagacttcaaggagttttaaactaga 1448

762 gcacataagaacttaattaaacgtgttgggca................c  794
      |      |||   |  | |    || | |
1449 ttagtggtaaaccccagtcagctgcctgtgaaggccttatctttactacg 1498

795 ttaatcaccaaaacattatagaaatggcccaaaggcacatttcccttttca  844
     ||   |  | |||| |  |  ||        |    ||    ||    | |
1499 ttccgcgttagcactttgtttacttgttaagttgatggatacatcatgtt 1548

845 gtaataagttaatacctctttatatcattatttgaacactgtgcaatgat  894
     ||||||||||||||||||||||||||||||||||||||||||||||||||
1549 gtaataagttaatacctctttatatcattatttgaacactgtgcaatgat 1598

895 gttcatttatgtaatcgttgtgtacgtcagttctaattctagcacgtaca  944
     |||||||||||||||| |||||| ||||||||||||||||||||| ||||
1599 gttcatttatgtaatcgctgtgtatgtcagttctaattctagcacataca 1648

945 tggttcacatccaatttgtcttct.aaaaacgaatgtgacataatgtcat  993
     ||||||||||||| |||||||||| |||||||||||||||||||||||||
1649 tggttcacatccagtttgtcttctaaaaaacgaatgtgacataatgtcat 1698

994 atgtatgtgataatgcttttgttggggtccttcgtctttcaaaggtcct 1043
     ||||||||||||||||||||||||||||||||||||||||||||||||||
1699 atgtatgtgataatgcttttgttggggtccttcgtctttcaaaggtcct 1748

1044 caaaacacatttaaccattggttgttagcacatccttaagtgttgcagg 1093
     ||||||||||||||||||||||||||||||||||||||||||||||||||
1749 caaaacacatttaaccattggttgttagcacatccttaagtgttgcagg 1798

1094 agctttggtattgaataccttcggagcaggacatggaggaagacgaagat 1143
     ||||||||||||||||||||||||||||||||||||||||||||||||||
1799 agctttggtattgaataccttcggagcaggacatggaggaagacgaagat 1848

1144 gttagcttcgtcataacaacacaaggaaacgaaggcagaagtggaacaag 1193
     ||||||||||||||||||||||||||||||||||||||||||||||||||
1849 gttagcttcgtcataacaacacaaggaaacgaaggcagaagtggaacaag 1898

1194 gccgggatatggtgttttcaagactctgtatccaaagcaaaaagacaga 1243
     |||||||||||||||||||||||||||||||  |||||||||||||||| |
1899 gccgggatatggtgttttcaagactctgtaaccaaagcaaaaagacata 1948
```

*FIG. 4B*

```
1244 aagacgatactgcccttacataatttgtaaactatgtgaacaagttttat 1293
     ||||||||||||| ||||||||||||||||||||| |||||||||||||
1949 aagacgatactgtccttacataatttgtaaactatatgaacaagttttat 1998

1294 ggacatgtttgtaactttacacgaaattgtaccaccacactataaataga 1343
     |||||||||||||||||||||||||| ||||||||||||||||| ||||
1999 ggacatgtttgtaactttacacgaaactgtaccaccacactatagataga 2048

1344 taaatagtgccctgcatgaggcgcctcttgggaacaatgaggaacaactc 1393
     |||||||||||||||||||||||||||||||||||||||||||||||||
2049 taaatagtgccctgcatgaggcgcctcttgggaacaatgaggaacaactg 2098

1394 tgtataatccttttcttctaagtaccttcgggttttctcctcatcaaaa 1443
     ||| |||||||||||||||||||||||||||||||||||||||||||||
2099 tgtgtaatccttttcttctaagtaccttcgggttttctcctcatcaaaa 2148

1444 agccgaaggtactattgtaaattcgtttcatataaagaaagaaatcccaa 1493
     ||| ||||||||||||||||| ||||||||||||||||||||||||||
2149 agcggaaggtactattgtaaatttgtttcatataaagaaagaaatcccaa 2198

1494 gttgtttgagataagtaatcttatctagctttgttatagccatgtgtgta 1543
     ||||||||||||||||||||||||||||| ||||||||| |||||||||
2199 gttgtttgagataagtaatcttatctagcttcgttatagcccgtgtgtgta 2248

1544 atctttatctttatcctctgacaatcctatatattatatataataacctt 1593
     ||||||||||||||||||||||||||||||||||||||||||||||||||
2249 atctttatctttatcctctgacaatcctatatattatatataataacctt 2298

1594 cgtactttacttggatgtcccgaaggacaaactctttaagtacgaaggat 1643
     |||||||||||||||||| |||||||||||||||||||||||||||||
2299 cgtactttacttggatgtctcgaaggacaaactctttaagtacgaaggat 2348

1644 aacatcttttttaataatgtgttgccttg.tttttattgtgtacaacaa 1692
     ||||||||||||||||| ||||||||| ||||||||||||||||||||
2349 aacatcttttttaataatatgttgccttgttttttattgtgtacaacaa 2398

1693 ttaaaaacgagtgaccaacattttcatgtcagggtatggggacccattgg 1742
     ||||||||||||||||||||||||||||| |||||| ||||||||||||
2399 ttaaaaacgagtgaccaacattttcatgtcggggtatggagacccattgg 2448

1743 agactcgatatccaaatgaggatgagtatatgatgaatcctatacctatg 1792
     ||||||     | |||||||||||| ||||||||||||||||||||||||
2449 agactc.....ctaaatgaggatgggtatatgatgaatcctatacctatg 2493

1793 atgagtataagtatgagaatcaggatgagtataacttcatcagaataggt 1842
     |||||||||||||||||||||||||||||||||||||||||||| ||||
2494 atgagtataagtatgagaatcaggatgagtataacttcatcagaaaggt 2543

1843 gcgggggcgtccttgtgggcgtgcctaccgtgcgatcgcacaaggcctcc 1892
     ||||||||||||||||||||||||||| ||||||||||||||||||||
2544 acggggggcgtccttgtgggcgtgcctacagtgcgatcgcacaaggcctcc 2593

1893 aaaaccatagggcccccaaaatttataacaatctttatatacaatataaat 1942
     |||||||||| |||||||||||||||||||||||||||||||||||||||
2594 aaaaccatagagcccccaaaatttataacaatctttatatacaatataaat 2643
```

*FIG. 4C*

```
1943 .aaaaaatattatttatataaaatatttaccaacatatagcatagaatc 1991
     ||||||||||||||||||||||||||||||||||||||||||||||||
2644 aaaaaaatattatttatataaaatatttaccaacatatagcatagaatc 2693

1992 gtaaaagcgttgaaatcgatctgttcttattgttattcaaactatttacc 2041
     ||||||||||||||||||| ||||||||||||||||||||||||||||||
2694 gtaaaagcgttgaaatcgatatgttcttattgttattcaaactatttacc 2743

2042 tccagcacattgtagtcattagataaaaaagattgagatcttattgtcac 2091
     ||||||| ||||||||||||||||||||||||||||||||||||||||||
2744 tccagcatattgtagtcattagataaaaaagattgagatcttattgtcac 2793

2092 tatcttaagaagacacagttaaaagaggtagacaatatgtcaatatgctt 2141
     |||||||||| ||||||||||||||||||            ||||||| ||
2794 tatcttaagacgacacagttaaaagaggtaga........caatatgatt 2835

2142 tgatgcaagtgaccaattcgtgacgttgagtttcctctaagatttttgt.t 2190
     ||||||||| ||||||||||| |||||||||||| ||||||||| |
2836 tgatgcaagtaaccaattcgtggcgttgagtttcctttaagattttttaa 2885

2191 taaaaaattgctatgttgacattctaaattttataaagcagaggagcaaa 2240
     ||||||||||||||||||||||||||||||||||||||||||||||||||
2886 aaaaaaattgctatgttgacattctaaattttataaagcagaggagcaaa 2935

2241 actgagtaaaatcgcatttaatgataaaaatgtggaaagtgacaaaacta 2290
     |||||||||||||| | ||||||||||||||| |||||||||||||||||
2936 actgagtaaaatcgtaattaatgataaaaatgcggaaagtgacaaaacta 2985

2291 agaatacaattttaaatagtccaatattttttactatcttttgcacagg 2340
     |||||||||||||||||||||||||| |||||||||||||||||||||
2986 agaatacaattttaaatagtccaatatcttttactatcttttgcacagg 3035

2341 gcctctcaacttgggaggacgcttctgggtgtgggtttacaaattcgatg 2390
     ||||||||||||||||||||||||||||||||||||||||||||||||||
3036 gcctctcaacttgggaggacgcttctgggtgtgggtttacaaattcgatg 3085

2391 aaaaattccccattgacaaacgataggaggatattttctcccagcacaa 2440
     ||||||||||||||||||||||||||||||||||||||||||||||||
3086 aaaaattccccattgacaaacgataggaggatattttctcccagcacaa 3135

2441 aatagcatagccataaggcaacaaggcatggcaaaggatcgtatcatcgt 2490
     ||||||||||||||||||||||||||||||||||||||||||||||||||
3136 aatagcatagccataaggcaacaaggcatggcaaaggatcgtatcatcgt 3185

2491 catccgagacccattgctttctctctctcctcgtgctttcattactgg 2540
     ||||||||||||||||||||||||||||||||||||||||||||||||
3186 catccgagacccattgctttctctctctcctcgtgctttcattactgg 3235

2541 ggtgggggtggagtggaccagtggagtggagaaatgacaaatccaggccc 2590
     ||||||||||||||||||||||||||||||||||||||||||||||||||
3236 ggtgggggtggagtggaccagtggagtggagaaatgacaaatccaggccc 3285

2591 gcaggcagccccacccaccaaatcggccgagcagggtgcccaaatcagga 2640
     ||||||||||||||||||||||||||||||||||||||||||||||||||
3286 gcaggcagccccacccaccaaatcggccgagcagggtgcccaaatcagga 3335
```

FIG. 4D

```
2641 aggattttaaggttaaccggctgccaccgcccaccgccggtgacccagt 2690
     |||||||||||||||||||||||||||||||||||||||||||||||||
3336 aggattttaaggttaaccggctgccaccgcccaccgccggtgacccagt 3385

2691 ctctcttctatctatatattacccgcctccttttctcctctctctccgcc 2740
     |||||||||||||||||||||||||||||||||||||||||||||||||
3386 ctctcttctatctatatattacccgcctccttttctcctctctctccgcc 3435

2741 ccaccctccttcctcagctccgttgcgcaccgccaccgccggccggccag 2790
     |||||||||||||||||||||||||||||||||||||||||||||||||
3436 ccaccctccttcctcagctccgttgcgcaccgccaccgccggccggccag 3485

2791 ccgccggagcaccgaaagaccccgttctttcctgtaaaaaaaaacccgc 2840
     |||||||||||||||||||||||||||||||||||||||||||||||||
3486 ccgccggagcaccgaaagaccccgttctttcctgtaaaaaaaaacccgc 3535

2841 cgcctttagctagctaaccggtcgtcctcttcaccccctagctttgctag 2890
     |||||||||||||||||||||||||||||||||||||||||||||||||
3536 cgcctttagctagctaaccggtcgtcctcttcaccccctagctttgctag 3585

2891 ctctagctaggaacgaaagaaattaaaggataactgagattgctgattgg 2940
     |||||||||||||||||||||||||||||||||||||||||||||||||
3586 ctctagctaggaacgaaagaaattaaaggataactgagattgctgattgg 3635

2941 tggtccgggtacggtgttcttgagtcgtgaagcgacagtacagtggctag 2990
     |||||||||||||||||||||||||||||||||||||||||||||||||
3636 tggtccgggtacggtgttcttgagtcgtgaagcgacagtacagtggctag 3685

2991 ggtcgtgccgcccctgcagtctccggggttgcgtgcaggatggtcgtcag 3040
     |||||||||||||||||||||||||||||||||||||||||||||||||
3686 ggtcgtgccgcccctgcagtctccggggttgcgtgcaggatggtcgtcag 3735

3041 ggatcgggagtgaggaggcatcagctctcgcggtcgtggagcctaaatgt 3090
     |||||  ||||||||||||||||||||||||||||||||||||||||||
3736 ggatcaggagtgaggaggcatcagctctcgcggtcgtggagcctaaatgt 3785

3091 accgcaacaacgactcggcactctcctgcttctacctcttcctcctctgg 3140
     |||||||||||||||||||||||||||||||||||||||||||||||||
3786 accgcaacaacgactcggcactctcctgcttctacctcttcctcctctgg 3835

3141 ttcttcttcttgaagtagacaccaccagttcgccaggtagttagcagccc 3190
     |||||||||||||||||||||||||||||||||||||||||||||||||
3836 ttcttcttcttgaagtagacaccaccagttcgccaggtagttagcagccc 3885

3191 agttgcgactggggatcggtggcgggctgccgcttgcgagttgtaagctt 3240
     |||||||||||||||||||||||||||||||||||||||||||||||||
3886 agttgcgactggggatcggtggcgggctgccgcttgcgagttgtaagctt 3935

3241 ggaggggaggggagcaggagcaggagatgcagttggatctgaacgtggcc 3290
     ||||||||||||||||||||||||||||||||  |||||||||||||||
3936 ggaggggaggggagcaggagcaggagatgcagctggatctgaacgtggcc 3985

3291 gaggcgccgccgccggtggagatggaggcgagcgactcggggtcgtcggt 3340
     |||||||||||||||||||||||||||||||||||||||||||||||||
3986 gaggcgccgccgccggtggagatggaggcgagcgactcggggtcgtcggt 4035
```

FIG. 4E

```
3341 gctgaacgcgtcggaagcggcgtcggcgggcggcgcgcccgcgccggcgg 3390
     ||||||||||||||||||||||||||||||||||||||||||||||||||
4036 gctgaacgcgtcggaagcggcgtcggcgggcggcgcgcccgcgccggcgg 4085

3391 aggagggatctagctcaacgccggccgtgctggagttcagcatcctcatc 3440
     ||||||| || |||||||||||||| ||||||||||||||||||||||||
4086 aggaggggtccagctcaacgccggccgcgctggagttcagcatcctcatc 4135

3441 cggagcgatagcgacgcggccggcgcggacgaggacgaggacgccacgcc 3490
     |||||||| |||||||||||||||||||||||||||||||||||||||||
4136 cggagcgacagcgacgcggccggcgcggacgaggacgaggacgccacgcc 4185

3491 atcgcctcctcctcgccaccgccaccagcaccagcagcagctcgtgaccc 3540
      |||||||||||||||||||||||||||||||||||||||||||||||||
4186 gtcgcctcctcctcgccaccgccaccagcaccagcagcagctcgtgaccc 4235

3541 gcgagctgttcccggccggcgccggtccgccggccccgacgccgcggcat 3590
     ||||||||||||||| ||||||| |||||||||||| |||||||||||||
4236 gcgagctgttcccggctggcgccggcccgccggcccc ggcgccgcggcat 4285

3591 tgggccgagctcggcttcttccgcgccgacctgcagcagcaacaggcgcc 3640
     ||||||||||||||||||||||||||||||||||||||||||||||||||
4286 tgggccgagctcggcttcttccgcgccgacctgcagcagcaacaggcgcc 4335

3641 gggccccaggatcgtgccgcacccacacgccgcgccgccgccggccaaga 3690
     ||||||||||||||||||||||||||||||||||||||||||||||||||
4336 gggccccaggatcgtgccgcacccacacgccgcgccgccgccggccaaga 4385

3691 agagccgccgcggcccgcgctcccgcagctcgcagtaccgcggcgtcacc 3740
     ||||||||||||||||||||||||||||||||||||||||||||||||||
4386 agagccgccgcggcccgcgctcccgcagctcgcagtaccgcggcgtcacc 4435

3741 ttctaccgccgcacaggccgctgggagtcccacatctggtcagtactacc 3790
     ||||||||||||||||||||||||||||||||||||||||||||||||||
4436 ttctaccgccgcacaggccgctgggagtcccacatctggtcagtactacc 4485

3791 actgtctacaactagccacaccacaccgattgcttccgactctcattaat 3840
     ||||||||||||||||||||||||||||||||||||||||||||||||||
4486 actgtctacaactagccacaccacaccgattgcttccgactctcattaat 4535

3841 ttctgacacaaactctccgtcttcctcctcttctcccgcgacgcaggggat 3890
     ||||||||||||||||||||||||||||||||||||||||||||||||||
4536 ttctgacacaaactctccgtcttcctcctcttctcccgcgacgcagggat 4585

3891 tgcggcaagcaggtgtacctaggtgagcaagagcagatctcttttgcgtt 3940
     ||||||||||||||||||||||||||||||||||||||||||||||||||
4586 tgcggcaagcaggtgtacctaggtgagcaagagcagatctcttttgcgtt 4635

3941 cccaaagatttttcccctttagttccttatcccatcccatctcgaatgg 3990
     ||||||||| |||||||||||| ||||        |||||||||||||||
4636 cccaaaga.ttttcccctttagctcct.....catcccatctcgaatgg 4679

3991 cctagctaaccgattcagtggtggtccggctgctggccgatatacgcagg 4040
     ||||||||||||||||||| ||||||||||||||||||||||||||||||
4680 cctagctaaccgattcactggtggtccggctgctggccgatatacgcagg 4729
```

FIG. 4F

```
4041  tggattcgacaccgctcacgccgctgcaaggcacgcactggactggacgc  4090
      ||||||||||||||||||||||||||||||||||||||||||||||||||
4730  tggattcgacaccgctcacgccgctgcaaggcacgcactggactggacgc  4779

4091  ccagaattcttcgtcatgtgagtctctgaccg........aattgattga  4132
      ||||||||||||||||||||||||||||||||        ||||||||||
4780  ccagaattcttcgtcatgtgagtctctgaccggattggttgattgattga  4829

4133  ttaacgagtctctggctcctggaactcgcagggcgtacgaccgggcggcg  4182
      ||||||||||||||||||||||||||||||||||||||||||||||||||
4830  ttaacgagtctctggctcctggaactcgcagggcgtacgaccgggcggcg  4879

4183  atcaagttccgcggcgtcgacgccgacatcaacttcaacctcagcgacta  4232
      |||||||||||||||| |||||||||||||||||||||||||||||||||
4880  atcaagttccgcggcgtggacgccgacatcaacttcaacctcagcgacta  4929

4233  cgaggacgacatgaagcagatggggagcctgtccaaggaggagttcgtgc  4282
      ||||||||||||||||||||||||||||||||||||||||||||||||||
4930  cgaggacgacatgaagcagatggggagcctgtccaaggaggagttcgtgc  4979

4283  acgtcctgcgccgtcagagcaccggcttctcgagaggcagctccaggtac  4332
      |||||||||||||| |||||||||||||||||||||||||||||||||||
4980  acgtcctgcgccgccagagcaccggcttctcgagaggcagctccaggtac  5029

4333  agaggcgtcaccctgcacaagtgcggccgctgggaggcgcgcatggggca  4382
      ||||||||||||||||||||||||||||||||||||||||||||||||||
5030  agaggcgtcaccctgcacaagtgcggccgctgggaggcgcgcatggggca  5079

4383  gttcctcggcaagaagtaagaaccaaccaacgcttcttttcttttctttt  4432
      |||||||||||||||||||||||||||||||||||||||         |||
5080  gttcctcggcaagaagtaagaaccaaccaacgcttct..........ttt  5119

4433  tttttatagcatgcag.tgatgattcaaccttagttgtgccttcctcct  4481
      ||||||||||||||||  |||||||||     ||||||||||| |||||||
5120  tttttatagcatgcagatgatgattcacacttagttgtgcctctcctcct  5169

4482  aatcctatatatgtaggatttagtactggttgacta......tataagta  4525
      |||||     ||||||||||||||| |||||||||       |||  ||
5170  aatcc....tatgtaggatttagtattggttgactacatatctattgtta  5215

4526  tatatgtattgttcagtaaaagtatacataggttagctgcatgtttatgt  4575
      ||||||||||||||||||||||||||||||||||||||||||||||||||
5216  tatatgtattgttcagtaaaagtatacataggttagctgcatgtttatgt  5265

4576  atgtagctggttgtttcaatcagaagataaaaaaaaagggaagtagtggc  4625
      |||||||||||||||||||||||||||||||||| |||||||||||||||
5266  atgtagctggttgtttcaatcagaagataaaaagaaagggaagtagtggc  5315

4626  tagggaattcctccaatcctcaccggtgggaacgccgtgcttgggtgcag  4675
      ||||||||||||||||||||||||||||||||||||||||||||||||||
5316  tagggaattcctccaatcctcaccggtgggaacgccgtgcttgggtgcag  5365

4676  gtacatataccttgggctattcgacagcgaagtagaggctgcaaggttct  4725
      ||||||||||||||||||||||||||||||||||||||||||||||||||
5366  gtacatataccttgggctattcgacagcgaagtagaggctgcaaggttct  5415
```

*FIG. 4G*

```
4726 tcatcttggattctgccgttcatatatgcataatcatgtcttttaatttc 4775
     |||||||||||||||||||||||||||||||||| ||||||||| |||||
5416 tcatcttggattctgccgttcatatatgcataaccatgtcttttcatttc 5465

4776 caaagggttgagtaccgactcgattcctcttcgtgtctttttctttctt 4825
     |||||||||||||||||||||||||||||||      | |||||||||||
5466 caaagggttgagtaccgactcgattcctct......tttttttctttctt 5510

4826 tcttcgaaatccagagcctacgacaaggccgccatcaaatgcaatggcag 4875
     |||||||||||||||||| |||||||||||||||||||||||||||||||
5511 tcttcgaaatccagagcttacgacaaggccgccatcaaatgcaatggcag 5560

4876 agaggccgtgacgaacttcgagccgagcacgtatcacggggagctgccga 4925
     ||||||||||||||||||||||||||||||||||||||||||||||||||
5561 agaggccgtgacgaacttcgagccgagcacgtatcacggggagctgccga 5610

4926 ctgaaggtactttttctttctgcatatatat.atcttcaggtattatt 4974
     |||||||||||| |||||||||||||||||| ||||||||||||||
5611 ctgaaggtacgta.tttctttctgcatatatataatcttcaggtattatt 5659

4975 ggctattaaactgcttggatcttactgcttcttctgcagttgctgatgtc 5024
     ||||||||||||||||||||| ||||||||||||||||||||||||||||
5660 ggctattaaactgcttggatttactgcttcttctgcagttgctgatgtc 5709

5025 gatctgaacctgagcatatctcagccgagcccccaaagagacaagaacag 5074
     ||||||||||||||||||||||||||||||||||||||||||||||||||
5710 gatctgaacctgagcatatctcagccgagcccccaaagagacaagaacag 5759

5075 ctgcctaggtctgcagctccaccacggaccattcgagggctccgaactga 5124
     ||||||||||||||||||||||||||||||||||||||||||||||||||
5760 ctgcctaggtctgcagctccaccacggaccattcgagggctccgaactga 5809

5125 agaaaccaaggcaagcgctaacgatagatataccttgacaagctagtat 5174
     | ||||||||||||||||||||||||||||||||||||||||||||||||
5810 agaaaaccaaggcaagcgctaacgatagatataccttgacaagctagtat 5859

5175 caaacaaaaccagtaaaaaaagtttactttcttgtcgaatttcattgcct 5224
     ||||||||||||| |       |||||||||||||||||||||||||||
5860 caaacaaaaccagt..atttttttactttcttgtcgaatttcattgcct 5907

5225 acctgatgtacgtacttgtgcttctgcacaaaataacgaaatccttttgc 5274
     |||||||||||||||||||||||||||||| |||||||||||||||||||
5908 acctgatgtacgtacttgtgcttctgcacagaataacgaaatccttttgc 5957

5275 cctctgatgatgatgcagatcgacgatgctccctctgagctaccgggccg 5324
     |||||||||||||||||||||||||||||||||||||||| || ||||||
5958 cctctgatgatgatgcagatcgacgatgctccctctgacctcccgggccg 6007

5325 ccctcgtcagctgtctcctctcgtggctgagcatccgccggcctggcctg 5374
     ||||||| ||||||||||||||||||||||||||||||||||||||||||
6008 ccctcgtcggctgtctcctctcgtggctgagcatccgccggcctggcctg 6057

5375 cgcagccgcctcaccccttcttcgtcttcacaaaccatgaggttaggtga 5424
     ||||||||||||||||||||||||||||||||||||||||||||||||||
6058 cgcagccgcctcaccccttcttcgtcttcacaaaccatgaggttaggtga 6107
```

*FIG. 4H*

```
5425 cagctactgatcgagatgcagcagcagttcaaa................. 5457
     |||||||||||||||||||||||||||||||||
6108 cagctactgatcgagatgcagcagcagttcaaaacttagatccggtccct 6157
                              .
                              .
                              .

5458 ...cctgtctgttccaaggacctttaggccggattaccaaatcatcggtc 5504
        ||||||||||||||||||||||||||||||||||||||||||||||
6308 tgtcctgtctgttccaaggacctttaggccggattaccaaatcatcggtc 6357
5505 aactgtcctgtctgttatatatttatgtgttaatttataatacaagtgtg 5554
     |||||||||||||||||||||||||||||    |||||||||||||||||
6358 aactgtcctgtctgttatatatttatgtg....tttataatacaagtgtg 6403
5555 actattttcaaaccttccttcaaaatgcatgaaaagag..ttttttta 5602
     ||||||||||||||||||||||||||||||||||||||  ||||||||
6404 actattttcaaaccttccttcaaaatgcatgaaaagagttttttttta 6453
5603 acgaaaggcgaaaagaaaatatgatac.ttgggacaggagcaagcttgga 5651
     |||||||||||||||||||||||||| ||||||||||||||||||||||
6454 acgaaaggcgaaaagaaaatatgatactttgggacaggagcaagcttgga 6503
5652 tcatcagaaagtattattaattaggatcactgagctgttcattttgttct 5701
     ||||||||||||||||||||||||||||||||||||||||||||||||||
6504 tcatcagaaagtattattaattaggatcactgagctgttcattttgttct 6553
5702 tgagtcaatcctaatcgtactatgtcagtgaatgaacttgtgttgcacca 5751
     ||| ||||||||||||||||||||||||||||||||||||||||||||||
6554 tgaatcaatcctaatcgtactatgtcagtgaatgaacttgtgttgcacca 6603
5752 atgcagatgagtgcatcaggagatctccacaggaggcctgcaggggctgt 5801
     ||||||||||||||||||||||||||||||||||||||||||||||||||
6604 atgcagatgagtgcatcaggagatctccacaggaggcctgcaggggctgt 6653
5802 tcccagctgggcatggcaggtggcagcagcagctcctcctcctgccgccc 5851
     ||||||||||||||||||||||||||||||||||||||||||||||||||
6654 tcccagctgggcatggcaggtggcagcagcagctcctcctcctgccgccc 6703
5852 tgccgtcgtccgctgcagcatcatcaggattctccaacaccgccacgaca 5901
     ||||||||||||||||||||||||||||||||||||||||||||||||||
6704 tgccgtcgtccgctgcagcatcatcaggattctccaacaccgccacgaca 6753
5902 gctgccaccaccgccccatcggcctcctccctccggtactgc...ccgcc 5948
     ||||||||| ||||||||||||||||||||||||||||||||   |||||
6754 gctgccaccgccgccccatcggcctcctccctccggtactgcccgccgcc 6803
5949 gccgccgccgccgtcgagccatcaccatccccgctgagagaatcaagaag 5998
     |||||||||||||||||||||||||||||| |||||||||||||||||||
6804 gccgccgccgccgtcgagccatcaccatcgccgctgagagaatcaagaag 6853
5999 ccgcactgtaaatctgccgg....gaagctagcattttcccccggcccc 6044
     ||||||||||||||||||||    |||||||||||||||||||||||||
6854 ccgcactgtaaatctgccgggaatgaagctagcattttcccccggccc. 6902
```

FIG. 41

```
6045  tcccctctccgggcgttgcgacttttcagttttgcgccgccggccggg  6094
      ||||||||||||||||||||||||||||||||||||||||| |||||
6903 .tccctctccgggcgttgcgacttttcagttttgcgccgccagccggg  6951

6095  gtggtggtttcttgtagccgatcgattggattcctcgtattactgctgct  6144
      ||||||||||||||| ||||||| |||||||||||||||||   |||||
6952  gtggtggtttcttgtaaccgatcggttggattcctcgtatta...ctgct  6998

6145  tacactcccaattaagtgaaaaaaaaacgctcctctactctttacactac  6194
      ||||||||||||||||||   ||||||||||||||||||||||||||||
6999  tacactcccaattaagtg.ggaaaaaacgctcctctactctttacactag  7047

6195  acacactgttagctgatcgattggacgtacttgctagctgctgttgctgc  6244
      |||||||||||||||||||||||||||||||||||||||||||||||||
7048  acacactgttagctgatcgattggacgtacttgctagctgctgttgctgc  7097

6245  tgctagcttgagattgactaacttcagcacttggattgatctatatctat  6294
      ||||||||  |||||||||||||   |||||||||||||||||||||||
7098  tgctagctagagattgactaactgaagcacttggattgatctatatctat  7147

6295  atgactatatagacgacacattgtgtacgtgtagataatatttcttcttt  6344
      ||||||||||    |||||||||||||||||||||||||||||||| ||
7148  atgactatata...gacacattgtgtacgtgtagataatatttctttatt  7194

6345  tcctgaccgccataaaactgtttactctggccattttgaactaaaggcta  6394
      ||||||||||||||||||||||||||| |||||||||||||||||||||
7195  tcctgaccgccataaaactgtttactctagccattttgaactaaaggcta  7244

6395  gctacaaatgagtgtccttctcggccttctacatgttctggtcatggaca  6444
      ||||||||||||||||| |||||||||||||||||||||||||||||||
7245  gctacaaatgagtgtccgtctcggccttctacatgttctggtcatggaca  7294

6445  tcgagagatcaaacttctctgtcctgcttactagatacgtactagattta  6494
      |||||||||||||||||||||||||||||||||||||||||||||||||
7295  tcgagagatcaaacttctctgtcctgcttactagatacgtactagattta  7344

6495  cttagcctagatagattccgttccaaactcgaggccaggcgcatcgagat  6544
      |||||||||||||||| ||||||||||||||||||||||||||||||||
7345  cttagcctagatagatttcgttccaaactcgaggccaggcgcatcgagat  7394

6545  ccgagaacttcatccactcgtcgctcatcatgctgcatgcatgatggtct  6594
      ||||| |||||||||||||||||| ||||| |||||||||||||||||||
7395  ccgagcacttcatccactcgtcgttcatcgtgctgcatgcatgatggtct  7444

6595  caactctgaggcatgcaaacgcagtgag.acgaactgggaggaatttata  6643
      ||||||||||||||||||||||||||||  ||||||||||||||||||||
7445  caactctgaggcatgcaaacgcagtgagaacgaactgggaggaatttata  7494

6644  tagagtatatattgtccggcctgttggtgataaagatagaatgcatgcac  6693
      |||||||||||||||||||||||||||||||||||||||||||||||||
7495  tagagtatatattgtccggcctgttggtgataaagatagaatgcatgcac  7544

6694  gctaactgccaacatgcatgggtgctgcatcgaattttggtat.....g  6738
      ||||||||||||||||||||||||||||||||||||||||||||    |
7545  gctaactgccaacatgcatgggtgctgcatcgaattttggtatggtgcg  7594
```

FIG. 4J

```
6739 gtgcatgcataccgtgcattggtgctctgctagtactaggaccaatctcc 6788
     ||||||||||||||||||||||||
7595 gtgcatgcataccgtgcattggtg....................gg 7620

6789 atggctccattagatctcttgtttactcgtctccatgtgcctctcaaagt 6838
       |  |||||  |  || |   ||     |  | ||   || | || |
7621 gagaatccatgaaatagcacttgtttgagacggcgt.....tcacgaaat 7665

6839 gtgtactagctagttgcggcacacaagttggcagttgtttgttgtttcag 6888
        |     |     |  || |   |  ||| ||||||
7666 agcatccgatttcaagtaattcatagaatagcacttgttttaccaaatta 7715

6889 cggggaagaaggaggtcaccgttgtcatcgtcaggggcgaagctaggatc 6938
          |  ||  |        | |  |  || |     |       || |
7716 attcagaaaataacactctatctatattttgcattctttttattgcttacc 7765

6939 agaagacagaggggggcaggcttagcctccaagcgaccaaaccagtaagaa 6988
       |      |  ||  |    ||| ||        |||  |  |
7766 tcacatacaaatggaccaaattacccctatttatcacaaccttctttttt 7815

6989 cacaatataaaaatggcaagagaaccaaccataatatatatattgatata 7038
        |    ||        |   | |||   |   ||||  |    ||| ||
7816 tatctcttatgtccataagaacaacataaataaataaatatatgaccta 7865

7039 taatcttcattaaaaaacagtataatgaaacaacatctatttttgtcaaac 7088
     || | ||       || |||| ||| || |      | | |   | ||
7866 tattttatagtgttaaacatacaaatagacacatgttttatgaacgaag 7915

7089 aaaataaaattaaatctcagttatttttgaatttagctctacgtgtattag 7138
     ||   | ||| ||        | || ||||||| ||| || | || |
7916 aagtctatatttaa........ctattaaatttagaactaggtatcttcg 7957

7139 ctagatcataggtgaaagt..cgcctagaggggggggtgaataggggcgaaa 7186
      | |   |  | ||| |    | || ||    | || |||| |   |
7958 gttgtcgaacttttaaaattagacatatttggtccattaaaaggtcttag 8007

7187 ctgaaatttacaaatataaacacaactacaagccgggttagcgttataag 7236
       |  | ||| | |       ||  | | | || |    ||  ||  ||
8008 attgtacttcctatgttctttttatttgatacggttgttttttttcaa. 8056
                                              .
                                              .
                                              .
```

| Pos. | AFLP14 | L2.63 | 33.2 | tear4a | tear4b | tear2 | tear5 | tear7 | 19_0a | 19_0b | 19_1 | | 19_1.5 | 19_16 | 19_15 | 19_10 | 19_11 | 19_12 | 1.m22 | 39_3 | 91.i23 | AFLP13 | DPS | ND |
|---|---|---|---|---|---|---|---|---|---|---|---|---|---|---|---|---|---|---|---|---|---|---|---|---|
| | RFLP | PCR | SNP | SNP | SNP | CAP | CAP | CAP | CAP | CAP | CAP | | PCR | SNP | PCR | SNP | PCR | PCR | PCR | PCR | SNP | RFLP | | |
| | | 19.5 | 22.8 | 32.0 | 32.0 | 35.4 | 38.8 | 40.4 | 59.9 | 60.8 | 60.9 | | 61.6 | 62.5 | 63.6 | 67.1 | 69.0 | 69.3 | 80.9 | 82.2 | 83.4 | | | |
| N28 | A | A | A | A | A | A | A | A | A | A | A | A | A | A | A | A | A | A | A | A | A | A | 73.2 | 21.5 |
| C22 | B | B | B | B | B | B | B | B | B | B | B | B | B | B | B | B | B | B | B | B | B | B | 64.8 | 19.6 |
| R5 | B | B | B | B | B | B | B | B | - | - | B | B | - | - | B | B | A | A | A | A | A | A | 64.0 | 19.8 |
| R6 | B | B | B | A | B | A | B | B | - | - | B | A | - | B | B | B | B | B | B | B | B | A | 66.3 | 19.4 |
| R19 | A | A | A | B | A | B | A | A | - | - | A | B | A | A | A | A | A | A | A | A | A | A | 64.0 | 21.8 |
| R22 | B | B | B | A | B | A | B | B | - | - | B | A | - | B | B | B | B | B | B | B | B | B | 66.3 | 21.5 |
| R31 | A | A | A | B | A | B | A | A | - | - | A | B | A | A | A | A | A | A | A | A | A | A | 70.7 | 21.5 |
| R33 | B | B | B | A | B | A | B | B | - | - | B | B | B | B | B | B | B | B | B | B | B | B | 66.3 | 20.1 |
| R38 | A | A | - | B | A | B | A | A | - | - | A | B | A | B | A | B | B | B | B | B | B | B | 73.0 | 22.0 |
| R40 | B | B | B | A | B | A | B | B | A | - | B | A | A | B | B | B | B | B | B | B | B | B | 72.0 | 21.4 |
| R41 | A | A | - | B | A | B | A | A | - | - | A | B | A | A | A | B | A | A | A | A | A | A | 63.3 | 20.0 |
| R42 | A | A | B | B | A | B | A | A | - | - | A | B | A | B | B | B | B | B | B | B | B | A | 65.7 | 20.0 |
| R43 | B | B | A | A | B | A | B | B | - | B | B | A | B | B | B | B | B | B | B | B | B | B | 70.7 | 22.2 |
| R48 | A | A | - | B | A | B | A | A | - | - | A | B | A | B | A | - | B | A | A | A | A | B | 66.7 | 19.3 |
| R50 | A | - | - | A | A | A | A | A | - | - | A | B | A | A | A | B | B | B | B | B | B | B | 66.0 | 19.3 |
| R58 | B | B | B | A | B | A | B | B | - | - | B | A | B | B | B | - | B | B | B | B | B | B | 72.0 | 21.9 |
| R66 | A | A | - | B | A | B | A | A | A | B | A | B | A | A | A | - | A | A | A | A | A | A | 73.7 | 21.4 |
| R67 | A | A | A | A | A | A | A | A | - | - | A | A | A | A | A | B | B | B | B | B | B | B | 68.7 | 20.4 |
| R70 | A | A | A | B | A | B | A | A | - | - | A | B | A | B | A | B | B | B | B | B | B | B | 71.0 | 21.8 |
| | A | A | A | B | A | B | A | A | - | - | A | B | A | B | A | B | B | B | B | B | B | B | 69.3 | 20.5 |

```
VGT1_C22      (1)   ------------------------------------------------
VGT1_MO17     (1)   ------------------------------------------------
VGT1_B73      (1)   ATAAATTTATTTTGAAGATATAAATATTTTAACGGTATTTTTTATTAATA
Consensus     (1)
                    51                                             100
VGT1_C22      (1)   ------------------------------------------------
VGT1_MO17     (1)   ------------------------------------------------
VGT1_B73      (51)  AAATGATTTATATGGATTATACAGATAGAGTCTCTCTCTACTCTCTAGTC
Consensus     (51)
                    101                                            150
VGT1_C22      (1)   ------------------------------------------------
VGT1_MO17     (1)   ------------------------------------------------
VGT1_B73      (101) CTGTGTACGTGCAGGTTTGGCAAGGTATGAACAGGACGTCAAACGCGTAC
Consensus     (101)
                    151                                            200
VGT1_C22      (1)   ---------------CTCCACCTCTCTCGTACGCTTTGATTGGCCGCTC
VGT1_MO17     (1)   ---------------CTCCACCTCTCTCGTACGCTTTGATTGGCCGCTC
VGT1_B73      (151) GTGTACTCCACACACACTCCACCTCTCTCGTACGCTTTGATTGGCCGCTC
Consensus     (151)                CTCCACCTCTCTCGTACGCTTTGATTGGCCGCTC
                    201                                            250
VGT1_C22      (35)  GCACGCATTTATCGCCAAGATCGGGCTTGCCCATCACTGGGATCATCCTG
VGT1_MO17     (35)  GCACGCATTTATCGCCAAGATCGGGCTTGCCCATCACTGGGATCATCCTG
VGT1_B73      (201) GCACGCATTTATCGCCAAGATCGGGCTTGCCCATCACTGGGATCATCCTG
Consensus     (201) GCACGCATTTATCGCCAAGATCGGGCTTGCCCATCACTGGGATCATCCTG
                    251                                            300
VGT1_C22      (85)  GCTGGCTGGCTGGCCGGCCACATATCAAACATGG-------ATTTGCTA
VGT1_MO17     (85)  GCTGGCTGGCTGGCCGGCCACATATCAAACATGG-------ATTTGCTA
VGT1_B73      (251) GCTGGCTGGCTGGCCGGCCACATATCAAACATGGATTTGCTCATTTGCTA
Consensus     (251) GCTGGCTGGCTGGCCGGCCACATATCAAACATGG       ATTTGCTA
                    301                                            350
VGT1_C22      (127) TATTTTAAATGCCTGAAATATGTTATACTATGTTTTTTAGATAACGATCT
VGT1_MO17     (127) TATTTTAAATGCCTGAAATATGTTATACTATGTTTTTTAGATAACGATCT
VGT1_B73      (301) TATTTTAAATGCCTGAAATATGTTATACTATGTTTTTTAGATAACGATCT
Consensus     (301) TATTTTAAATGCCTGAAATATGTTATACTATGTTTTTTAGATAACGATCT
                    351                                            400
VGT1_C22      (177) TTACAGTCGATTTATGAATGTGTAGAATTAAGATTGAGCTTCCTGATGAA
VGT1_MO17     (177) TTACAGTCGATTTATGAATGTGTAGAATTAAGATTGAGCTTCCTGATGAA
VGT1_B73      (351) TTACAGTCGATTTATGAATGTGTAGAATTAAGATTGAGCTTCCTGATGAA
Consensus     (351) TTACAGTCGATTTATGAATGTGTAGAATTAAGATTGAGCTTCCTGATGAA
                    401                                            450
VGT1_C22      (227) AAAATCAGGCAAGAGGCTCTTTTGGTTGGAGACCTGGCATGGCACTTGCC
VGT1_MO17     (227) AAAATCAGGCAAGAGGCTCTTTTGGTTGGAGACCTGGCATGGCACTTGCC
VGT1_B73      (401) AAAATCAGGCAAGAGGCTCTTTTGGTTGGAGACCTGGCATGGCACTTGCC
Consensus     (401) AAAATCAGGCAAGAGGCTCTTTTGGTTGGAGACCTGGCATGGCACTTGCC
                    451                                            500
VGT1_C22      (277) TGCGAGTCAAGCAAACCCTATGCCACTGTTTGGACCAGGCCACTTTCCTA
VGT1_MO17     (277) TGCGAGTCAAGCAAACCCTATGCCACTGTTTGGACCAGGCCACTTTCCTA
VGT1_B73      (451) TGCGAGTCAAGCAAACCCTATGCCACTGTTTGGACCAAGCCACTTTCCTA
Consensus     (451) TGCGAGTCAAGCAAACCCTATGCCACTGTTTGGACCAGGCCACTTTCCTA
                    501                                            550
VGT1_C22      (327) GAGAGCCGAATCAGACATCACTATCGGAATTCGAATGAGTGCTCAGCACT
VGT1_MO17     (327) GAGAGCCGAATCAGACATCACTATCGGAATTCGAATGAGTGCTCAGCACT
VGT1_B73      (501) GAGAGCCGAATCAGACATCACTATCGGAATTCGAATGAGTGCTCAGCACT
Consensus     (501) GAGAGCCGAATCAGACATCACTATCGGAATTCGAATGAGTGCTCAGCACT
                    551                                            600
VGT1_C22      (377) TTACCGAGTGCAATTAATCGGACACTCGGCAAAGCATTCTTTGTCGAGTG
VGT1_MO17     (377) TTACCGAGTGCAATTAATCGGACACTCGGCAAAGCATTCTTTGTCGAGTG
VGT1_B73      (551) TTACCGAGTGTAATTAATCGGACACTCGGCAAAGCATTCTTTGTCGAGTG
Consensus     (551) TTACCGAGTGCAATTAATCGGACACTCGGCAAAGCATTCTTTGTCGAGTG
```

*FIG. 9A*

```
                     601                                                650
VGT1_C22      (427)  CCACTCTCGGCGAACTAATAAGGCTCTCGGGACAGATCTCGTATGTCGAG
VGT1_MO17     (427)  CCACTCTCGGCGAACTAATAAGGCTCTCGGGACAGATCTCGTATGTCGAG
VGT1_B73      (601)  TCACTCTCGGCGAACTAATAAGGCTCTCGGGACAGATCTCGTATGTCGAG
Consensus     (601)  CCACTCTCGGCGAACTAATAAGGCTCTCGGGACAGATCTCGTATGTCGAG
                     651                                                700
VGT1_C22      (477)  AGCGGAACACTCGACATAGAAAAACACTCGGCAAAAGAGGTTTTGTCAA
VGT1_MO17     (477)  AGCGGAACACTCGACATAGAAAAACACTCGGCAAAAGAGGTTTTGCCAA
VGT1_B73      (651)  AGCGGAACACTCGACATAGAAAAACACTCGGCAAAAGAGGTTTTACCGAA
Consensus     (651)  AGCGGAACACTCGACATAGAAAAACACTCGGCAAAAGAGGTTTTGCCAA
                     701                                                750
VGT1_C22      (527)  TGACAAGCTCTCGGCAAAATGTGACACTCGATAAGGGTCGTCAAGAGTCG
VGT1_MO17     (527)  TGCCAAGCTCTCGGCAAAATGCGACACTCGGTAAGGGTCGTCAAGAGTCG
VGT1_B73      (701)  TGCCAAGCTCTCGGCAAAATGCGACACTCGGTAAGGGTCGTCAAGAGTCG
Consensus     (701)  TGCCAAGCTCTCGGCAAAATGCGACACTCGGTAAGGGTCGTCAAGAGTCG
                     751                                                800
VGT1_C22      (577)  TCTATTGTTGACGGCCATTAACTTTCCCGAGTGTCAAACGTTGACACTTG
VGT1_MO17     (577)  TCTATTGTTGACGGCCATTAACTTTCCCGAGTGTCAAACGTTGACACTTG
VGT1_B73      (751)  TCTATTGTTGACGGCCATTAACTTTCCCGAGTGTCAAACGTTGACACTTG
Consensus     (751)  TCTATTGTTGACGGCCATTAACTTTCCCGAGTGTCAAACGTTGACACTTG
                     801                                                850
VGT1_C22      (627)  GGAATTATCTTCTTTTTGTCGATTGTAACCTGGCAAACCCTCGGCAAAAG
VGT1_MO17     (627)  GGAATTATCTTCTTTTTGTCGAGTGTAACCTGGCAAACCCTCGGCAAAAA
VGT1_B73      (801)  GGAATTATCTTCTTTTTGTCGATTGTAACCTGGCAAACCCTCGGCAAAAG
Consensus     (801)  GGAATTATCTTCTTTTTGTCGATTGTAACCTGGCAAACCCTCGGCAAAAG
                     851                                                900
VGT1_C22      (677)  TATACTTTGCGGAGTGTCTTCCCTCAACACTCGATAAAGAATATTTGTTT
VGT1_MO17     (677)  TATACTTTGCGGAGTGTCTTCCCTCGACACTCGATAAAGAATATTTGTTT
VGT1_B73      (851)  TATACTTTACGGAGTGTCTTCCCTCAACACTCGATAAAGAATATTTGTTT
Consensus     (851)  TATACTTTGCGGAGTGTCTTCCCTCAACACTCGATAAAGAATATTTGTTT
                     901                                                950
VGT1_C22      (727)  CTTTTTCTTTTTTCTATACCAAACTCTTTGTGACGTTTTTTCTGCAGTAT
VGT1_MO17     (727)  CTTTTTCTTTTTTCTATACCAAACTCTTTGTGACGTTTTTTCTGCAGTAT
VGT1_B73      (901)  CTTTTTCTTTTTTCTATACCAAACTCTTTGTGACGTTTTTTCTGCAGTAT
Consensus     (901)  CTTTTTCTTTTTTCTATACCAAACTCTTTGTGACGTTTTTTCTGCAGTAT
                     951                                               1000
VGT1_C22      (777)  ATAGACATACATATTCAATTTTACACAATTATCAAAGTGTTTGCTATAAT
VGT1_MO17     (777)  ATAGACATACATATTCAATTTTACACAATTATCAAAGTGTTTGCTATAAT
VGT1_B73      (951)  ATAGACATACATATTCAATTTTACACAATTATCAAAGTGTTTGCTATAAT
Consensus     (951)  ATAGACATACATATTCAATTTTACACAATTATCAAAGTGTTTGCTATAAT
                     1001                                              1050
VGT1_C22      (827)  TAATAGATTTAGTTTGTTTAATTGAATTTCTGAGAACCAATCAAATAGAC
VGT1_MO17     (827)  TAATAGATTTAGTTTGTTTAATTGAATTTCTGAGAACCAACCAAATAGAC
VGT1_B73     (1001)  TAATAGATTTAGTTTGTTTAATTGAATTTCTGAGAACCAACCAAATAGAC
Consensus    (1001)  TAATAGATTTAGTTTGTTTAATTGAATTTCTGAGAACCAACCAAATAGAC
                     1051                                              1100
VGT1_C22      (877)  CCGAATTAGACATATCTAGACATTTAAAAAGTAAGATACTAAAAAATAAT
VGT1_MO17     (877)  CCGAATTAGACATATCTAGACATTTAAAAAGTAAGATACTAAAAAATAAT
VGT1_B73     (1051)  CCGAATTAGACATATCTAGACATTTAAAAAGTAAGATACTAAAAAATAAT
Consensus    (1051)  CCGAATTAGACATATCTAGACATTTAAAAAGTAAGATACTAAAAAATAAT
                     1101                                              1150
VGT1_C22      (927)  AGTGTTTACCTTCAACCGGTACTAAATGTCATTCCTGTAGTAGACAGGAT
VGT1_MO17     (927)  AGTGTTTACCTTCAACCGGTACTAAATATCATTCCTGTAGTAGACAGGAT
VGT1_B73     (1101)  AGTGTTTACCTTCAACCGGTACTAAATATCATTCCTGTAGTAGACAGGAT
Consensus    (1101)  AGTGTTTACCTTCAACCGGTACTAAATATCATTCCTGTAGTAGACAGGAT
```

*FIG. 9B*

```
                          1151                                    1200
VGT1_C22     (977)  AACGAAAGCTAGTCTATTTAGATCATCAGTTCCAGTTCGAGATTTTAAAT
VGT1_MO17    (977)  AACGAAAGCTAGTCTATTTAGATCATCAGTTCCAGTTCGAGATTTTAAAT
VGT1_B73    (1151)  AACGAAAGCTAGTCTATTTAGATCATCAGTTCCAGTTCGAGATTTTAAAT
Consensus   (1151)  AACGAAAGCTAGTCTATTTAGATCATCAGTTCCAGTTCGAGATTTTAAAT
                          1201                                    1250
VGT1_C22    (1027)  GCTAGTCCCTCCATTTCAATTTACAATTTATTTAATTTTTTTAGTGTGAT
VGT1_MO17   (1027)  GCTAGTCCCTCCATTTCAATTTACAATTTATTTAATTTTTTTAGTGTGAT
VGT1_B73    (1201)  GCTAGTCCCTCCATTTCAATTTACAATTTATTTAATTTTTTTAGTGTGAT
Consensus   (1201)  GCTAGTCCCTCCATTTCAATTTACAATTTATTTAATTTTTTTAGTGTGAT
                          1251                                    1300
VGT1_C22    (1077)  ACCGTTTAGCGTA--------------TGTAGCTTTGA-TTTTTTTATAT
VGT1_MO17   (1077)  ACCGTTTAGCGTA--------------TGTAGCTTTGATTTTTTTTATAT
VGT1_B73    (1251)  ACCGTTTAGCATATAATATACTTTAAGTGTAGCTTTGA-TTTTTTTATAT
Consensus   (1251)  ACCGTTTAGCGTA               TGTAGCTTTGA TTTTTTTATAT
                          1301                                    1350
VGT1_C22    (1112)  ATTTTTGCAAAATTTTGAATAAGACAAGTGTGTCAAATTTGGTGTAAAAA
VGT1_MO17   (1113)  ATTTTTGCAAAATTTTGAATAAGACAAGTGTGTCAAATTTGGTGTAAAAA
VGT1_B73    (1300)  ATTTTTGCAAAATTTTGAATAAGACAAGTATGTCAAATTTGGTGTAAAAA
Consensus   (1301)  ATTTTTGCAAAATTTTGAATAAGACAAGTGTGTCAAATTTGGTGTAAAAA
                          1351                                    1400
VGT1_C22    (1162)  TTAAACGAAATTATAAATTGGAGCGGAGGGAGTAGAAATCTACGATTTTT
VGT1_MO17   (1163)  TTAAACGAAATTATAAATTGGAGCGGAGGGAGTAGAAATCTACGATTTTT
VGT1_B73    (1350)  TTAAACGAATTTATAAATTGGAGCGGAGGGAGTAGAAATCTACGATTTTT
Consensus   (1351)  TTAAACGAAATTATAAATTGGAGCGGAGGGAGTAGAAATCTACGATTTTT
                          1401                                    1450
VGT1_C22    (1212)  CTAGCTGAGGCAGACTGTGCGCATTCCCATCCATCGAGTCCACTTGCACC
VGT1_MO17   (1213)  CTAGCTGAGGCAGACTGTGCGCATTCCCATCCATCGAGTCCACTTGCACC
VGT1_B73    (1400)  CTAGCTGAGGCAGACTGTGCGCATTCCCATCCATCGAGTCCACTTGCACC
Consensus   (1401)  CTAGCTGAGGCAGACTGTGCGCATTCCCATCCATCGAGTCCACTTGCACC
                          1451                                    1500
VGT1_C22    (1262)  TCTCCTCGACATGAATACGAATGTACGATCCGATGAATTCCCCACAAAGA
VGT1_MO17   (1263)  TCTCCTCGACATGAATACGAATGTACGATCCGATGAATTCCCCACAAAGA
VGT1_B73    (1450)  TCTCCTCGACATGAATACGAATGTACGATCCGATGAATTCCCCACAAAGA
Consensus   (1451)  TCTCCTCGACATGAATACGAATGTACGATCCGATGAATTCCCCACAAAGA
                          1501                                    1550
VGT1_C22    (1312)  AGCAATTAACGTCAAATCCATCATCGTCATAAAACGACGATACCGAGCTA
VGT1_MO17   (1313)  AGCAATTAACGTCAAATCCATCATCGTCATAAAACGACGATACCGAGCTA
VGT1_B73    (1500)  AGCAATTAACGTCAAATCCATCATCGTCATAAAACGACGATACCGAGCTA
Consensus   (1501)  AGCAATTAACGTCAAATCCATCATCGTCATAAAACGACGATACCGAGCTA
                          1551                                    1600
VGT1_C22    (1362)  GCGTTTAATTAGTTTGTTAGACGAACCAGAAACTATATTATATCGCTTTG
VGT1_MO17   (1363)  GCGTTTAATTAGTTTGTTAGACGAACCAGAAACTATATTATATCGCTTTG
VGT1_B73    (1550)  GCGTTTAATTAGTTTGTTAGACGAACCAGAAACTATATTATATCGCTTTG
Consensus   (1551)  GCGTTTAATTAGTTTGTTAGACGAACCAGAAACTATATTATATCGCTTTG
                          1601                                    1650
VGT1_C22    (1412)  TGTCCAAAAATTACTTATATTATATATAGTTCTCGTGCATCTACGTACAC
VGT1_MO17   (1413)  TGTCCAAAAATTACTTATATTATATATAGTTCTCGTGCATCTACGTACAC
VGT1_B73    (1600)  TGTCCAAAAATTACTTATATTATATATAGTTCTCGTGCATCTACGTACAC
Consensus   (1601)  TGTCCAAAAATTACTTATATTATATATAGTTCTCGTGCATCTACGTACAC
                          1651                                    1700
VGT1_C22    (1462)  GTAACATCGCTCTTAAATTTGTCCTTACTTGGTGTAAAAGATTAATCTA
VGT1_MO17   (1463)  GTAACATCGCTCTTAAATTTGTCCTTACTTGGTGTAAAAGATTAATCTA
VGT1_B73    (1650)  GTAACATCGCTCTTAAATTTGTCCTTACTTGGTGTAAAAGATTAATCTA
Consensus   (1651)  GTAACATCGCTCTTAAATTTGTCCTTACTTGGTGTAAAAGATTAATCTA
```

*FIG. 9C*

```
                       1701                                              1750
VGT1_C22    (1512) CAAAGACTATATTGTTAAAGCAAAATTGAGGAAGCTGTATTTAACCTCGT
VGT1_MO17   (1513) CAAAGACTATATTGTTAAAGCAAAATTGAGGAAGCTGTATTTAACCTCGT
VGT1_B73    (1700) CAAAGACTATATTGTTAAAGCAAAATTGAGGAAGCTGTATTTAACCTCGT
Consensus   (1701) CAAAGACTATATTGTTAAAGCAAAATTGAGGAAGCTGTATTTAACCTCGT
                       1751                                              1800
VGT1_C22    (1562) GACCACCTAAACTAGTGGGAATGCCCCATCCCTCAATAGAACTAGTTTTA
VGT1_MO17   (1563) GACCACCTAAACTAGTGGGAATGCCCCATCCCTCAATAGAACTAGTTTTA
VGT1_B73    (1750) GACCACCTAAACTAGTGGGAATTCCCCATCCCTCAATAGAACTAGTTTTA
Consensus   (1751) GACCACCTAAACTAGTGGGAATGCCCCATCCCTCAATAGAACTAGTTTTA
                       1801                                              1850
VGT1_C22    (1612) TTTGGCAAACATCATGGAAAGAATATATCAGATACACTACTCTCGCACAG
VGT1_MO17   (1613) TTTGGCAAACATCATGGAAAGAATATATCAGATACACTACTCTCGCACAG
VGT1_B73    (1800) TTTGGCAAACATCATGGAAAGAATATATCAGATACACTACTCTCGCACAG
Consensus   (1801) TTTGGCAAACATCATGGAAAGAATATATCAGATACACTACTCTCGCACAG
                       1851                                              1900
VGT1_C22    (1662) AGAGAGATGTCAAGTGGTTTGGGCATCAAAACCATAAGCGGACGGGTTTC
VGT1_MO17   (1663) AGAGAGATGTCAAGTGGTTTGGGCATCAAAACCATAAGCGGACGGGTTTC
VGT1_B73    (1850) AAAGAGACGTCAAGTGGTTTGGGCATCAAAACCATAAGCGGACGGGTTTC
Consensus   (1851) AGAGAGATGTCAAGTGGTTTGGGCATCAAAACCATAAGCGGACGGGTTTC
                       1901                                              1950
VGT1_C22    (1712) GAGTTTGGACCTTTGAATCTGGTTGATGTTGGAGCAAGAAGAAGCAAAAA
VGT1_MO17   (1713) GAGTTTGGACCTTTGAATCTGGTTGATGTTGGAGCAAGAAGAAGCAAAAA
VGT1_B73    (1900) GAGTTTGGACCTTTGAATCTGGTTGATGTTGGAGCAAGAAGAAGCAGAAA
Consensus   (1901) GAGTTTGGACCTTTGAATCTGGTTGATGTTGGAGCAAGAAGAAGCAAAAA
                       1951                                              2000
VGT1_C22    (1762) TGACACATGGCATCATTGTGAAGCTTGCGTCGAGACGAAGCAAGACAAAG
VGT1_MO17   (1763) TGACACATGGCATCATTGTGAAGCTTGCGTCGAGACGAAGCAAGACAAAG
VGT1_B73    (1950) TGACACATGGCATCATTGTGAAGCTTGCGTCGAGACGAAGCAAGACAAAG
Consensus   (1951) TGACACATGGCATCATTGTGAAGCTTGCGTCGAGACGAAGCAAGACAAAG
                       2001                                              2050
VGT1_C22    (1812) GCAAAGTAGCGAAGGTACACTGTTACCGCCGGCAATAACTACGTACGTAC
VGT1_MO17   (1813) GCAAAGTAGCGAAGGTACACTGTTACCGCCGGCAATAACTACGTACGTAC
VGT1_B73    (2000) GCAAAGTAGCGAAAGGTACACTGTTACCGCCGGCAATAACTACGTACGTAC
Consensus   (2001) GCAAAGTAGCGAAGGTACACTGTTACCGCCGGCAATAACTACGTACGTAC
                       2051                                              2100
VGT1_C22    (1862) ATGCATGTAAGACATGCATTGTACCGTGACATACATGTATGTCATATAAA
VGT1_MO17   (1863) ATGCATGTAAGACATGCATTGTACCGTGACATACATGTATGTCATATAAA
VGT1_B73    (2050) GTGCATGTAAGACATGCATTGTACCGTGACATACATGTATGTCATATAAA
Consensus   (2051) ATGCATGTAAGACATGCATTGTACCGTGACATACATGTATGTCATATAAA
                       2101                                              2150
VGT1_C22    (1912) TCTATGTAGATCACTCCTACGACCGGCGGCTAAT-TTCACTAC-ACACAT
VGT1_MO17   (1913) TCTATGTAGATCACTCCTACGACCGGCGGCTAAT-TTCACTAC-ACACAT
VGT1_B73    (2100) TCTATGTAGATCACTCCTACGACCGGCGGCTTATCGTCACTACAACGCAT
Consensus   (2101) TCTATGTAGATCACTCCTACGACCGGCGGCTAAT TTCACTAC ACACAT
                       2151                                              2200
VGT1_C22    (1960) GATGCATGGATGGAATGGATGTGAAGTGAGACTGTGAGAGCACTATCGGA
VGT1_MO17   (1961) GATGCATGGATGGAATGGATGTGAAGTGAGACTGTGAGAGCACTATCGGA
VGT1_B73    (2150) GATACATGGATGGAATGGATGTGAAGTGAGACTGTGAGAGCACTATCGGA
Consensus   (2151) GATGCATGGATGGAATGGATGTGAAGTGAGACTGTGAGAGCACTATCGGA
                       2201                                              2250
VGT1_C22    (2010) ATCACTTTCTTCGCCGAGTGTCGCTTTCCATGAATAAACATGTGAACCTA
VGT1_MO17   (2011) ATCACTTTCTTCGCCGAGTGTCGCTTTCCATGAATAAACATGTGAACCTA
VGT1_B73    (2200) ATCGCGTTCTTTGTCAAATGTCGCTTTCCATAAATAAACATGTGAACCTA
Consensus   (2201) ATCACTTTCTTCGCCGAGTGTCGCTTTCCATGAATAAACATGTGAACCTA
```

*FIG. 9D*

|            |        | 2251                                               2300 |
|------------|--------|----------------------------------------------------------|
| VGT1_C22   | (2060) | GGCCTAGGCACCTTCCACTTCAGGGCTTGTTCGGTTAGCTCTCAATCCAT |
| VGT1_MO17  | (2061) | GGCCTAGGCACCTTCCACTTCAGGGCTTGTTCGGTTAGCTCTCAATCCAT |
| VGT1_B73   | (2250) | GGCCTAGGCACCTTCCACTTCAGG-------------------------- |
| Consensus  | (2251) | GGCCTAGGCACCTTCCACTTCAGGGCTTGTTCGGTTAGCTCTCAATCCAT |
|            |        | 2301                                               2350 |
| VGT1_C22   | (2110) | GTGGATTGAGCGGGATTGGATGGGTTTGAATCCCAAACAAGTCAAACTTC |
| VGT1_MO17  | (2111) | GTGGATTGAGCGGGATTGGATGGGTTTGAATCCCAAACAAGTCAAACTTC |
| VGT1_B73   | (2274) | -------------------------------------------------- |
| Consensus  | (2301) | GTGGATTGAGCGGGATTGGATGGGTTTGAATCCCAAACAAGTCAAACTTC |
|            |        | 2351                                               2400 |
| VGT1_C22   | (2160) | TTCACAATTTTTTCCAATCCCATCCAATCCATGTGTATTGGGAATAACCG |
| VGT1_MO17  | (2161) | TTCACAATTTTTTCCAATCCCATCCAATCCATGTGTATTGGGAATAACCG |
| VGT1_B73   | (2274) | -------------------------------------------------- |
| Consensus  | (2351) | TTCACAATTTTTTCCAATCCCATCCAATCCATGTGTATTGGGAATAACCG |
|            |        | 2401                                               2450 |
| VGT1_C22   | (2210) | AACAAGCCCTCAGGCATCATCTTCTACAAATGTAGAATGTGTGAAGGTAG |
| VGT1_MO17  | (2211) | AACAAGCCCTCAGG---CATCTTCTACAAATGTAGAATGTGTGAAGGTAG |
| VGT1_B73   | (2274) | ----------------CATCTTCTACAAATGTAGAATGTGTGAAGGTAG |
| Consensus  | (2401) | AACAAGCCCTCAGG   CATCTTCTACAAATGTAGAATGTGTGAAGGTAG |
|            |        | 2451                                               2500 |
| VGT1_C22   | (2260) | GCAAACGTAAC-GGAAAGGCAGGAAGCTCATCGCCAACGCATCTCCTCTC |
| VGT1_MO17  | (2258) | GCAAACGTAAC-GGAAAGGCAGGAAGCTCATCGCCAACGCATCTCCTCTC |
| VGT1_B73   | (2307) | GCAAACGTAACGGGAAAGGCAGGAAGCTCATCGCCAACGCATCTCCTCTC |
| Consensus  | (2451) | GCAAACGTAAC GGAAAGGCAGGAAGCTCATCGCCAACGCATCTCCTCTC |
|            |        | 2501                                               2550 |
| VGT1_C22   | (2309) | CTGCTCCTTTTGACGACCTTTCATACCTGCACCCGCTTTTTCTGGAAAGG |
| VGT1_MO17  | (2307) | CTGCTCCTTTTGACGACCTTTCATACCTGCACCCGCTTTTTCTGGAAAGG |
| VGT1_B73   | (2357) | CTGCTCCTTTTGACGACCTTTCATACCTGCACCCGCTTTTTCTGGAAAGG |
| Consensus  | (2501) | CTGCTCCTTTTGACGACCTTTCATACCTGCACCCGCTTTTTCTGGAAAGG |
|            |        | 2551                                               2600 |
| VGT1_C22   | (2359) | GCATCAAGATT----TATATATATATATGTTATTCACCAGTAAATTTCAT |
| VGT1_MO17  | (2357) | GCATCAAGATTTATATATATATATATGTTATTCACCAGTAAATTTCAT |
| VGT1_B73   | (2407) | GCATCAAGATTTATATATATATGT---------------TATTTTTCAT |
| Consensus  | (2551) | GCATCAAGATTTATATATATATATATGTTATTCACCAGTAAATTTCAT |
|            |        | 2601                                               2650 |
| VGT1_C22   | (2405) | TATTATTAGCTTTGTTTACAACAAGTATTATTATTATTATCCGGGCTGTG |
| VGT1_MO17  | (2407) | TATTATTAGCTTTGTTTACAACAAGTATTATTATTATTATCCGGGCTGTG |
| VGT1_B73   | (2441) | TATTATTAGCTTTGTTTACAACAAGTATTATTATTATTATCCGGGCTGTG |
| Consensus  | (2601) | TATTATTAGCTTTGTTTACAACAAGTATTATTATTATTATCCGGGCTGTG |
|            |        | 2651                                               2700 |
| VGT1_C22   | (2455) | AGCAGAGGGAGCTGGTACAACTTGTCCCTTGAGACGGCCAAGAGGCAACA |
| VGT1_MO17  | (2457) | AGCAGAGGGAGCTGGTACAACTTGTCCCTTGAGACGGCCAAGAGGCAACA |
| VGT1_B73   | (2491) | AGCAGAGGGAGCTGGTACAACTTGTCCCTTGAGACGGCCAAGAGGCAACA |
| Consensus  | (2651) | AGCAGAGGGAGCTGGTACAACTTGTCCCTTGAGACGGCCAAGAGGCAACA |
|            |        | 2701                                               2750 |
| VGT1_C22   | (2505) | GTGTTGTGGGCTTGCGGCCATGACGCGACGTTGCTAGCTGCCGTGTCCAA |
| VGT1_MO17  | (2507) | GTGTTGTGGGCTTGCGGCCATGACGCGACGTTGCTAGCTGCCGTGTCCAA |
| VGT1_B73   | (2541) | GTGTTGTGGGCTTGCGGCCATGA--CGACGTTGCTAGCTGCCGTGTCCAA |
| Consensus  | (2701) | GTGTTGTGGGCTTGCGGCCATGACGCGACGTTGCTAGCTGCCGTGTCCAA |
|            |        | 2751                                               2800 |
| VGT1_C22   | (2555) | CAGGAAGAGAAGACGGCGACGTGGTCGCACTGTACGTTTTTCCCGCCACA |
| VGT1_MO17  | (2557) | CAGGAAGAGAAGACGGCGACGTGGTCGCACTGTACGTTTTTCCCGCCACA |
| VGT1_B73   | (2589) | CAGGAAGAGAAGACGGCGACGTGGTCGCACTGTACGTTTTTCCCGCCACA |
| Consensus  | (2751) | CAGGAAGAGAAGACGGCGACGTGGTCGCACTGTACGTTTTTCCCGCCACA |
|            |        | 2801                                               2850 |
| VGT1_C22   | (2605) | CAAACGGGGCGGGGGCGGTGGTATACTGGTATGGTGGCCACTGGCCAGC |
| VGT1_MO17  | (2607) | CAAACGGGGCGGGGGCGGGGGTATACTGGTATGGTGGCCACTGGCCAGC |
| VGT1_B73   | (2639) | CAAACGGGGCGGGGGCGGTGGTATACTGGTATGGTGGCCACTGGCCAGC |
| Consensus  | (2801) | CAAACGGGGCGGGGGCGGTGGTATACTGGTATGGTGGCCACTGGCCAGC |

FIG. 9E

|  |  | 2851 | 2900 |
|---|---|---|---|
| VGT1_C22 | (2655) | CGCCGTGCCGGTGCAGGCAGCAGCCCACAGGACCAACGCCGCCGCCAATG | |
| VGT1_MO17 | (2657) | CGCCGTGCCGGTGCAGGCAGCAGCCCACAGGACCAACGCCGCCGCCAATG | |
| VGT1_B73 | (2689) | CGCCGTGCCGGTGCAGGCAGCAGCCCACAGGACCAACGCCGCCGCCAATG | |
| Consensus | (2851) | CGCCGTGCCGGTGCAGGCAGCAGCCCACAGGACCAACGCCGCCGCCAATG | |
|  |  | 2901 | 2950 |
| VGT1_C22 | (2705) | GATCGGACGGCCTCTGCTACTGCTAGAAATGGAAAGCACGCAGGTACGTG | |
| VGT1_MO17 | (2707) | GATCGGACGGCCTCTGCTACTGCTAGAAATGGAAAGCACGCAGGTACGTG | |
| VGT1_B73 | (2739) | GATCGGACGGCCTCTGCTACTGCTAGAAATGGAAAGCACGCAGGTACGTG | |
| Consensus | (2901) | GATCGGACGGCCTCTGCTACTGCTAGAAATGGAAAGCACGCAGGTACGTG | |
|  |  | 2951 | 3000 |
| VGT1_C22 | (2755) | GGGCCCCCTCCCTTTCCCGCGCAAGTGCAGTGCCAGTGCGGCAGTGCGTG | |
| VGT1_MO17 | (2757) | GGGCCCCCTCCCTTTCCCGCGCAAGTGCAGTGCCAGTGCGGCAGTGCGTG | |
| VGT1_B73 | (2789) | GGGCCCCCTCCCTTTCCCGCGCAAGTGCAGTGCCAGTGCGGCAGTGCGTG | |
| Consensus | (2951) | GGGCCCCCTCCCTTTCCCGCGCAAGTGCAGTGCCAGTGCGGCAGTGCGTG | |
|  |  | 3001 | 3050 |
| VGT1_C22 | (2805) | TGTCATTATTCTGTCCGGACCGGTAGGTAGTAGTATCAGATGTACTACCA | |
| VGT1_MO17 | (2807) | TGTCATTATTCTGTCCGGACCGGTAGGTAGTAGTATCAGATGTACTACCA | |
| VGT1_B73 | (2839) | TGTCATTATTCTGTCCGGACCGGTAGGTAGTAGTATCAGATGTACTACCA | |
| Consensus | (3001) | TGTCATTATTCTGTCCGGACCGGTAGGTAGTAGTATCAGATGTACTACCA | |
|  |  | 3051 | 3100 |
| VGT1_C22 | (2855) | GTCAAACGACAGTGCCTTCCGCGGCGGCCAAAGGTACAGTGACACTTTGC | |
| VGT1_MO17 | (2857) | GTCAAACGACAGTGCCTTCCGCGGCGGCCAAAGGTACAGTGACACTTTGC | |
| VGT1_B73 | (2889) | GTCAAACGACAGTGCCTTCCGCGGCGGCCAAAGGTACAGTGACACTTTGC | |
| Consensus | (3051) | GTCAAACGACAGTGCCTTCCGCGGCGGCCAAAGGTACAGTGACACTTTGC | |
|  |  | 3101 | 3150 |
| VGT1_C22 | (2905) | CAAAAACAAAAAAAAAACAGCAAATAAAGAAAGGAACGCGCGCGGGAATA | |
| VGT1_MO17 | (2907) | CAAAAACAAAAAAAAAACAGCAAATAAAGAAAGGAACGCGCGCGGGAATA | |
| VGT1_B73 | (2939) | CAAAAACAAAAAAAAAACAGCAAATAAAGAAAGGAACGCGCGCGGGAATA | |
| Consensus | (3101) | CAAAAACAAAAAAAAAACAGCAAATAAAGAAAGGAACGCGCGCGGGAATA | |
|  |  | 3151 | 3200 |
| VGT1_C22 | (2955) | TATCGATCTCATCTTTTTTTTTCTTTTTTGTTGTTGTTGTCTACAGAGAT | |
| VGT1_MO17 | (2957) | TATCGATCTCATCTTTTTTTTTCTTTTTTGTTGTTGTTGTCTACAGAGAT | |
| VGT1_B73 | (2989) | TATCGATCTCATCTTTTTTTTTCTTTGTTGTTGTTGTCTACAGAGAT | |
| Consensus | (3151) | TATCGATCTCATCTTTTTTTTTCTTTTTTGTTGTTGTTGTCTACAGAGAT | |
|  |  | 3201 | 3250 |
| VGT1_C22 | (3005) | GGTAAGG-AATAAATAAATAAAGGTGCTAAATAAAGACCGGATTCTTTAT | |
| VGT1_MO17 | (3007) | GGTAAGG-AATAAATAAATAAAGGTGCTAAATAAAGACCGGATTCTTTAT | |
| VGT1_B73 | (3039) | GGTAAGGAAATAAATAAATAAAGGTGCTACATAAAGACCGGATTCTTTAT | |
| Consensus | (3201) | GGTAAGG AATAAATAAATAAAGGTGCTAAATAAAGACCGGATTCTTTAT | |
|  |  | 3251 | 3300 |
| VGT1_C22 | (3054) | TTCTTTCCAAATCCAGAAAAGGAATTATCTTCCCCGGAATCTATTTTCGA | |
| VGT1_MO17 | (3056) | TTCTTTCCAAATCCAGAAAAGGAATTATCTTCCCCGGAATCTATTTTCGA | |
| VGT1_B73 | (3089) | TTCTTTCCAAATCCAGAAAAGGAATTATCTTCCCCGGAATCTATTTTCGA | |
| Consensus | (3251) | TTCTTTCCAAATCCAGAAAAGGAATTATCTTCCCCGGAATCTATTTTCGA | |
|  |  | 3301 | 3350 |
| VGT1_C22 | (3104) | GCA---AATAATAATAATAATATATGATTTTGTTATTTTTCATTGGTTCT | |
| VGT1_MO17 | (3106) | GCAAATAATAATAATAATAATATATGATTTTGTTATTTTTCATTGGTTCT | |
| VGT1_B73 | (3139) | GCA---AATAATAATAATAATATATGATTTTGTTATTTTTCATTGGTTCT | |
| Consensus | (3301) | GCA    AATAATAATAATAATATATGATTTTGTTATTTTTCATTGGTTCT | |
|  |  | 3351 | 3400 |
| VGT1_C22 | (3151) | CTGGTTAATCATTTTGGACGTCATCTACCTAATAACATAGGTCGTCCACT | |
| VGT1_MO17 | (3156) | CTGGTTAATCATTTTGGACGTCATCTACCTAATAACATAGGTCGTCCACT | |
| VGT1_B73 | (3186) | CTGGTTAATCATTTTGGACGTCATCTACCTAATAACATAGGTCGTCCACT | |
| Consensus | (3351) | CTGGTTAATCATTTTGGACGTCATCTACCTAATAACATAGGTCGTCCACT | |

*FIG. 9F*

|  |  | 3401 | 3450 |
|---|---|---|---|
| VGT1_C22 | (3201) | ATGTGGAGCGCACGGCCTTAGCTTAAGACACAATTTGTTGACTTCCAGGA | |
| VGT1_MO17 | (3206) | ATGTGGAGCGCACGGCCTTAGCTTAAGACACAATTTGTTGACTTCCAGGA | |
| VGT1_B73 | (3236) | ATGTGGAGCGCACGGCCTTAGCTTAAGACACAATTTGTTGACTTCCAGGA | |
| Consensus | (3401) | ATGTGGAGCGCACGGCCTTAGCTTAAGACACAATTTGTTGACTTCCAGGA | |
|  |  | 3451 | 3500 |
| VGT1_C22 | (3251) | TTATATAATCCACCTTATAGATTATATAATCATATAATGATATCTAGTTA | |
| VGT1_MO17 | (3256) | TTATATAATCCACCTTATAGATTATATAATCATATAATGATATCTAGTTA | |
| VGT1_B73 | (3286) | TTATATAATCCACCTTATAGATTATATAATCATATAATGATATCTAGTTA | |
| Consensus | (3451) | TTATATAATCCACCTTATAGATTATATAATCATATAATGATATCTAGTTA | |
|  |  | 3501 | 3550 |
| VGT1_C22 | (3301) | TCAAGATTATATAATAATCCACCTAATAATTTGTGTTGTTTGTTTGCCTC | |
| VGT1_MO17 | (3306) | TCAAGATTATATAATAATCCACCTAATAATTTGTGTTGTTTGTTTGCCTC | |
| VGT1_B73 | (3336) | TCAAGATTATATAATAATCCACCTAATAATTTGTGTTGTTTGTTTGCCTC | |
| Consensus | (3501) | TCAAGATTATATAATAATCCACCTAATAATTTGTGTTGTTTGTTTGCCTC | |
|  |  | 3551 | 3600 |
| VGT1_C22 | (3351) | TTGATATAGTAGGACTATGTAGCCTACTGACATGATCAATTTACTTCTCT | |
| VGT1_MO17 | (3356) | TTGATATAGTAGGACTATGTAGCCTACTGACATGATCAATTTACTTCTCT | |
| VGT1_B73 | (3386) | TTGATATAGTAGGACTATGTAGCCTACTGACATGATCAATTTACTTCTCT | |
| Consensus | (3551) | TTGATATAGTAGGACTATGTAGCCTACTGACATGATCAATTTACTTCTCT | |
|  |  | 3601 | 3650 |
| VGT1_C22 | (3401) | AATCACCGGCAAAATGAAAAATCCATTGTTTACCTTGCCTTGAGTTGTAT | |
| VGT1_MO17 | (3406) | AATCACCGGCAAAATGAAAAATCCATTGTTTACCTTGCCTTGAGTTGTAT | |
| VGT1_B73 | (3436) | AATCACCGGCAAAATGAAAAATCCATTGTTTACCTTGCCTTGAGTTGTAT | |
| Consensus | (3601) | AATCACCGGCAAAATGAAAAATCCATTGTTTACCTTGCCTTGAGTTGTAT | |
|  |  | 3651 | 3700 |
| VGT1_C22 | (3451) | TAACGGTTTCCACCAAAGTCGTTCAAGACTCTAAGTAGCTCACATGTATT | |
| VGT1_MO17 | (3456) | TAACGGTTTCCACCAAAGTCGTTCAAGACTCTAAGTAGCTCACATGTATT | |
| VGT1_B73 | (3486) | TAACGGTTTCCACCAAAGTCGTTCAAGACTCTAAGTAGCTCACATGTATT | |
| Consensus | (3651) | TAACGGTTTCCACCAAAGTCGTTCAAGACTCTAAGTAGCTCACATGTATT | |
|  |  | 3701 | 3750 |
| VGT1_C22 | (3501) | CCATCCAGTCTTCAAATACTTTAAGGGGTCTTCACTTTGGATGTAAATAC | |
| VGT1_MO17 | (3506) | CCATCCAGTCTTCAAATACTTTAAGGGGTCTTCACTTTGGATGTAAATAC | |
| VGT1_B73 | (3536) | CCATCCAGTCTTCAAATACTTTAAGGGGTCTTCACTTTGGATGTAAATAC | |
| Consensus | (3701) | CCATCCAGTCTTCAAATACTTTAAGGGGTCTTCACTTTGGATGTAAATAC | |
|  |  | 3751 | 3800 |
| VGT1_C22 | (3551) | TTTATGTTTAAGCATTTGAAGCTCATTTTAGACTAGGATACCCTTGATCT | |
| VGT1_MO17 | (3556) | TTTATGTTTAAGCATTTGAAGCTCATTTTAGACTAGGATACCCTTGATCT | |
| VGT1_B73 | (3586) | TTTATGTTTAAGCATTTGAAGCTCATTTTAGACTAGGATACCCTTGATCT | |
| Consensus | (3751) | TTTATGTTTAAGCATTTGAAGCTCATTTTAGACTAGGATACCCTTGATCT | |
|  |  | 3801 | 3850 |
| VGT1_C22 | (3601) | AGGTGGTCCACATATTCTCCTAGGCATGACAAATTACTCAGAGACACGCT | |
| VGT1_MO17 | (3606) | AGGTGGTCCACATATTCTCCTAGGCATGACAAATTACTCAGAGACACGCT | |
| VGT1_B73 | (3636) | AGGTGGTCCACATATTCTCCTAGGCATGACAAATTACTCAGAGACACGCT | |
| Consensus | (3801) | AGGTGGTCCACATATTCTCCTAGGCATGACAAATTACTCAGAGACACGCT | |
|  |  | 3851 | 3900 |
| VGT1_C22 | (3651) | TCCTCTTCCCACTACATGTGTGCATGCATTGAAACCGTGAAAAAACCTAC | |
| VGT1_MO17 | (3656) | TCCTCTTCCCACTACATGTGTGCATGCATTGAAACCGTGAAAAAACCTAC | |
| VGT1_B73 | (3686) | TCCTCTTCCCACTACATGTGTGCATGCATTGAAACCGTGAAAAAACCTAC | |
| Consensus | (3851) | TCCTCTTCCCACTACATGTGTGCATGCATTGAAACCGTGAAAAAACCTAC | |
|  |  | 3901 | 3950 |
| VGT1_C22 | (3701) | GAGTGCAATCGATCAGGTCGGGAAAAAAGGCACACCTAGAGGCTAGAGC | |
| VGT1_MO17 | (3706) | GAGTGCAATCGATCAGGTCGGGAAAAAAGGCACACCTAGAGGCTAGAGC | |
| VGT1_B73 | (3736) | GAGTGCAATCGATCAGGTCGGGAAAAAAGGCACACCTAGAGGCTAGAGC | |
| Consensus | (3901) | GAGTGCAATCGATCAGGTCGGGAAAAAAGGCACACCTAGAGGCTAGAGC | |

*FIG. 9G*

|  |  | 3951 | 4000 |
|---|---|---|---|
| VGT1_C22 | (3751) | TCAGTCAGTCCCGAACGATTGC-AAAAAAAAAAGACACTAGAGCTCGACC | |
| VGT1_MO17 | (3756) | TCAGTCAGTCCCGAACGATTGCAAAAAAAAAAGACACTAGAGCTCGACC | |
| VGT1_B73 | (3786) | TCAGTCAGTCCCGAACGATTGCAAAAAAAAAAGACACTAGAGCTCGACC | |
| Consensus | (3951) | TCAGTCAGTCCCGAACGATTGCAAAAAAAAAAGACACTAGAGCTCGACC | |
|  |  | 4001 | 4050 |
| VGT1_C22 | (3800) | TCAAAACCCAGTGTGTCAATTTTTACAGCCAGCGTTGCAACCATCTAAGC | |
| VGT1_MO17 | (3806) | TCAAAACCCAGTGTGTCAATTTTTACAGCCAGCGTTGCAACCATCTAAGC | |
| VGT1_B73 | (3836) | TCAAAACCCAGTGTGTCAATTTTTACAGCCAGCGTTGCAACCATCTAAGC | |
| Consensus | (4001) | TCAAAACCCAGTGTGTCAATTTTTACAGCCAGCGTTGCAACCATCTAAGC | |
|  |  | 4051 | 4100 |
| VGT1_C22 | (3850) | TAACATCTTGTATTTAAATATTATAGAAACAACAACCCTATTTAATAGTT | |
| VGT1_MO17 | (3856) | TAACATCTTGTATTTAAATATTATAGAAACAACAACCCTATTTAATAGTT | |
| VGT1_B73 | (3886) | TAACATCTTGTATTTAAATATTATAGAAACAACAACCCTATTTAATAGTT | |
| Consensus | (4051) | TAACATCTTGTATTTAAATATTATAGAAACAACAACCCTATTTAATAGTT | |
|  |  | 4101 | 4150 |
| VGT1_C22 | (3900) | CCTTGGTATATATACAAGATCATGTCCAAAACATCAAGCATTTGAAGACT | |
| VGT1_MO17 | (3906) | CCTTGGTATATATACAAGATCATGTCCAAAACATCAAGCATTTGAAGACT | |
| VGT1_B73 | (3936) | CCTTGGTATATATACAAGATCATGTCCAAAACATCAAGCATTTGAAGACT | |
| Consensus | (4101) | CCTTGGTATATATACAAGATCATGTCCAAAACATCAAGCATTTGAAGACT | |
|  |  | 4151 | 4200 |
| VGT1_C22 | (3950) | AGATGTAGTACATGGACCAACCTGCAACCTTACTTTATCAGAGAAATCGT | |
| VGT1_MO17 | (3956) | AGATGTAGTACATGGACCAACCTGCAACCTTACTTTATCAGAGAAATCGT | |
| VGT1_B73 | (3986) | AGATGTAGTACATGGACCAACCTGCAACCTTACTTTATCAGAGAAATCGT | |
| Consensus | (4151) | AGATGTAGTACATGGACCAACCTGCAACCTTACTTTATCAGAGAAATCGT | |
|  |  | 4201 | 4250 |
| VGT1_C22 | (4000) | CAGTCCACACATATTTGTCATTAATTACCAAGGCACTACTGAGAGGTTAG | |
| VGT1_MO17 | (4006) | CAGTCCACACATATTTGTCATTAATTACCAAGGCACTACTGAGAGGTTAG | |
| VGT1_B73 | (4036) | CAGTCCACACATATTTGTCATTAATTACCAAGGCACTACTGAGAGGTTAG | |
| Consensus | (4201) | CAGTCCACACATATTTGTCATTAATTACCAAGGCACTACTGAGAGGTTAG | |
|  |  | 4251 | 4300 |
| VGT1_C22 | (4050) | ATGCCCACACCGTTTCACCAAATGATTGGTTAAAAAGCACGGACTCCTGT | |
| VGT1_MO17 | (4056) | ATGCCCACACCGTTTCACCAAATGATTGGTTAAAAAGCACGGACTCCTGT | |
| VGT1_B73 | (4086) | ATGCCCACACCGTTTCACCAAATGATTGGTTAAAAAGCACGGACTCCTGT | |
| Consensus | (4251) | ATGCCCACACCGTTTCACCAAATGATTGGTTAAAAAGCACGGACTCCTGT | |
|  |  | 4301 | 4350 |
| VGT1_C22 | (4100) | GGAGCTGCTACTCTGCAGAGGAGCGGGAGTCAGAACCATTTTTAGAAGAG | |
| VGT1_MO17 | (4106) | GGAGCTGCTACTCTGCAGAGGAGCGGGAGTCAGAACCATTTTTAGAAGAG | |
| VGT1_B73 | (4136) | GGAGCTGCTACTCTGCAGAGGAGCGGGAGTCAGAACCATTTTTAGAAGAG | |
| Consensus | (4301) | GGAGCTGCTACTCTGCAGAGGAGCGGGAGTCAGAACCATTTTTAGAAGAG | |
|  |  | 4351 | 4400 |
| VGT1_C22 | (4150) | CCAAAGTCCTACCAAACATACTCTTACTCTCTCTTTTTAAAGGTACTACC | |
| VGT1_MO17 | (4156) | CCAAAGTCCTACCAAACATACTCTTACTCTCTCTTTTTAAAGGTACTACC | |
| VGT1_B73 | (4186) | CCAAAGTCCTACCAAACATACTCTTACTCTCTCTTTTTAAAGGTACTACC | |
| Consensus | (4351) | CCAAAGTCCTACCAAACATACTCTTACTCTCTCTTTTTAAAGGTACTACC | |
|  |  | 4401 | 4450 |
| VGT1_C22 | (4200) | TCTTTTGAATTTAAATGTATTACTCCCTCTT------------------ | |
| VGT1_MO17 | (4206) | TCTTTTGAATTTAAATGTATTACTCCCTCTT------------------ | |
| VGT1_B73 | (4236) | TCTTTTGAATTTAAATGTATTACTCCCTCTTTAAAGAGATAATAGAGAAG | |
| Consensus | (4401) | TCTTTTGAATTTAAATGTATTACTCCCTCTT | |
|  |  | 4451 | 4479 |
| VGT1_C22 | (4231) | ----------------------------- | |
| VGT1_MO17 | (4237) | ----------------------------- | |
| VGT1_B73 | (4286) | ACGAACAAGAAAGGGAGAGGGAGAAACGA | |
| Consensus | (4451) | | |

FIG. 9H

SEQUENCE LISTING

```
<160> NUMBER OF SEQ ID NOS: 14

<210> SEQ ID NO 1
<211> LENGTH: 1371
<212> TYPE: DNA
<213> ORGANISM: Zea mays

<400> SEQUENCE: 1
atgcagttgg atctgaacgt ggccgaggcg ccgccgccgg tggagatgga ggcgagcgac      60
tcggggtcgt cggtgctgaa cgcgtcggaa gcggcgtcgg cgggcggcgc gcccgcgccg     120
gcggaggagg gatctagctc aacgccggcc gtgctggagt tcagcatcct catccggagc     180
gatagcgacg cggccggcgc ggacgaggac gaggacgcca cgccatcgcc tcctcctcgc     240
```

```
caccgccacc agcaccagca gcagctcgtg acccgcgagc tgttcccggc cggcgccggt    300
ccgccggccc cgacgccgcg gcattgggcc gagctcggct tcttccgcgc cgacctgcag    360
cagcaacagg cgccgggccc caggatcgtg ccgcacccac acgccgcgcc gccgccggcc    420
aagaagagcc gccgcggccc gcgctcccgc agctcgcagt accgcggcgt caccttctac    480
cgccgcacag gccgctggga gtcccacatc tgggattgcg gcaagcaggt gtacctaggt    540
ggattcgaca ccgctcacgc cgctgcaagg gcgtacgacc gggcggcgat caagttccgc    600
ggcgtcgacg ccgacatcaa cttcaacctc agcgactacg aggacgacat gaagcagatg    660
gggagcctgt ccaaggagga gttcgtgcac gtcctgcgcc gtcagagcac cggcttctcg    720
agaggcagct ccaggtacag aggcgtcacc ctgcacaagt gcggccgctg ggaggcgcgc    780
atggggcagt tcctcggcaa gaaagcttac gacaaggccg ccatcaaatg caatggcaga    840
gaggccgtga caaacttcga gccgagcacg tatcacgggg agctgccgac tgaagttgct    900
gatgtcgatc tgaacctgag catatctcag ccgagccccc aaagagacaa gaacagctgc    960
ctaggtctgc agctccacca cggaccattc gagggctccg aactgaagaa aaccaagatc   1020
gacgatgctc cctctgagct cccggggccgc cctcgtcggc tgtctcctgt cgtggctgag   1080
catccgccgg cctggcctgc gcagccgcct caccccttct tcgtcttcac aaaccatgag   1140
atgagtgcat caggagatct ccacaggagg cctgcagggg ctgttcccag ctgggcatgg   1200
caggtggcag cagcagctcc tcctcctgcc gccctgccgt cgtccgctgc agcatcatca   1260
ggattctcca acaccgccac gacagctgcc accgccgccc catcggcctc ctccctccgg   1320
tactgcccac cgccgccgcc gccgccgtcg agccatcacc atccccgctg a            1371
```

<210> SEQ ID NO 2
<211> LENGTH: 456
<212> TYPE: PRT
<213> ORGANISM: Zea mays

<400> SEQUENCE: 2

```
Met Gln Leu Asp Leu Asn Val Ala Glu Ala Pro Pro Val Glu Met
1               5                   10                  15

Glu Ala Ser Asp Ser Gly Ser Ser Val Leu Asn Ala Ser Glu Ala Ala
            20                  25                  30

Ser Ala Gly Gly Ala Pro Ala Pro Ala Glu Glu Gly Ser Ser Ser Thr
        35                  40                  45

Pro Ala Val Leu Glu Phe Ser Ile Leu Ile Arg Ser Asp Ser Asp Ala
    50                  55                  60

Ala Gly Ala Asp Glu Asp Glu Asp Ala Thr Pro Ser Pro Pro Pro Arg
65                  70                  75                  80

His Arg His Gln His Gln Gln Leu Val Thr Arg Glu Leu Phe Pro
                85                  90                  95

Ala Gly Ala Gly Pro Pro Ala Pro Thr Pro Arg His Trp Ala Glu Leu
            100                 105                 110

Gly Phe Phe Arg Ala Asp Leu Gln Gln Gln Ala Pro Gly Pro Arg
        115                 120                 125

Ile Val Pro His Pro His Ala Ala Pro Pro Ala Lys Lys Ser Arg
    130                 135                 140

Arg Gly Pro Arg Ser Arg Ser Ser Gln Tyr Arg Gly Val Thr Phe Tyr
145                 150                 155                 160

Arg Arg Thr Gly Arg Trp Glu Ser His Ile Trp Asp Cys Gly Lys Gln
                165                 170                 175
```

```
Val Tyr Leu Gly Gly Phe Asp Thr Ala His Ala Ala Arg Ala Tyr
            180                 185                 190
Asp Arg Ala Ala Ile Lys Phe Arg Gly Val Asp Ala Asp Ile Asn Phe
        195                 200                 205
Asn Leu Ser Asp Tyr Glu Asp Asp Met Lys Gln Met Gly Ser Leu Ser
    210                 215                 220
Lys Glu Glu Phe Val His Val Leu Arg Arg Gln Ser Thr Gly Phe Ser
225                 230                 235                 240
Arg Gly Ser Ser Arg Tyr Arg Gly Val Thr Leu His Lys Cys Gly Arg
                245                 250                 255
Trp Glu Ala Arg Met Gly Gln Phe Leu Gly Lys Lys Ala Tyr Asp Lys
            260                 265                 270
Ala Ala Ile Lys Cys Asn Gly Arg Glu Ala Val Thr Asn Phe Glu Pro
        275                 280                 285
Ser Thr Tyr His Gly Glu Leu Pro Thr Glu Val Ala Asp Val Asp Leu
    290                 295                 300
Asn Leu Ser Ile Ser Gln Pro Ser Pro Gln Arg Asp Lys Asn Ser Cys
305                 310                 315                 320
Leu Gly Leu Gln Leu His His Gly Pro Phe Glu Gly Ser Glu Leu Lys
                325                 330                 335
Lys Thr Lys Ile Asp Asp Ala Pro Ser Glu Leu Pro Gly Arg Pro Arg
            340                 345                 350
Arg Leu Ser Pro Val Val Ala Glu His Pro Ala Trp Pro Ala Gln
        355                 360                 365
Pro Pro His Pro Phe Phe Val Phe Thr Asn His Glu Met Ser Ala Ser
    370                 375                 380
Gly Asp Leu His Arg Arg Pro Ala Gly Ala Val Pro Ser Trp Ala Trp
385                 390                 395                 400
Gln Val Ala Ala Ala Pro Pro Ala Ala Leu Pro Ser Ser Ala
                405                 410                 415
Ala Ala Ser Ser Gly Phe Ser Asn Thr Ala Thr Ala Ala Thr Ala
            420                 425                 430
Ala Pro Ser Ala Ser Ser Leu Arg Tyr Cys Pro Pro Pro Pro Pro
        435                 440                 445
Pro Ser Ser His His His Pro Arg
    450                 455

<210> SEQ ID NO 3
<211> LENGTH: 7236
<212> TYPE: DNA
<213> ORGANISM: Zea mays

<400> SEQUENCE: 3
caagacttga gctcgaaaag tagcacagag agttcacaac tcgaacggag ctcaaatcac      60
taacacaatc gatcaaatgc gaggaggcgg agtgtgggag tcttagaatg cttagtggat     120
gcttagatgt ttcctccatg cgcctagagg tcccttttat agccccaaga cacctaagag     180
ccgttggaga tcaacatgga atgctatcct tgccttctgt cgagtggcgc accggacagg     240
tcctgtagat tgttcggtgc gcgatctcct tccaaatttg gcatatccga ccgttgctcc     300
tctgggctga ttggcgcacc ggacacagtc cggtgcacac cggacagtcc ggtgcaccag     360
ctgaccgttg gagcagtcca cgtgtcgcgc gaagattgcg tggccgaccg ttgctcaggc     420
gaccgttggc tcaccggaca gtccggtgca ccaccggaca gtccggtgaa ttatagtcgt     480
acgccgccgt cgaaacccga gagcggcgag ttcacagtgg accagcctgg cgcaccggac     540
```

```
actgtccggt gcaccattgg acattgtccg gtgcaccacc ggacagtccc gtgtgcgaga    600
ccgagcacaa gattggctgc acagagccaa gcttttccct ttttctccct tcttttttag    660
tcactgtttc tagcacttgg ataaccatgt tagtacataa acaattcac caagtctaga     720 aacatacctt ttgccttgat tttcacttct cactttattt ggcacataag aacttaatta    780
aacgtgttgg gcacttaatc accaaaacat tatagaaatg gcccaaaggc acatttccct    840
ttcagtaata agttaatacc tctttatatc attatttgaa cactgtgcaa tgatgttcat    900
ttatgtaatc gttgtgtacg tcagttctaa ttctagcacg tacatggttc acatccaatt    960
tgtcttctaa aaacgaatgt gacataatgt catatgtatg tgataatgct ttttgttggg   1020
gtccttcgtc tttcaaaggt cctcaaaaac acatttaacc attggttgtt agcacatcct   1080
taagtgttgc aggagctttg gtattgaata ccttcggagc aggacatgga ggaagacgaa   1140
gatgttagct tcgtcataac aacacaagga aacgaaggca gaagtggaac aaggccggga   1200
tatggtgttt tcaagactct gtatccaaag caaaaaagac agaaagacga tactgccctt   1260
acataatttg taaactatgt gaacaagttt tatggacatg tttgtaactt tacacgaaat   1320
tgtaccacca cactataaat agataaatag tgccctgcat gaggcgcctc ttgggaacaa   1380
tgaggaacaa ctctgtataa tccttttcct tctaagtacc ttcgggtttt ctcctcatca   1440
aaaagccgaa ggtactattg taaattcgtt tcatataaag aaagaaatcc caagttgttt   1500
gagataagta atcttatcta gctttgttat agccatgtgt gtaatcttta tctttatcct   1560
ctgacaatcc tatatattat atataataac cttcgtactt tacttggatg tcccgaagga   1620
caaactcttt aagtacgaag gataacatct ttttaataa tgtgttgcct tgttttttat    1680
tgtgtacaac aattaaaaac gagtgaccaa catttcatg tcagggtatg gggacccatt    1740
ggagactcga tatccaaatg aggatgagta tatgatgaat cctataccta tgatgagtat   1800
aagtatgaga atcaggatga gtataacttc atcagaatag gtgcgggggc gtccttgtgg   1860
gcgtgcctac cgtgcgatcg cacaaggcct ccaaaaccat agggcccaa aatttataac    1920 aatctttata tacaatataa ataaaaaata ttattttata taaatatttt accaacatat   1980
agcatagaat cgtaaaagcg ttgaaatcga tctgttctta ttgttattca aactatttac   2040
ctccagcaca ttgtagtcat tagataaaaa agattgagat cttattgtca ctatcttaag   2100
aagacacagt taaagaggt agacaatatg tcaaatatgct ttgatgcaag tgaccaattc   2160
gtgacgttga gtttcctcta agattttgtt taaaaaattg ctatgttgac attctaaatt   2220
ttataaagca gaggagcaaa actgagtaaa atcgcattta atgataaaaa tgtggaaagt   2280
gacaaaacta agaatacaat tttaaatagt ccaatatttt tttactatct tttgcacagg   2340
gcctctcaac ttgggaggac gcttctgggt gtgggtttac aaattcgatg aaaaattccc   2400
cattgacaaa cgataggagg atatttttct cccagcacaa aatagcatag ccataaggca   2460
acaaggcatg gcaaggatc gtatcatcgt catccgagac ccattgcttt ctctctctct   2520
cctcgtgctt tcattactgg ggtgggggtg gagtggacca gtggagtgga gaaatgacaa   2580
atccaggccc gcaggcagcc ccacccacca atcggccga gcagggtgcc caaatcagga   2640 aggatttta ggttaaccgg ctgccaccgc ccaccgccgg tgaccccagt ctctcttcta    2700
tctatatatt acccgcctcc ttttctcctc tctctccgcc ccaccctcct tcctcagctc   2760
cgttgcgcac cgccaccgcc ggccggccag ccgccggagc accgaaagac ccccgttctt   2820
tcctgtaaaa aaaaacccgc cgcctttagc tagctaaccg tcgtcctct tcaccccta    2880 gctttgctag ctctagctag gaacgaaaga aattaaagga taactgagat tgctgattgg   2940
```

```
tggtccgggt acggtgttct tgagtcgtga agcgacagta cagtggctag ggtcgtgccg   3000
cccctgcagt ctccggggtt gcgtgcagga tggtcgtcag ggatcgggag tgaggaggca   3060
tcagctctcg cggtcgtgga gcctaaatgt accgcaacaa cgactcggca ctctcctgct   3120
tctacctctt cctcctctgg ttcttcttct tgaagtagac accaccagtt cgccaggtag   3180
ttagcagccc agttgcgact ggggatcggt ggcgggctgc cgcttgcgag ttgtaagctt   3240
ggaggggagg ggagcaggag caggagatgc agttggatct gaacgtggcc gaggcgccgc   3300
cgccggtgga gatggaggcg agcgactcgg ggtcgtcggt gctgaacgcg tcggaagcgg   3360
cgtcggcggg cggcgcgccc gcgccggcgg aggagggatc tagctcaacg ccggccgtgc   3420
tggagttcag catcctcatc cggagcgata gcgacgcggc cggcgcggac gaggacgagg   3480
acgccacgcc atcgcctcct cctcgccacc gccaccagca ccagcagcag ctcgtgaccc   3540
gcgagctgtt cccggccggc gccggtccgc cggccccgac gccgcggcat tgggccgagc   3600
tcggcttctt ccgcgccgac ctgcagcagc aacaggcgcc gggccccagg atcgtgccgc   3660
acccacacgc cgcgccgccg ccggccaaga gagccgccg cggcccgcgc tcccgcagct   3720
cgcagtaccg cggcgtcacc ttctaccgcc gcacaggccg ctgggagtcc cacatctggt   3780
cagtactacc actgtctaca actagccaca ccacaccgat tgcttccgac tctcattaat   3840
ttctgacaca aactctccgt cttcctcctc ttctcccgcg acgcagggat tgcggcaagc   3900
aggtgtacct aggtgagcaa gagcagatct cttttgcgtt cccaaagatt tttcccttt   3960 tagttcctta tcccatccca tctcgaatgg cctagctaac cgattcagtg gtggtccggc   4020
tgctggccga tatacgcagg tggattcgac accgctcacg ccgctgcaag gcacgcactg   4080
gactggacgc ccagaattct tcgtcatgtg agtctctgac cgaattgatt gattaacgag   4140
tctctggctc ctggaactcg cagggcgtac gaccgggcgg cgatcaagtt ccgcggcgtc   4200
gacgccgaca tcaacttcaa cctcagcgac tacgaggacg acatgaagca gatggggagc   4260
ctgtccaagg aggagttcgt gcacgtcctg cgccgtcaga gcaccggctt ctcgagaggc   4320
agctccaggt acagaggcgt caccctgcac aagtgcggcc gctgggaggc gcgcatgggg   4380
cagttcctcg gcaagaagta agaaccaacc aacgcttctt ttcttttct ttttttata   4440 gcatgcagtg atgattcaac cttagttgtg cctttcctcc taatcctata tatgtaggat   4500
ttagtactgg ttgactatat aagtatatat gtattgttca gtaaaagtat acataggtta   4560
gctgcatgtt tatgtatgta gctggttgtt tcaatcagaa gataaaaaaa aagggaagta   4620
gtggctaggg aattcctcca atcctcaccg gtgggaacgc cgtgcttggg tgcaggtaca   4680
tataccttgg gctattcgac agcgaagtag aggctgcaag gttcttcatc ttggattctg   4740
ccgttcatat atgcataatc atgtcttta atttccaaag ggttgagtac cgactcgatt   4800
cctcttcgtg tctttttct ttctttcttc gaaatccaga gcctacgaca aggccgccat   4860
caaatgcaat ggcagagagg ccgtgacgaa cttcgagccg agcacgtatc acggggagct   4920
gccgactgaa ggtacgtatt ttcttctgc atatatatat cttcaggtat tattggctat   4980
taaactgctt ggatcttact gcttcttctg cagttgctga tgtcgatctg aacctgagca   5040
tatctcagcc gagccccaa agagacaaga acagctgcct aggtctgcag ctccaccacg   5100
gaccattcga gggctccgaa ctgaagaaaa ccaaggcaag cgctaacgat agatatacct   5160
tgacaagcta gtatcaaaca aaaccagtaa aaaaagttta ctttcttgtc gaatttcatt   5220
gcctacctga tgtacgtact tgtgcttctg cacaaaataa cgaaatcctt ttgccctctg   5280
atgatgatgc agatcgacga tgctccctct gagctaccgg gccgccctcg tcagctgtct   5340
```

```
cctctcgtgg ctgagcatcc gccggcctgg cctgcgcagc cgcctcaccc cttcttcgtc    5400
ttcacaaacc atgaggttag gtgacagcta ctgatcgaga tgcagcagca gttcaaacct    5460
gtctgttcca aggacccttta ggccggatta ccaaatcatc ggtcaactgt cctgtctgtt    5520
atatatttat gtgttaattt ataatacaag tgtgactatt tttcaaacct tccttcaaaa    5580
tgcatgaaaa gagttttttt taacgaaagg cgaaagaaa atatgatact tgggacagga     5640
gcaagcttgg atcatcagaa agtattatta attaggatca ctgagctgtt cattttgttc    5700
ttgagtcaat cctaatcgta ctatgtcagt gaatgaactt gtgttgcacc aatgcagatg    5760
agtgcatcag gagatctcca caggaggcct gcagggctg ttcccagctg gcatggcag     5820 gtggcagcag cagctcctcc tcctgccgcc ctgccgtcgt ccgctgcagc atcatcagga    5880
ttctccaaca ccgccacgac agctgccacc accgccccat cggcctcctc cctccggtac    5940
tgcccgccgc cgccgccgcc gtcgagccat caccatcccc gctgagagaa tcaagaagcc    6000
gcactgtaaa tctgccggga agctagcatt ttccccccgg cccctccccc tctccgggcg    6060
ttgcgacttt ttcagttttg cgccgccggc cggggtggtg gtttcttgta gccgatcgat    6120
tggattcctc gtattactgc tgcttacact cccaattaag tgaaaaaaaa acgtccctct    6180
actctttaca ctacacacac tgttagctga tcgattggac gtacttgcta gctgctgttg    6240
ctgctgctag cttgagattg actaacttca gcacttggat tgatctatat ctatatgact    6300
atatagacga cacattgtgt acgtgtagat aatatttctt cttttcctga ccgccataaa    6360
actgtttact ctggccattt tgaactaaag gctagctaca aatgagtgtc cttctcggcc    6420
ttctacatgt tctggtcatg gacatcgaga gatcaaactt ctctgtcctg cttactagat    6480
acgtactaga tttacttagc ctagatagat tccgttccaa actcgaggcc aggcgcatcg    6540
agatccgaga acttcatcca ctcgtcgctc atcatgctgc atgcatgatg gtctcaactc    6600
tgaggcatgc aaacgcagtg agacgaactg ggaggaattt atatagagta tatattgtcc    6660
ggcctgttgg tgataaagat agaatgcatg cacgctaact gccaacatgc atgggtgctg    6720
catcgaattt ttggtatggt gcatgcatac cgtgcattgg tgctctgcta gtactaggac    6780
caatctccat ggctccatta gatctcttgt ttactcgtct ccatgtgcct ctcaaagtgt    6840
gtactagcta gttgcggcac acaagttggc agttgtttgt tgtttcagcg gggaagaagg    6900
aggtcaccgt tgtcatcgtc aggggcgaag ctaggatcag aagacagagg gggcaggctt    6960
agcctccaag cgaccaaacc agtaagaaca caatataaaa atggcaagag aaccaaccat    7020
aatatatata ttgatatata atcttcatta aaaaacagta taatgaaaca acatctctttt   7080 tgtcaaacaa aataaaatta aatctcagtt attttgaatt tagctctacg tgtattagct    7140
agatcatagg tgaaagtcgc ctagagggg ggtgaatagg gcgaaactga aatttacaaa     7200
tataaacaca actacaagcc gggttagcgt tataag                              7236

<210> SEQ ID NO 4
<211> LENGTH: 7306
<212> TYPE: DNA
<213> ORGANISM: Zea mays

<400> SEQUENCE: 4
tagaatatat aatctagagc aaactagtta gtccaaatat ttgtgttggg aattcaacca      60
ccaaaattat ttataggaaa aggttaaacc ctatttccct ttcactaatt aattggaaga    120
acttgaggtg tagtcttctt cgtcgtcgtg ccgttaatgg ggtcctagca cagtacttgc    180
tctaccgagg ttgggtacca aggttctttt gttttgcttt tgttagacac cccatgtggg    240
```

```
gaggggtact atgtttatca aactgtagaa acctaacagg cgactttgac ctctggagaa    300
tctttgtaaa tgctacatag tgaaaccttg ttgactcacc ataggagtgt ttaagggttt    360
gatcgactta tggcaaaaag ggggtcacgg ctcgtgagta aagtgtaaga cctttgcata    420
gggttagaaa ctgatatatc agtcatgctc acaattaaga acggccttgg gagctccttt    480
gattagagat actgtagata cattcatgat gatggtttga tgatggtgcc tctaattatg    540
atttctagta ttttctctac gaggaggtac tattttggat aataagctag gttttaagat    600
aaaatttggc ttatattaat gattaaaacc tgataaagta aaagcaacct gctatcagct    660
taactccaca taaagctagt ccattttagc caaacaagat atttgctgag tacgttgatg    720
tgtgcaaaat ggagaacttt tatcttaaaa caccaggttg tccacactgc aaccactgct    780
caagcgagga tgaaggcaac atgaagaact ttcaggagtt tctagacttc aaggagtttt    840
aaactagatt agtggtaaac cccagtcagc tgcctgtgaa ggccttatct ttactacgtt    900
ccgcgttagc actttgttta cttgttaagt tgatggatac atcatgttgt aataagttaa    960
tacctcttta tatcattatt tgaacactgt gcaatgatgt tcatttatgt aatcgctgtg   1020
tatgtcagtt ctaattctag cacatacatg gttcacatcc agtttgtctt ctaaaaaacg   1080
aatgtgacat aatgtcatat gtatgtgata atgcttttg ttggggtcct tcgtctttca   1140
aaggtcctca aaaacacatt taaccattgg ttgttagcac atccttaagt gttgcaggag   1200
ctttggtatt gaataccttc ggagcaggac atggaggaag acgaagatgt tagcttcgtc   1260
ataacaacac aaggaaacga aggcagaagt ggaacaaggc cgggatatgg tgttttcaag   1320
actctgtaac caaagcaaaa aagacataaa gacgatactg tccttacata atttgtaaac   1380
tatatgaaca gttttatgg acatgtttgt aactttacac gaaactgtac caccacacta   1440
tagatagata aatagtgccc tgcatgaggc gcctcttggg aacaatgagg aacaactgtg   1500
tgtaatcctt tttcttctaa gtaccttcgg gttttctcct catcaaaaag cggaaggtac   1560
tattgtaaat ttgtttcata taagaaaga atcccaagt gtttgagat aagtaatctt   1620 atctagcttc gttatagccc tgtgtgtaat ctttatcttt atcctctgac aatcctatat   1680
attatatata ataaccttcg tactttactt ggatgtctcg aaggacaaac tctttaagta   1740
cgaaggataa catctttttt aataatatgt tgccttgttt ttttattgtg tacaacaatt   1800
aaaaacgagt gaccaacatt ttcatgtcgg ggtatggaga cccattggag actcctaaat   1860
gaggatgggt atatgatgaa tcctataccct atgatgagta taagtatgag aatcaggatg   1920
agtataactt catcagaaaa ggtacggggg cgtccttgtg ggcgtgccta cagtgcgatc   1980
gcacaaggcc tccaaaacca tagagcccca aaatttataa caatctttat atacaatata   2040
aataaaaaaa tattatttta tataaaatat ttaccaacat atagcataga atcgtaaaag   2100
cgttgaaatc gatatgttct tattgttatt caaactattt acctccagca tattgtagtc   2160
attagataaa aaagattgag atcttattgt cactatctta agacgacaca gttaaaagag   2220
gtagacaata tgatttgatg caagtaacca attcgtggcg ttgagtttcc tttaagattt   2280
tttaaaaaaa aattgctatg ttgacattct aaattttata aagcagagga gcaaaactga   2340
gtaaaatcgt aattaatgat aaaaatgcgg aaagtgacaa aactaagaat acaattttaa   2400
atagtccaat atctttttac tatctttttgc acagggcctc tcaacttggg aggacgcttc   2460
tgggtgtggg tttacaaatt cgatgaaaaa ttccccattg acaaacgata ggaggatatt   2520
tttctcccag cacaaaatag catagccata aggcaacaag gcatggcaaa ggatcgtatc   2580
atcgtcatcc gagacccatt gctttctctc tctctcctcg tgctttcatt actggggtgg   2640
```

```
gggtggagtg gaccagtgga gtggagaaat gacaaatcca ggcccgcagg cagccccacc    2700
caccaaatcg gccgagcagg gtgcccaaat caggaaggat tttaaggtta accggctgcc    2760
accgcccacc gccggtgacc ccagtctctc ttctatctat atattacccg cctccttttc    2820
tcctctctct ccgccccacc ctccttcctc agctccgttg cgcaccgcca ccgccggccg    2880
gccagccgcc ggagcaccga agaccccccg ttctttcctg taaaaaaaaa cccgccgcct    2940
ttagctagct aaccggtcgt cctcttcacc ccctagcttt gctagctcta gctaggaacg    3000
aaagaaatta aaggataact gagattgctg attggtggtc cgggtacggt gttcttgagt    3060
cgtgaagcga cagtacagtg gctagggtcg tgccgcccct gcagtctccg ggttgcgtg    3120 caggatggtc gtcagggatc aggagtgagg aggcatcagc tctcgcggtc gtggagccta    3180
aatgtaccgc aacaacgact cggcactctc ctgcttctac ctcttcctcc tctggttctt    3240
cttcttgaag tagacaccac cagttcgcca ggtagttagc agcccagttg cgactgggga    3300
tcggtggcgg gctgccgctt gcgagttgta agcttggagg ggaggggagc aggagcagga    3360
gatgcagctg gatctgaacg tggccgaggc gccgccgccg gtggagatgg aggcgagcga    3420
ctcggggtcg tcggtgctga acgcgtcgga agcggcgtcg gcgggcggcg cgcccgcgcc    3480
ggcggaggag gggtccagct caacgccggc cgcgctggag ttcagcatcc tcatccggag    3540
cgacagcgac gcggccggcg cggacgagga cgaggacgcc acgccgtcgc ctcctcctcg    3600
ccaccgccac cagcaccagc agcagctcgt gacccgcgag ctgttcccgg ctggcgccgg    3660
cccgccggcc ccggcgccgc ggcattgggc cgagctcggc ttcttccgcg ccgacctgca    3720
gcagcaacag gcgccgggcc ccaggatcgt gccgcaccca cacgccgcgc cgccgccggc    3780
caagaagagc cgccgcggcc cgcgctcccg cagctcgcag taccgcggcg tcaccttcta    3840
ccgccgcaca ggccgctggg agtcccacat ctggtcagta ctaccactgt ctacaactag    3900
ccacaccaca ccgattgctt ccgactctca ttaatttctg acacaaactc tccgtcttcc    3960
tcctcttctc ccgcgacgca gggattgcgg caagcaggtg tacctaggtg agcaagagca    4020
gatctctttt gcgttcccaa agattttccc cttttagctc ctcatcccat ctcgaatggc    4080
ctagctaacc gattcactgg tggtccggct gctggccgat atacgcaggt ggattcgaca    4140
ccgctcacgc cgctgcaagg cacgcactgg actggacgcc cagaattctt cgtcatgtga    4200
gtctctgacc ggattggttg attgattgat taacgagtct ctggctcctg gaactcgcag    4260
ggcgtacgac cgggcggcga tcaagttccg cggcgtggac gccgacatca acttcaacct    4320
cagcgactac gaggacgaca tgaagcagat ggggagcctg tccaaggagg agttcgtgca    4380
cgtcctgcgc cgccagagca ccggcttctc gagaggcagc tccaggtaca gaggcgtcac    4440
cctgcacaag tgcggccgct gggaggcgcg catgggcag ttcctcggca agaagtaaga    4500
accaaccaac gcttcttttt ttttatagca tgcagatgat gattcacact tagttgtgcc    4560
tctcctccta atcctatgta ggatttagta ttggttgact acatatctat tgttatatat    4620
gtattgttca gtaaaagtat acataggtta gctgcatgtt tatgtatgta gctggttgtt    4680
tcaatcagaa gataaaaaga aagggaagta gtggctaggg aattcctcca atcctcaccg    4740
gtgggaacgc cgtgcttggg tgcaggtaca tataccttgg gctattcgac agcgaagtag    4800
aggctgcaag gttcttcatc ttggattctg ccgttcatat atgcataacc atgtctttc    4860 atttccaaag ggttgagtac cgactcgatt cctctttttt tttctttctt tcttcgaaat    4920
ccagagctta cgacaaggcc gccatcaaat gcaatggcag agaggccgtg acgaacttcg    4980
agccgagcac gtatcacggg gagctgccga ctgaaggtac gtatttcttt ctgcatatat    5040
```

```
ataatcttca ggtattattg gctattaaac tgcttggatt ttactgcttc ttctgcagtt    5100
gctgatgtcg atctgaacct gagcatatct cagccgagcc cccaaagaga caagaacagc    5160
tgcctaggtc tgcagctcca ccacggacca ttcgagggct ccgaactgaa gaaaaccaag    5220
gcaagcgcta acgatagata taccttgaca agctagtatc aaacaaaacc agtattttt    5280 ttactttctt gtcgaatttc attgcctacc tgatgtacgt acttgtgctt ctgcacagaa    5340
taacgaaatc cttttgccct ctgatgatga tgcagatcga cgatgctccc tctgacctcc    5400
cgggccgccc tcgtcggctg tctcctctcg tggctgagca tccgccggcc tggcctgcgc    5460
agccgcctca ccccttcttc gtcttcacaa accatgaggt taggtgacag ctactgatcg    5520
agatgcagca gcagttcaaa acttagatcc ggtcccttgt cctgtctgtt ccaaggacct    5580
ttaggccgga ttaccaaatc atcggtcaac tgtcctgtct gttatatatt tatgtgttta    5640
taatacaagt gtgactattt ttcaaacctt ccttcaaaat gcatgaaaag agtttttttt    5700
ttaacgaaag gcgaaaagaa aatatgatac tttgggacag gagcaagctt ggatcatcag    5760
aaagtattat taattaggat cactgagctg ttcatttgt tcttgaatca atcctaatcg    5820
tactatgtca gtgaatgaac ttgtgttgca ccaatgcaga tgagtgcatc aggagatctc    5880
cacaggaggc ctgcagggc tgttcccagc tgggcatggc aggtggcagc agcagctcct    5940
cctcctgccg ccctgccgtc gtccgctgca gcatcatcag gattctccaa caccgccacg    6000
acagctgcca ccgccgcccc atcggcctcc tccctccggt actgcccgcc gccgccgccg    6060
ccgccgtcga gccatcacca tcgccgctga gagaatcaag aagccgcact gtaaatctgc    6120
cgggaatgaa gctagcattt tccccccggc cctcccctct ccgggcgttg cgacttttc    6180 agttttgcgc cgccagccgg ggtggtggtt tcttgtaacc gatcggttgg attcctcgta    6240
ttactgctta cactcccaat taagtgggaa aaaacgctcc tctactcttt acactagaca    6300
cactgttagc tgatcgattg gacgtacttg ctagctgctg ttgctgctgc tagctagaga    6360
ttgactaact gaagcacttg gattgatcta tatctatatg actatataga cacattgtgt    6420
acgtgtagat aatatttctt tatttcctga ccgccataaa actgtttact ctagccattt    6480
tgaactaaag gctagctaca aatgagtgtc cgtctcggcc ttctacatgt tctggtcatg    6540
gacatcgaga gatcaaactt ctctgtcctg cttactagat acgtactaga tttacttagc    6600
ctagatagat ttcgttccaa actcgaggcc aggcgcatcg agatccgagc acttcatcca    6660
ctcgtcgttc atcgtgctgc atgcatgatg gtctcaactc tgaggcatgc aaacgcagtg    6720
agaacgaact gggaggaatt tatatagagt atatattgtc cggcctgttg gtgataaaga    6780
tagaatgcat gcacgctaac tgccaacatg catgggtgct gcatcgaatt tttggtatgg    6840
tgcggtgcat gcataccgtg cattggtggg gagaatccat gaaatagcac ttgtttgaga    6900
cggcgttcac gaaatagcat ccgatttcaa gtaattcata aatagcact tgttttacca     6960 aattaattca gaaataaaca ctctatctat attttgcatt cttttattgc ttacctcaca    7020
tacaaatgga ccaaattacc cctatttatc acaaccttct tttttatct cttatgtcca     7080 taagaacaac ataataaat aaatatatg acctatattt ttatagtgtt aaacatacaa      7140
atagacacat gttttatgaa cgaagaagtc tatatttaac tattaaattt agaactaggt    7200
atcttcggtt gtcgaacttt taaaattaga catatttggt ccattaaaag gtcttagatt    7260
gtacttccta tgttctttt tatttgatac ggttgttttt tttcaa                    7306
```

```
<210> SEQ ID NO 5
<211> LENGTH: 4230
<212> TYPE: DNA
<213> ORGANISM: Zea mays

<400> SEQUENCE: 5
ctccacctct ctcgtacgct ttgattggcc gctcgcacgc atttatcgcc aagatcgggc      60
ttgcccatca ctgggatcat cctggctggc tggctggccg gccacatatc aaacatggat     120
ttgctatatt ttaaatgcct gaaatatgtt atactatgtt ttttagataa cgatctttac     180
agtcgattta tgaatgtgta gaattaagat tgagcttcct gatgaaaaaa tcaggcaaga     240
ggctcttttg gttggagacc tggcatggca cttgcctgcg agtcaagcaa accctatgcc     300
actgtttgga ccaggccact ttcctagaga gccgaatcag acatcactat cggaattcga     360
atgagtgctc agcactttac cgagtgcaat taatcggaca ctcggcaaag cattctttgt     420
cgagtgccac tctcggcgaa ctaataaggc tctcgggaca gatctcgtat gtcgagagcg     480
gaacactcga catagaaaaa cactcggcaa agaggttttt gtcgaatgac aagctctcgg     540
caaaatgtga cactcgataa gggtcgtcaa gagtcgtcta tgttgacgg ccattaactt      600 tcccgagtgt caaacgttga cacttgggaa ttatcttctt tttgtcgatt gtaacctggc     660
aaaccctcgg caaaagtata ctttgcggag tgtcttccct caacactcga taaagaatat     720
ttgtttcttt ttctttttc tataccaaac tctttgtgac gttttttctg cagtatatag      780
acatacatat tcaattttac acaattatca aagtgtttgc tataattaat agatttagtt     840
tgtttaattg aatttctgag aaccaatcaa atagacccga attagacata tctagacatt     900 taaaagtaa gatactaaaa aataatagtg tttaccttca accggtacta aatgtcattc      960
ctgtagtaga caggataacg aaagctagtc tatttagatc atcagttcca gttcgagatt    1020
ttaaatgcta gtccctccat ttcaatttac aatttattta attttttag tgtgataccg     1080 tttagcgtat gtagctttga ttttttata tattttgca aaattttgaa taagacaagt      1140
gtgtcaaatt tggtgtaaaa attaaacgaa attataaatt ggagcggagg gagtagaaat    1200
ctacgatttt tctagctgag gcagactgtg cgcattccca tccatcgagt ccacttgcac    1260
ctctcctcga catgaatacg aatgtacgat ccgatgaatt ccccacaaag aagcaattaa    1320
cgtcaaatcc atcatcgtca taaaacgacg ataccgagct agcgtttaat tagtttgtta    1380
gacgaaccag aaactatatt atatcgcttt gtgtccaaaa attacttata ttatatatag    1440
ttctcgtgca tctacgtaca cgtaacatcg ctcttaaatt tgtccttact tggtgtaaaa    1500
agattaatct acaaagacta tattgttaaa gcaaaattga ggaagctgta tttaacctcg    1560
tgaccaccta aactagtggg aatgccccat ccctcaatag aactagtttt atttggcaaa    1620
catcatggaa agaatatatc agatacacta ctctcgcaca gagagagatg tcaagtggtt    1680
tgggcatcaa aaccataagc ggacggggttt cgagtttgga cctttgaatc tggttgatgt    1740
tggagcaaga agaagcaaaa atgacacatg gcatcattgt gaagcttgcg tcgagacgaa    1800
gcaagacaaa ggcaaagtag cgaaggtaca ctgttaccgc cggcaataac tacgtacgta    1860
catgcatgta agacatgcat tgtaccgtga catacatgta tgtcatataa atctatgtag    1920
atcactccta cgaccggcgg ctaatttcac tacacacatg atgcatggat ggaatggatg    1980
tgaagtgaga ctgtgagagc actatcggaa tcactttctt cgccgagtgt cgcttttcat    2040
gaataaacat gtgaacctag gcctaggcac cttccacttc agggcttgtt cggttagctc    2100
tcaatccatg tggattgagc gggattggat gggtttgaat cccaaacaag tcaaacttct    2160
tcacaatttt ttccaatccc atccaatcca tgtgtattgg gaataaccga acaagccctc    2220
```

```
aggcatcatc ttctacaaat gtagaatgtg tgaaggtagg caaacgtaac ggaaaggcag      2280
gaagctcatc gccaacgcat ctcctctcct gctccttttg acgacctttc atacctgcac      2340 ccgcttttc tggaaagggc atcaagattt atatatatat atgttattca ccagtaaatt       2400
tcattattat tagctttgtt tacaacaagt attattatta ttatccgggc tgtgagcaga      2460
gggagctggt acaacttgtc ccttgagacg gccaagaggc aacagtgttg tgggcttgcg      2520
gccatgacgc gacgttgcta gctgccgtgt ccaacaggaa gagaagacgg cgacgtggtc      2580
gcactgtacg ttttccccgc cacacaaacg gggcggggg cggtggtata ctggtatggt       2640
ggccactggc cagccgccgt gccggtgcag gcagcagccc acaggaccaa cgccgccgcc      2700
aatggatcgg acggcctctg ctactgctag aaatggaaag cacgcaggta cgtggggccc      2760
cctccctttc ccgcgcaagt gcagtgccag tgcggcagtg cgtgtgtcat tattctgtcc      2820
ggaccggtag gtagtagtat cagatgtact accagtcaaa cgacagtgcc ttccgcggcg      2880
gccaaaggta cagtgacact ttgccaaaaa caaaaaaaaa acagcaaata aagaaaggaa      2940
cgcgcgcggg aatatatcga tctcatcttt ttttttcttt tttgttgttg ttgtctacag      3000
agatggtaag gaataaataa ataaaggtgc taaataaaga ccggattctt tatttctttc      3060
caaatccaga aaaggaatta tcttccccgg aatctatttt cgagcaaata ataataataa      3120
tatatgattt tgttattttt cattggttct ctggttaatc attttggacg tcatctacct      3180
aataacatag gtcgtccact atgtggagcg cacggcctta gcttaagaca caatttgttg      3240
acttccagga ttataatc cccttatag attatataat catataatga tatctagtta        3300
tcaagattat ataataatcc acctaataat ttgtgttgtt tgtttgcctc ttgatatagt      3360
aggactatgt agcctactga catgatcaat ttacttctct aatcaccggc aaaatgaaaa      3420
atccattgtt taccttgcct tgagttgtat aacggttttc caccaaagtc gttcaagact      3480
ctaagtagct cacatgtatt ccatccagtc ttcaaatact ttaagggtc ttcactttgg       3540 atgtaaatac tttatgttta agcatttgaa gctcattta gactaggata cccttgatct       3600
aggtggtcca catattctcc taggcatgac aaattactca gagacacgct tcctcttccc      3660
actacatgtg tgcatgcatt gaaaccgtga aaaacctac gagtgcaatc gatcaggtcg       3720 ggaaaaaag gcacacctag aggctagagc tcagtcagtc ccgaacgatt gcaaaaaaa       3780 aagcacactag agctcgacct caaaacccag tgtgtcaatt tttacagcca gcgttgcaac     3840
catctaagct aacatcttgt atttaaatat tatagaaaca acaccctat ttaatagttc       3900 cttggtatat atacaagatc atgtccaaaa catcaagcat ttgaagacta gatgtagtac      3960
atggaccaac ctgcaacctt actttatcag agaaatcgtc agtccacaca tatttgtcat      4020
taattaccaa ggcactactg agaggttaga tgcccacacc gtttcaccaa atgattggtt      4080
aaaaagcacg gactcctgtg gagctgctac tctgcagagg agcgggagtc agaaccattt      4140
ttagaagagc caaagtccta ccaaacatac tcttactctc tcttttaaa ggtactacct      4200 cttttgaatt taaatgtatt actccctctt                                       4230

<210> SEQ ID NO 6
<211> LENGTH: 4236
<212> TYPE: DNA
<213> ORGANISM: Zea mays

<400> SEQUENCE: 6
ctccacctct ctcgtacgct ttgattggcc gctcgcacgc atttatcgcc aagatcgggc        60
ttgcccatca ctgggatcat cctggctggc tggctggccg gccacatatc aaacatggat      120
```

-continued

```
ttgctatatt ttaaatgcct gaaatatgtt atactatgtt ttttagataa cgatctttac    180
agtcgattta tgaatgtgta gaattaagat tgagcttcct gatgaaaaaa tcaggcaaga    240
ggctcttttg gttggagacc tggcatggca cttgcctgcg agtcaagcaa accctatgcc    300
actgtttgga ccaggccact ttcctagaga gccgaatcag acatcactat cggaattcga    360
atgagtgctc agcactttac cgagtgcaat taatcggaca ctcggcaaag cattctttgt    420
cgagtgccac tctcggcgaa ctaataaggc tctcgggaca gatctcgtat gtcgagagcg    480
gaacactcga catagaaaaa cactcggcaa agaggttttt gccgaatgcc aagctctcgg    540
caaaatgcga cactcggtaa gggtcgtcaa gagtcgtcta ttgttgacgg ccattaactt    600
tcccgagtgt caaacgttga cacttgggaa ttatcttctt tttgtcgagt gtaacctggc    660
aaaccctcgg caaaaatata ctttgcggag tgtcttccct cgacactcga taagaaatat    720
ttgtttcttt ttctttttttc tataccaaac tctttgtgac gttttttctg cagtatatag    780
acatacatat tcaattttac acaattatca aagtgtttgc tataattaat agatttagtt    840
tgtttaattg aatttctgag aaccaaccaa atagacccga attagacata tctagacatt    900
taaaagtaa gatactaaaa aataatagtg tttaccttca accggtacta aatatcattc    960
ctgtagtaga caggataacg aaagctagtc tatttagatc atcagttcca gttcgagatt   1020
ttaaatgcta gtccctccat ttcaatttac aattttattta attttttttag tgtgataccg   1080
tttagcgtat gtagctttga tttttttttat atatttttgc aaaattttga ataagacaag   1140
tgtgtcaaat ttggtgtaaa aattaaacga aattataaat tggagcggag ggagtagaaa   1200
tctacgattt ttctagctga ggcagactgt gcgcattccc atccatcgag tccacttgca   1260
cctctcctcg acatgaatac gaatgtacga tccgatgaat tccccacaaa gaagcaatta   1320
acgtcaaatc catcatcgtc ataaaacgac gataccgagc tagcgtttaa ttagtttgtt   1380
agacgaacca gaaactatat tatatcgctt tgtgtccaaa aattacttat attatatata   1440
gttctcgtgc atctacgtac acgtaacatc gctcttaaat ttgtccttac ttggtgtaaa   1500
aagattaatc tacaaagact atattgttaa agcaaaattg aggaagctgt atttaacctc   1560
gtgaccacct aaactagtgg gaatgcccca tccctcaata gaactagttt tatttggcaa   1620
acatcatgga aagaatatat cagatacact actctcgcac agagagagat gtcaagtggt   1680
ttgggcatca aaaccataag cggacggggtt tcgagtttgg acctttgaat ctggttgatg   1740
ttggagcaag aagaagcaaa aatgacacat ggcatcattg tgaagcttgc gtcgagacga   1800
agcaagacaa aggcaaagta gcgaaggtac actgttaccg ccggcaataa ctacgtacgt   1860
acatgcatgt aagacatgca ttgtaccgtg acatacatgt atgtcatata aatctatgta   1920
gatcactcct acgaccggcg gctaatttca ctacacacat gatgcatgga tggaatggat   1980
gtgaagtgag actgtgagag cactatcgga atcactttct tcgccgagtg tcgcttttcca   2040
tgaataaaca tgtgaaccta ggcctaggca ccttccactt cagggcttgt tcggttagct   2100
ctcaatccat gtggattgag cgggattgga tgggtttgaa tcccaaacaa gtcaaacttc   2160
ttcacaattt tttccaatcc catccaatcc atgtgtattg gaataaccg aacaagccct   2220
caggcatctt ctacaaatgt agaatgtgtg aaggtaggca aacgtaacgg aaaggcagga   2280
agctcatcgc caacgcatct cctctcctgc tccttttgac gacctttcat acctgcaccc   2340
gcttttctg gaaagggcat caagatttat atatatatat atatgttatt caccagtaaa   2400
tttcattatt attagctttg tttacaacaa gtattattat tattatccgg gctgtgagca   2460
gagggagctg gtacaacttg tcccttgaga cggccaagag gcaacagtgt tgtgggcttg   2520
```

```
cggccatgac gcgacgttgc tagctgccgt gtccaacagg aagagaagac ggcgacgtgg    2580
tcgcactgta cgttttctcc gccacacaaa cggggcgggg ggcggggta  tactggtatg    2640 gtggccactg gccagccgcc gtgccggtgc aggcagcagc ccacaggacc aacgccgccg    2700
ccaatggatc ggacggcctc tgctactgct agaaatggaa agcacgcagg tacgtggggc    2760 cccctcccctt tcccgcgcaa gtgcagtgcc agtgcggcag tgcgtgtgtc attattctgt    2820
ccggaccggt aggtagtagt atcagatgta ctaccagtca aacgacagtg ccttccgcgg    2880
cggccaaagg tacagtgaca ctttgccaaa acaaaaaaa  aaacagcaaa taagaaagg     2940 aacgcgcgcg ggaatatatc gatctcatct ttttttttct tttttgttgt tgttgtctac    3000
agagatggta aggaataaat aaataaaggt gctaaataaa gaccggattc tttatttctt    3060
tccaaatcca gaaaggaat  tatcttcccc ggaatctatt ttcgagcaaa taataataat    3120
aataatatat gattttgtta ttttcattg  gttctctggt taatcatttt ggacgtcatc    3180
tacctaataa cataggtcgt ccactatgtg gagcgcacgg ccttagctta agacacaatt    3240
tgttgacttc caggattata taatccacct tatagattat ataatcatat aatgatatct    3300
agttatcaag attatataat aatccaccta ataatttgtg ttgtttgttt gcctcttgat    3360
atagtaggac tatgtagcct actgacatga tcaatttact tctctaatca ccggcaaaat    3420 gaaaatcca  ttgtttacct tgccttgagt tgtattaacg gtttccacca agtcgttca     3480 agactctaag tagctcacat gtattccatc cagtcttcaa atactttaag gggtcttcac    3540
tttggatgta aatactttat gtttaagcat ttgaagctca ttttagacta ggataccctt    3600
gatctaggtg gtccacatat tctcctaggc atgacaaatt actcagagac acgcttcctc    3660
ttcccactac atgtgtgcat gcattgaaac cgtgaaaaaa cctacgagtg caatcgatca    3720
ggtcgggaaa aaaaggcaca cctagaggct agagctcagt cagtcccgaa cgattgcaaa    3780 aaaaaaaga  cactagagct cgacctcaaa acccagtgtg tcaattttta cagccagcgt    3840
tgcaaccatc taagctaaca tcttgtattt aaatattata gaaacaacaa ccctatttaa    3900
tagttccttg gtatatatac aagatcatgt ccaaaacatc aagcatttga agactagatg    3960
tagtacatgg accaacctgc aaccttactt tatcagaaaa atcgtcagtc cacacatatt    4020
tgtcattaat taccaaggca ctactgagag gttagatgcc cacaccgttt caccaaatga    4080
ttggttaaaa agcacggact cctgtgggagc tgctactctg cagaggagcg ggagtcagaa    4140
ccatttttag aagagccaaa gtcctaccaa acatactctt actctctctt tttaaaggta    4200
ctacctcttt tgaatttaaa tgtattactc cctctt                              4236

<210> SEQ ID NO 7
<211> LENGTH: 4313
<212> TYPE: DNA
<213> ORGANISM: Zea mays

<400> SEQUENCE: 7
ataaatttat tttgaagata taaatatttt aacggtattt tttattaata aaatgattta     60
tatggattat acagatagag tctctctcta ctctctagtc ctgtgtacgt gcaggtttgg    120
caaggtatga acaggacgtc aaacgcgtac gtgtactcca cacacactcc acctctctcg    180
tacgctttga ttggccgctc gcacgcattt atcgccaaga tcgggcttgc ccatcactgg    240
gatcatcctg gctggctggc tggccggcca catatcaaac atggatttgc tcatttgcta    300
tattttaaat gcctgaaata tgttatacta tgttttttag ataacgatct ttacagtcga    360
tttatgaatg tgtagaatta agattgagct tcctgatgaa aaaatcaggc aagaggctct    420
```

```
tttggttgga gacctggcat ggcacttgcc tgcgagtcaa gcaaaccta tgccactgtt      480 tggaccaagc cactttccta gagagccgaa tcagacatca ctatcggaat tcgaatgagt     540
gctcagcact ttaccgagtg taattaatcg dacactcggc aaagcattct ttgtcgagtg     600
tcactctcgg cgaactaata aggctctcgg dacagatctc gtatgtcgag agcggaacac    660
tcgacataga aaaacactcg gcaaaagagg ttttaccgaa tgccaagctc tcggcaaaat     720
gcgacactcg gtaagggtcg tcaagagtcg tctattgttg acggccatta actttcccga    780
gtgtcaaacg ttgacacttg ggaattatct tcttttttgtc gattgtaacc tggcaaaccc   840
tcggcaaaag tatactttac ggagtgtctt ccctcaacac tcgataaaga atatttgttt    900
cttttctttt tttctatacc aaactctttg tgacgttttt tctgcagtat atagacatac    960
atattcaatt ttacacaatt atcaaagtgt ttgctataat taatagattt agtttgttta   1020
attgaatttc tgagaaccaa ccaaatagac ccgaattaga catatctaga catttaaaaa    1080
gtaagatact aaaaaataat agtgtttacc ttcaaccggt actaaatatc attcctgtag    1140
tagacaggat aacgaaagct agtctattta gatcatcagt tccagttcga gatttttaaat   1200 gctagtccct ccatttcaat ttacaattta tttaattttt ttagtgtgat accgtttagc    1260
atataatata cttttaagtgt agctttgatt tttttatata ttttttgcaaa attttgaata  1320 agacaagtat gtcaaattg gtgtaaaaat taaacgaatt tataaattgg agcggaggga    1380
gtagaaatct acgattttc tagctgaggc agactgtgcg cattcccatc catcgagtcc    1440 acttgcaccct ctcctcgaca tgaatacgaa tgtacgatcc gatgaattcc ccacaaagaa   1500
gcaattaacg tcaaatccat catcgtcata aaacgacgat accgagctag cgtttaatta   1560
gtttgttaga cgaaccagaa actatattat atcgctttgt gtccaaaaat tacttatatt    1620
atatatagtt ctcgtgcatc tacgtacacg taacatcgct cttaaatttg tccttacttg    1680
gtgtaaaaag attaatctac aaagactata ttgttaaagc aaaattgagg aagctgtatt    1740
taacctcgtg accacctaaa ctagtgggaa ttccccatcc ctcaatagaa ctagttttat    1800
ttggcaaaca tcatggaaag aatatatcag atacactact ctcgcacaga aagagacgtc    1860
aagtggtttg ggcatcaaaa ccataagcgg acgggtttcg agtttggacc tttgaatctg   1920
gttgatgttg gagcaagaag aagcagaaat gacacatggc atcattgtga agcttgcgtc    1980
gagacgaagc aagacaaagg caagtagca aaggtacact gttaccgccg gcaataacta    2040
cgtacgtacg tgcatgtaag acatgcattg taccgtgaca tacatgtatg tcatataaat   2100
ctatgtagat cactcctacg accggcggct tatcgtcact acaacgcatg atacatggat   2160
ggaatggatg tgaagtgaga ctgtgagagc actatcggaa tcgcgttctt tgtcaaatgt   2220 cgcttttccat aaataaacat gtgaacctag gcctaggcac cttccacttc aggcatcttc   2280
tacaaatgta gaatgtgtga aggtaggcaa acgtaacggg aaaggcagga agctcatcgc    2340
caacgcatct cctctcctgc tccttttgac gacctttcat acctgcaccc gcttttctg    2400 gaaagggcat caagatttat atatatatgt tattttcat tattattagc tttgtttaca     2460
acaagtatta ttattattat ccgggctgtg agcagaggga gctggtacaa cttgtccctt    2520
gagacggcca agaggcaaca gtgttgtggg cttgcggcca tgacgacgtt gctagctgcc    2580
gtgtccaaca ggaagagaag acggcgacgt ggtcgcactg tacgttttc ccgccacaca    2640 aacggggcgg gggcggtgg tatactggta tggtggccac tggccagccg ccgtgccggt    2700
gcaggcagca gcccacagga ccaacgccgc cgccaatgga tcgacggcc tctgctactg    2760 ctagaaatgg aaagcacgca ggtacgtggg gcccccctccc ttccccgcgc aagtgcagtg   2820
```

-continued

```
ccagtgcggc agtgcgtgtg tcattattct gtccggaccg gtaggtagta gtatcagatg    2880
tactaccagt caaacgacag tgccttccgc ggcggccaaa ggtacagtga cactttgcca    2940
aaaacaaaaa aaaaacagca ataaagaaa  ggaacgcgcg cgggaatata tcgatctcat    3000
cttttttttt ctttgttgtt gttgttgtct acagagatgg taaggaaata aataaataaa    3060
ggtgctacat aaagaccgga ttctttattt cttttccaaat ccagaaaagg aattatcttc   3120
cccggaatct attttcgaca aataataata ataatatatg attttgttat ttttcattgg    3180
ttctctggtt aatcattttg gacgtcatct acctaataac ataggtcgtc cactatgtgg    3240
agcgcacggc cttagcttaa gacacaattt gttgacttcc aggattatat aatccacctt    3300
atagattata taatcatata atgatatcta gttatcaaga ttatataata atccacctaa    3360
taatttgtgt tgtttgtttg cctcttgata tagtaggact atgtagccta ctgacatgat    3420
caatttactt ctctaatcac cggcaaaatg aaaaatccat tgtttacctt gccttgagtt    3480
gtattaacgg tttccaccaa agtcgttcaa gactctaagt agctcacatg tattccatcc    3540
agtcttcaaa tactttaagg ggtcttcact ttggatgtaa atactttatg tttaagcatt    3600
tgaagctcat tttagactag gatacccttg atctaggtgg tccacatatt ctcctaggca    3660
tgacaaatta ctcagagaca cgcttcctct tcccactaca tgtgtgcatg cattgaaacc    3720
gtgaaaaaac ctacgagtgc aatcgatcag gtcgggaaaa aaaggcacac ctagaggcta    3780
gagctcagtc agtcccgaac gattgcaaaa aaaaaaagac actagagctc gacctcaaaa    3840
cccagtgtgt caatttttac agccagcgtt gcaaccatct aagctaacat cttgtattta    3900
aatattatag aaacaacaac cctatttaat agttccttgg tatatataca agatcatgtc    3960
caaaacatca agcatttgaa gactagatgt agtacatgga ccaacctgca accttacttt    4020
atcagagaaa tcgtcagtcc acacatattt gtcattaatt accaaggcac tactgagagg    4080
ttagatgccc acaccgtttc accaaatgat tggttaaaaa gcacggactc ctgtggagct    4140
gctactctgc agaggagcgg gagtcagaac cattttttaga agagccaaag tcctaccaaa   4200
catactctta ctctctcttt ttaaaggtac tacctctttt gaatttaaat gtattactcc    4260
ctctttaaag agataataga gaagacgaac aagaaaggga gagggagaaa cga           4313
```

<210> SEQ ID NO 8
<211> LENGTH: 4232
<212> TYPE: DNA
<213> ORGANISM: Zea mays

<400> SEQUENCE: 8

```
ctccacctct ctcgtacgct ttgattggcc gctcgcacgc atttatcgcc aagatcgggc     60
ttgcccatca ctgggatcat cctggctggc tggctggccg gccacatatc aaacatggat    120
ttgctatatt ttaaatgcct gaaatatgtt atactatgtt ttttagataa cgatctttac    180
agtcgattta tgaatgtgta gaattaagat tgagcttcct gatgaaaaaa tcaggcaaga    240
ggctcttttg gttggagacc tggcatggca cttgcctgcg agtcaagcaa accctatgcc    300
actgtttgga ccaggccact ttcctagaga gccgaatcag acatcactat cggaattcga    360
atgagtgctc agcactttac cgagtgcaat taatcggaca ctcggcaaag cattctttgt    420
cgagtgccac tctcggcgaa ctaataaggc tctcgggaca gatctcgtat gtcgagagcg    480
gaacactcga catagaaaaa cactcggcaa aagaggtttt gccgaatgcc aagctctcgg    540
caaaatgcga cactcggtaa gggtcgtcaa gagtcgtcta ttgttgacgg ccattaactt    600
tcccgagtgt caaacgttga cacttgggaa ttatcttctt tttgtcgatt gtaacctggc    660
```

```
aaaccctcgg caaaagtata ctttgcggag tgtcttccct caacactcga taaagaatat      720
ttgtttcttt ttctttttc tataccaaac tctttgtgac gttttttctg cagtatatag       780
acatacatat tcaattttac acaattatca aagtgtttgc tataattaat agatttagtt      840
tgtttaattg aatttctgag aaccaaccaa atagacccga attagacata tctagacatt      900
taaaaagtaa gatactaaaa aataatagtg tttaccttca accggtacta aatatcattc      960
ctgtagtaga caggataacg aaagctagtc tatttagatc atcagttcca gttcgagatt     1020
ttaaatgcta gtccctccat ttcaatttac aatttattta atttttttag tgtgataccg     1080
tttagcgtat gtagctttga tttttttata tattttgca aaattttgaa taagacaagt     1140
gtgtcaaatt tggtgtaaaa attaaacgaa attataaatt ggagcggagg gagtagaaat     1200
ctacgatttt tctagctgag gcagactgtg cgcattccca tccatcgagt ccacttgcac     1260
ctctcctcga catgaatacg aatgtacgat ccgatgaatt ccccacaaag aagcaattaa     1320
cgtcaaatcc atcatcgtca taaaacgacg ataccgagct agcgtttaat tagtttgtta     1380
gacgaaccag aaactatatt atatcgcttt gtgtccaaaa attacttata ttatatatag     1440
ttctcgtgca tctacgtaca cgtaacatcg ctcttaaatt tgtccttact tggtgtaaaa     1500
agattaatct acaaagacta tattgttaaa gcaaaattga ggaagctgta tttaacctcg     1560
tgaccaccta aactagtggg aatgccccat ccctcaatag aactagtttt atttggcaaa     1620
catcatggaa agaatatatc agatacacta ctctcgcaca gagagagatg tcaagtggtt     1680
tgggcatcaa aaccataagc ggacgggttt cgagtttgga cctttgaatc tggttgatgt     1740
tggagcaaga agaagcaaaa atgacacatg gcatcattgt gaagcttgcg tcgagacgaa     1800
gcaagacaaa ggcaaagtag cgaaggtaca ctgttaccgc cggcaataac tacgtacgta     1860
catgcatgta agacatgcat tgtaccgtga catacatgta tgtcatataa atctatgtag     1920
atcactccta cgaccggcgg ctaatttcac tacacacatg atgcatggat ggaatggatg     1980
tgaagtgaga ctgtgagagc actatcggaa tcactttctt cgccgagtgt cgctttccat     2040
gaataaacat gtgaacctag gcctaggcac cttccacttc agggcttgtt cggttagctc     2100
tcaatccatg tggattgagc gggattggat gggtttgaat cccaaacaag tcaaacttct     2160
tcacaatttt ttccaatccc atccaatcca tgtgtattgg gaataaccga acaagccctc     2220
aggcatcttc tacaaatgta gaatgtgtga aggtaggcaa acgtaacgga aaggcaggaa     2280
gctcatcgcc aacgcatctc ctctcctgct ccttttgacg acctttcata cctgcacccg     2340 cttttttctgg aaagggcatc aagatttata tatatatata tatgttattc accagtaaat     2400
ttcattatta ttagctttgt ttacaacaag tattattatt attatccggg ctgtgagcag     2460
agggagctgg tacaacttgt cccttgagac ggccaagagg caacagtgtt gtgggcttgc     2520
ggccatgacg cgacgttgct agctgccgtg tccaacagga agagaagacg gcgacgtggt     2580
cgcactgtac gttttttcccg ccacacaaac ggggcggggg gcggtggtat actggtatgg     2640
tggccactgg ccagccgccg tgccggtgca ggcagcagcc cacaggacca acgccgccgc     2700
caatggatcg gacggcctct gctactgcta gaaatggaaa gcacgcaggt acgtggggcc     2760
ccctcccttt cccgcgcaag tgcagtgcca gtgcggcagt gcgtgtgtca ttattctgtc     2820
cggaccggta ggtagtagta tcagatgtac taccagtcaa acgacagtgc cttccgcggc     2880
ggccaaaggt acagtgacac tttgccaaaa acaaaaaaaa aacagcaaat aaagaaagga     2940
acgcgcgcgg gaatatatcg atctcatctt ttttttcctt ttttgttgtt gttgtctaca     3000
```

-continued

| | |
|---|---|
| gagatggtaa ggaataaata aataaaggtg ctaaataaag accggattct ttatttcttt | 3060 |
| ccaaatccag aaaaggaatt atcttccccg gaatctattt tcgagcaaat aataataata | 3120 |
| atatatgatt ttgttatttt tcattggttc tctggttaat cattttggac gtcatctacc | 3180 |
| taataacata ggtcgtccac tatgtggagc gcacggcctt agcttaagac acaatttgtt | 3240 |
| gacttccagg attatataat ccaccttata gattatataa tcatataatg atatctagtt | 3300 |
| atcaagatta tataataatc cacctaataa tttgtgttgt ttgtttgcct cttgatatag | 3360 |
| taggactatg tagcctactg acatgatcaa tttacttctc taatcaccgg caaaatgaaa | 3420 |
| aatccattgt ttaccttgcc ttgagttgta ttaacggttt ccaccaaagt cgttcaagac | 3480 |
| tctaagtagc tcacatgtat tccatccagt cttcaaatac tttaaggggt cttcactttg | 3540 |
| gatgtaaata ctttatgttt aagcatttga agctcatttt agactaggat acccttgatc | 3600 |
| taggtggtcc acatattctc ctaggcatga caaattactc agagacacgc ttcctcttcc | 3660 |
| cactacatgt gtgcatgcat tgaaaccgtg aaaaaaccta cgagtgcaat cgatcaggtc | 3720 |
| gggaaaaaaa ggcacaccta gaggctagag ctcagtcagt cccgaacgat tgcaaaaaaa | 3780 |
| aaaagacact agagctcgac ctcaaaaccc agtgtgtcaa ttttttacagc cagcgttgca | 3840 |
| accatctaag ctaacatctt gtatttaaat attatagaaa caacaaccct atttaatagt | 3900 |
| tccttggtat atatacaaga tcatgtccaa aacatcaagc atttgaagac tagatgtagt | 3960 |
| acatggacca acctgcaacc ttactttatc agagaaatcg tcagtccaca catatttgtc | 4020 |
| attaattacc aaggcactac tgagaggtta gatgcccaca ccgtttcacc aaatgattgg | 4080 |
| ttaaaaagca cggactcctg tggagctgct actctgcaga ggagcgggag tcagaaccat | 4140 |
| ttttagaaga gccaaagtcc taccaaacat actcttactc tctctttta aaggtactac | 4200 |
| ctcttttgaa tttaaatgta ttactccctc tt | 4232 |

<210> SEQ ID NO 9
<211> LENGTH: 49
<212> TYPE: DNA
<213> ORGANISM: artificial sequence
<220> FEATURE:
<223> OTHER INFORMATION: primer

<400> SEQUENCE: 9
ggggacaagt ttgtacaaaa aagcaggcta tgcagttgga tctgaacgt         49

<210> SEQ ID NO 10
<211> LENGTH: 47
<212> TYPE: DNA
<213> ORGANISM: artificial sequence
<220> FEATURE:
<223> OTHER INFORMATION: primer

<400> SEQUENCE: 10
ggggaccact ttgtacaaga aagctgggtt cagcggggat ggtgatg           47

<210> SEQ ID NO 11
<211> LENGTH: 24
<212> TYPE: DNA
<213> ORGANISM: artificial sequence
<220> FEATURE:
<223> OTHER INFORMATION: primer

<400> SEQUENCE: 11
ggatccgatc tgaacgtggc cgag                                    24

```
<210> SEQ ID NO 12
<211> LENGTH: 31
<212> TYPE: DNA
<213> ORGANISM: artificial sequence
<220> FEATURE:
<223> OTHER INFORMATION: primer

<400> SEQUENCE: 12
gaattcctag gcagctgttc ttgtctcttt g                              31

<210> SEQ ID NO 13
<211> LENGTH: 26
<212> TYPE: DNA
<213> ORGANISM: artificial sequence
<220> FEATURE:
<223> OTHER INFORMATION: primer

<400> SEQUENCE: 13
gcggccgcga tctgaacgtg gccgag                                    26

<210> SEQ ID NO 14
<211> LENGTH: 30
<212> TYPE: DNA
<213> ORGANISM: artificial sequence
<220> FEATURE:
<223> OTHER INFORMATION: primer

<400> SEQUENCE: 14
gaattctgtg ggactcccag cggcctgtgc                                30
```

METHODS AND COMPOSITIONS FOR MODULATING FLOWERING AND MATURITY IN PLANTS

CROSS-REFERENCE TO RELATED APPLICATIONS

This is a continuation application of U.S. application Ser. No. 11/190,339 filed Jul. 27, 2005, now issued as U.S. Pat. No. 7,479,584 which claims priority under 35 U.S.C. §119 of provisional application Ser. No. 60/592,268 filed Jul. 29, 2004, and which applications are hereby incorporated by reference in their entirety.

FIELD OF THE INVENTION

This invention is related to compositions and methods for affecting flowering time in plants.

BACKGROUND OF THE INVENTION

Plants have two basic growth modes during their life cycles—vegetative growth and flower and seed growth. Above ground vegetative growth of the plant develops from the apical meristem. This vegetative meristem gives rise to all of the leaves that are found on the plant. The plant will maintain its vegetative growth pattern until the apical meristem undergoes a change. This change actually alters the identity of the meristem from a vegetative to an inflorescence meristem. The inflorescence meristem produces small leaves before it next produces floral meristems. It is the floral meristem from which the flower develops.

From a genetic perspective, two phenotypic changes that control vegetative and floral growth are programmed in the plant. The first genetic change involves the switch from the vegetative to the floral state. If this genetic change is not functioning properly, then flowering will not occur. The second genetic event follows the commitment of the plant to form flowers. The observation that the organs of the plant develop in a sequential manner suggests that a genetic mechanism exists in which a series of genes are sequentially turned on and off.

Flowering time is an important agronomic trait in cultivated plant species as it determines in large measure the growing region of adaptation. Most angiosperm species are induced to flower in response to environmental stimuli such as day length and temperature, and internal cues, such as age. Genetic analysis revealed that there are several types of mutants that alter flowering time.

Studies of two distantly related dicotyledons, *Arabidopsis thaliana* and *Antirrhinum majus*, has led to the identification of three classes of homeotic genes, acting alone or in combination to determine floral organ identity (Bowman, et al., Development, 112:1, 1991; Carpenter and Coen, Genes Devl., 4:1483, 1990; Schwarz-Sommer, et al., Science, 250: 931, 1990). Several of these genes are transcription factors whose conserved DNA-binding domain has been designated the MADS box (Schwarz-Sommer, et al., supra).

Earlier acting genes that control the identity of flower meristems have also been characterized. Flower meristems are derived from inflorescence meristems in both *Arabidopsis* and *Antirrhinum*. Two factors that control the development of meristematic cells into flowers are known. In *Arabidopsis*, the factors are the products of the LEAFY gene (Weigel, et al., Cell 69:843, 1992) and the APETALA1 gene (Mandel, et al., Nature 360:273, 1992). When either of these genes is inactivated by mutation, structures combining the properties of flowers and inflorescence develop (Weigel, et al., supra; Irish and Sussex, Plant Cell, 2:741, 1990). In *Antirrhinum*, the homologue of the *Arabidopsis* LEAFY gene is FLORICAULA (Coen, et al., Cell, 63:1311, 1990) and that of the APETALA1 gene is SQUAMOSA (Huijser, et al., EMBO J., 11:1239, 1992). The latter pair contains MADS box domains.

Genetic studies in *Arabidopsis thaliana* have identified five genes (APETALA1 (AP1), APETALA2 (AP2), APETALA3 (AP3), PISTILLATA (PI), and AGAMOUS (AG)) that are involved in the specification of floral organ identity. Mutations in these genes result in homeotic transformation of one organ type into another, much like the homeotic selector genes in animal development. These five genes act in spatially localized domains in a flower and in different combinations to specify the development of the sepals, petals, stamens, and carpels. All five genes encode proteins which appear to function as transcription factors. Four of these proteins are members of the MADS domain family of dimeric transcription factors. MADS domain proteins are found in many organisms including yeast, mammals, insects, and plants. The fifth protein, AP2, is a member of another class of DNA binding proteins which may be unique to plants APETALA2 (AP2) plays an important role in the control of *Arabidopsis* flower and seed development and encodes a putative transcription factor that is distinguished by a novel DNA binding motif referred to as the AP2 domain. The AP2 domain containing or RAP2 (related to AP2) family of proteins is encoded by a minimum of 12 genes in *Arabidopsis*. The RAP2 genes encode two classes of proteins, AP2-like and EREBP-like, that are defined by the number of AP2 domains in each polypeptide as well as by two sequence motifs referred to as the YRG and RAYD elements that are located within each AP2 domain. RAP2 genes are differentially expressed in flower, leaf, inflorescence stem, and root. Moreover, the expression of at least three RAP2 genes in vegetative tissues are controlled by AP2. Thus, unlike other floral homeotic genes, AP2 is active during both reproductive and vegetative development.

Maize is a monocotyledonous plant species and belongs to the grass family. It is unusual for a flowering plant as it has unisexual inflorescences The male inflorescence (tassel) develops in a terminal position, whereas the female inflorescences (ears) grow in the axil of vegetative leaves. The inflorescences, as typical for grasses, are composed of spikelets. In the case of maize each spikelet contains two florets (the grass flower) enclosed by a pair of bracts (inner and outer glume). A number of genes have been identified which modify flowering time in maize including Id1 and DLF.

There is increasing incentive by those working in the field of plant biotechnology to successfully genetically engineer plants, including the major crop varieties. One genetic modification that would be economically desirable would be to accelerate the flowering time of a plant. Induction of flowering is often the limiting factor for growing crop plants. One of the most important factors controlling induction of flowering is day length, which varies seasonally as well as geographically. There is a need to develop a method for controlling and inducing flowering in plants, regardless of the locale or the environmental conditions, thereby allowing production of crops, at any given time. Since most crop products (e.g. seeds, grains, fruits), are derived from flowers, such a method for controlling flowering would be economically invaluable.

It is an object of the present invention to provide methods and compositions for affecting flowering time in plants.

It is yet another object of the invention to provide novel nucleotide sequences isolated from maize which encode proteins which affect flowering time in plants.

It is yet another object of the invention to provide maize RAP2.7 genes which affect flowering time and internode length in maize.

It is yet another object of the invention to provide DNA regulatory factors which enhance/inhibit the ability of RAP2.7 to regulate flowering time.

It is yet another object of the invention to provide methods and compositions including nucleotide constructs, vectors, transgenic cells and plants with altered flowering characteristics as described herein.

It is yet another object of the invention to provide markers for identification of mutant plants which may have altered flowering time by the presence of marker VGT1 sequences.

SUMMARY OF THE INVENTION

Compositions and methods involved in the modulation of flowering in plants are provided. The compositions include nucleic acid molecules isolated from maize which encode RAP2.7 proteins. Amino acid sequences of these proteins are also provided. Further, polynucleotides having nucleic acid sequences encoding maize RAP2.7 proteins are also provided. These proteins and the nucleotide sequences encoding them provide an opportunity to manipulate maturity of plants. When polynucleotide sequences encoding the RAP2.7 gene product are overexpressed flowering time is delayed, and when the product is inhibited flowering is earlier.

Typically maturity of a given plant is changed with crossing of earlier and later maturity plants. Agronomic traits such as yield, or lodging resistance are often lost in the process. The compositions of the invention provide for the ability to make significant changes in maturity while keeping other vegetative and reproductive characteristics similar using a transgenic approach.

The invention includes methods for manipulating the maturity of plants using polynucleotide sequences that were isolated from maize (*Zea mays*). These sequences alone, or in combination with other sequences, can be used to control plant maturity and thus area of adaptation. In another aspect of the present invention, nucleotide constructs such as expression cassettes and transformation vectors comprising the isolated nucleotide sequences are disclosed. The transformation vectors can be used to transform plants and express the flower modulation control genes in the transformed cells. In this manner, the maturity of plants as well as area of adaptation can be controlled. Transformed cells as well as regenerated transgenic plants and seeds containing and expressing the isolated polynucleotide sequences and protein products are also provided.

Also according to the invention, a novel DNA sequence termed (VGT1) has been identified which is a 2 kb region on maize chromosome 8 L. VGT1 acts as a CIS interaction type non-coding RNA sequence for maize RAP2.7. In mutants with early flowering, VGT1 may interact or repress the expression level of RAP2.7 causing down regulation of RAP2.7 and early flowering. Thus the invention also comprises nucleotide sequences encoding a VGT1 DNA factor which interacts either directly or indirectly with RAP2.7 in modulating the flowering time in plants. The invention includes nucleotide sequences, polymorphisms, "expression-type" constructs with the VGT1 sequences operably linked to promoters regions for transcription of the same, transgenic cells and plants with altered flowering time. The VGT1 sequences and the alternate forms thereof may also be used as markers to identify plants with flowering that may be different from wild type.

For any of the sequences disclosed herein, the polynucleotide of the invention or at least 20 contiguous bases therefrom may be used as probes to isolate and identify similar genes in other plant species. The sequences disclosed may also be used to isolate regulatory elements and promoter sequences that are natively associated with the polynucleotides disclosed herein to give spatial and temporal expression of operatively linked sequences to flowering in plants.

DESCRIPTION OF THE FIGURES

FIG. 3 is the deduced amino acid sequence of RAP2.7 from C22-4 allele (SEQ ID NO:2). The two putative AP2 domains are highlighted in bold, whereas the linker region between them is italicized. The well conserved YRG and RAYD motifs are underlined, although there is an R to K substitution in the second RAYD motif.

FIG. 4 (4A-4K) is a GAP alignment between the genomic RAP2.7 from B73 (SEQ ID NO:3) compared to the sequence of RAP2.7 of M017 (SEQ ID NO:4). Gap Weight: 50; Average Match: 10.000; Length Weight: 3; Average Mismatch: 0.000; Quality: 59308; Length: 8586; Ratio: 7.730; Gaps: 41; Percent Similarity: 87.482, Percent Identity: 87.482. Vladutu, et al., (1999) *Genetics* 153:993-1007.

FIG. 8 is a graph showing the results of association mapping for markers developed at the Vgt1-Rap2.7 region and phenotypic data for flowering time collected in Bologna (2002 and 2003) among a set of 96 maize inbred lines. Statistical association is expressed as P from ANOVA tests.

FIG. 9 (9A-9H) is an alignment of the VGT1 sequences from all four lines, including a consensus sequence line N28 was identical to B73 (SEQ ID NOS: 5, 6, 7, and 8).

DETAILED DESCRIPTION OF THE INVENTION

Figure 1:
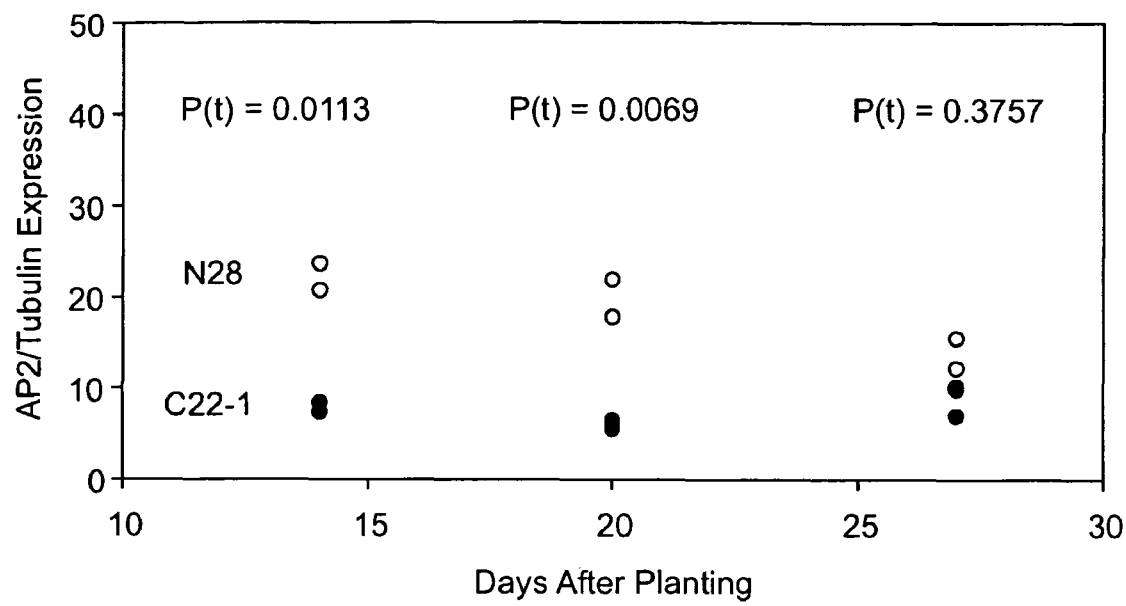
FIG. 1 is a graph depicting the levels of RAP2.7 expression at Day: 14, day 20 and day 27.

The present invention provides, inter alia, compositions and methods for manipulating flowering time in plants. As used herein the term "flowering time" or maturity shall mean the time at which a plant reaches physiological maturity and is capable of reproducing.

The compositions comprise nucleic acid molecules comprising sequences of plant genes and the polypeptides encoded thereby as well as regulatory factors which are non-coding. Particularly, the nucleotide and amino acid sequences for a maize RAP2.7 (related to AP2 domain containing) gene are provided. Three RAP2.7 encoding nucleotide sequences are provided at SEQ ID NOS: 1 (cDNA), 3 (genomic), and 4 (genomic) with the corresponding protein at SEQ ID NO: 2. Three VGT1 nucleotide sequences are provided at SEQ ID NOS: 5, 6, and 7 with the consensus sequence at SEQ ID NO:8. As discussed in more detail below, the sequences of the invention are involved in many basic biochemical pathways that regulate flowering time and maturity in plants. Thus, methods are provided for the expression of these sequences in a host plant to modulate plant flowering. Some of the methods involve stably transforming a plant with a nucleotide sequence capable of modulating plant flowering operably linked with a promoter capable of driving expression (or transcription) of a nucleotide sequence in a plant cell.

Promoter and other regulatory elements which are natively associated with these genes can be easily isolated using the sequences and methods described herein with no more than routine experimentation. These sequences can be used to identify promoter, enhancer or other signaling signals in the regulatory regions of RAP2.7 encoding sequences. These regulatory and promoter elements provide for temporal and spatial expression of operably linked sequences with flowering in a plant. Methods are provided for the regulated expression of a nucleotide sequence of interest that is operably linked to the promoter regulatory sequences disclosed herein. Nucleotide sequences operably linked to the promoter sequences are transformed into a plant cell. Exposure of the transformed plant to a stimulus such as the timing of flowering induces transcriptional activation of the nucleotide sequences operably linked to these promoter regulatory sequences.

By "heterologous nucleotide sequence" is intended a sequence that is not naturally occurring with the referenced sequence. While the referenced nucleotide sequence is heterologous to the promoter sequence or vice versa, it may be homologous, or native, or heterologous, or foreign, to the plant host.

By "operably linked" is intended a functional linkage between a promoter sequence and a second sequence, wherein the promoter sequence initiates and mediates transcription of the DNA sequence corresponding to the second sequence. Generally, operably linked means that the nucleic acid sequences being linked are contiguous and, where necessary to join two protein coding regions, contiguous and in the same reading frame. In the case of a DNA regulatory factor the nucleic acid sequences are transcribed only.

A polypeptide is said to have RAP2.7-like activity when it has one or more of the properties of the native protein. It is within the skill in the art to assay protein activities obtained from various sources to determine whether the properties of the proteins are the same. In so doing, one of skill in the art may employ any of a wide array of known assays including, for example, biochemical and/or pathological assays. For example, one of skill in the art could readily produce a plant transformed with a RAP2.7 polypeptide variant and assay a property of native RAP2.7 protein in that plant material to determine whether a particular RAP2.7 property was retained by the variant.

The compositions and methods of the invention are involved in biochemical pathways and as such may also find use in the activation or modulation of expression of other genes, including those involved in other aspects of flowering time.

Although there is some conservation among these genes, proteins encoded by members of these gene families may contain different elements or motifs or sequence patterns that modulate or affect the activity, subcellular localization, and/or target of the protein in which they are found. Such elements, motifs, or sequence patterns may be useful in engineering novel enzymes for modulating gene expression in particular tissues. By "modulating" or "modulation" is intended that the level of expression of a gene may be increased or decreased relative to genes driven by other promoters or relative to the normal or uninduced level of the gene in question.

According to the invention, overexpression of maize RAP2.7 caused flowering that was later than normal in plants as well as an increased number of leaves (nodes) produced prior to flowering resulting in taller plant stature. Inhibition of maize RAP2.7 caused maturation or flowering that was earlier than normal. Also the presence of mutant VGT1 correlated with earlier flowering as well, thus leading to the concept that VGT1 acts as direct or indirect enhancer/regulator of RAP2.7. Expression of the proteins encoded by RAP2.7 encoding sequences or transcription of the VGT1 regulatory element can be used to modulate or regulate the expression of proteins in these flowering pathways and other directly or indirectly affected pathways. Hence, the compositions and methods of the invention find use in altering plant flowering and maturity. In other embodiments, fragments of the sequences are used to confer desired properties to synthetic constructs for use in regulating plant maturity and flowering.

The present invention provides for isolated nucleic acid molecules comprising nucleotide sequences encoding the amino acid sequence shown in SEQ ID NOS: 2 as well as their conservatively modified variants. Further provided are polypeptides having an amino acid sequence encoded by a nucleic acid molecule described herein, for example those polypeptides comprising the sequences set forth in SEQ ID NO: 1, 3 and 4, and fragments and variants thereof.

The present invention further provides for an isolated nucleic acid molecule comprising the sequences shown in SEQ ID NO: 1, 3, 4, 5, 6, 7, or 8.

The invention encompasses isolated or substantially purified nucleic acid or protein compositions. An "isolated" or "purified" nucleic acid molecule or protein, or biologically active portion thereof, is substantially free of other cellular material, or culture medium when produced by recombinant techniques, or substantially free of chemical precursors or other chemicals when chemically synthesized. In some embodiments, an "isolated" nucleic acid is free of sequences (such as other protein-encoding sequences) that naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb, 0.4 kb, 0.3 kb, 0.2 kb, or 0.1 kb, or 50, 40, 30, 20, or 10 nucleotides that naturally flank the nucleic acid molecule in genomic DNA of the cell from which the nucleic acid is derived. A protein that is substantially free of cellular material includes preparations of protein having less than about 30%, 20%, 10%, 5%, (by dry weight) of contaminating protein. When the protein of the invention or biologically active portion thereof is recombinantly produced, culture medium may represent less than about 30%, 20%, 10%, or 5% (by dry weight) of chemical precursors or non-protein-of-interest chemicals.

Fragments and variants of the disclosed nucleotide sequences which retain the functional properties of the encoded peptide or of the non-coding RNA are encompassed by the present invention. By "fragment" is intended a portion of the nucleotide sequence or a portion of the amino acid sequence and hence protein encoded thereby. Fragments of a nucleotide sequence may encode protein fragments that retain the biological activity of the native protein and hence affect flowering by retaining RAP2.7-like activity or may include portions of non-coding regulatory element which retain the RAP2.7 modulating activity of VGT1. Alternatively, fragments of a nucleotide sequence that are useful as hybridization probes generally do not encode fragment proteins retaining biological activity. Thus, fragments of a nucleotide sequence may range from at least about 20 nucleotides, about 50 nucleotides, about 100 nucleotides, and up to the full-length nucleotide sequence encoding the proteins or regulating RAP2.7 of the invention.

A fragment of a RAP2.7 nucleotide sequence that encodes a biologically active portion of a RAP2.7 protein of the invention will encode at least 12, 25, 30, 50, 75, 100, 125, 150, 175, 200, 225, 250, 275, 300, 325, 350, 375, 400, 425, or 450, contiguous amino acids, or up to the total number of amino acids present in a full-length RAP2.7 protein of the invention.

A fragment of a VGT1 nucleotide sequence that encodes a biologically active non-transcribed RNA of the invention will encode at least 12, 25, 30, 50, 75, 100, 125, 150, 175, 200, 225, 250, 275, 300, 325, 350, 375, 400, 425, 450, 475, 500, 525, 550, 575, 600, 625, 650, 675, or 680 contiguous nucleotide bases or up to the total number of nucleotides present in a full-length VGT1 regulatory element of the invention.

Fragments of a RAP2.7 or VGT1 nucleotide sequence that are useful as hybridization probes or PCR primers generally need not encode a biologically active portion of a protein or RNA. Thus, a fragment of a RAP2.7 or VGT1 nucleotide sequence may encode a biologically active portion of a RAP2.7 protein or a biologically active non-coding RNA, or it may be a fragment that can be used as a hybridization probe or PCR primer using methods disclosed below. A biologically active portion of a RAP2.7 protein or VGT1 regulatory element can be prepared by isolating a portion of the RAP2.7 or VGT1 nucleotide sequences of the invention, expressing the encoded portion of the Rap2.7 or the active portion of the VGT1 regulatory element (e.g., by recombinant expression in vitro), and assessing the activity of the encoded portion of the RAP2.7 protein or the regulating ability of the regulatory element on RAP2.7. Nucleic acid molecules that are fragments of a RAP2.7 or VGT1 nucleotide sequence comprise at least 16, 20, 25, 30, 40, 50, 60, 70, 80, 90, 100, 125, 150, 175, 200, 225, 250, 300, 350, 400, 450, 500, 550, 600, 650, 700, 750, 800, 850, 900, 950, 1000, 1050, 1100, 1200, 1300, 1400, 1500, 1600, 1700, 1800, 1900, 2000, 2100, 2200, 2300, or 2400 nucleotides, or up to the number of nucleotides present in a full RAP2.7 or VGT1 nucleotide sequence disclosed herein.

By "variants" is intended substantially similar sequences. For nucleotide sequences, conservative variants include those sequences that, because of the degeneracy of the genetic code, encode the amino acid sequence of one of the polypeptides of the invention. Naturally occurring allelic variants such as these can be identified with the use of well-known molecular biology techniques, as, for example, with polymerase chain reaction (PCR) and hybridization techniques as outlined below. Variant nucleotide sequences also include synthetically-derived nucleotide sequences, such as those generated, for example, by using site-directed mutagenesis but which still encode a RAP2.7 protein or VGT1 regulatory element of the invention. Generally, variants of a particular nucleotide sequence of the invention will have at least 40%, 50%, 60%, 70%, generally at least 75%, 80%, 85%, or about 90%, 91%, 92%, 93%, 94%, 95%, 96%, 97%, 98%, 99%, or more sequence identity to that particular nucleotide sequence as determined by sequence alignment programs described elsewhere herein using default parameters.

By "variant" protein is intended a protein derived from the native protein by deletion (so-called truncation) or addition of one or more amino acids to the N-terminal and/or C-terminal end of the native protein; deletion or addition of one or more amino acids at one or more sites in the native protein; or substitution of one or more amino acids at one or more sites in the native protein. Variant proteins encompassed by the present invention are biologically active, that is they continue to possess the desired biological activity of the native protein, hence they will continue to possess at least one activity possessed by the native RAP2.7 protein. Such variants may result from, for example, genetic polymorphism or from human manipulation. Biologically active variants of a RAP2.7 native protein of the invention will have at least 40%, 50%, 60%, 70%, generally at least 75%, 80%, 85%, 86%, 87%, 88%, 89%, about 90%, 91%, 92%, 93%, 94%, 95%, 96%, 97%, 98%, 99%, or more sequence identity to the amino acid sequence for the native protein as determined by sequence alignment programs described elsewhere herein using default parameters. A biologically active variant of a protein of the invention may differ from that protein by as few as 1-15 amino acid residues, as few as 1-10, as few as 5, as few as 4, 3, 2, or even 1 amino acid residue. As used herein, reference to a particular nucleotide or amino acid sequence (a RAP2.7 or VGT1 sequence) shall include all modified variants as described supra.

The proteins of the invention may be altered in various ways including amino acid substitutions, deletions, truncations, and insertions. Methods for such manipulations are generally known in the art. For example, amino acid sequence variants of RAP2.7 proteins can be prepared by mutations in the DNA. Methods for mutagenesis and nucleotide sequence alterations are well known in the art. See, for example, Kunkel (1985) *Proc. Nad. Acad. Sci. USA* 82:488-492; Kunkel et al. (1987) *Methods in Enzymol.* 154:367-382; U.S. Pat. No. 4,873,192; Walker and Gaastra, eds. (1983) *Techniques in Molecular Biology* (MacMillan Publishing Company, New York) and the references cited therein. Guidance as to appropriate amino acid substitutions that do not affect biological activity of the protein of interest may be found in the model of Dayhoff et al. (1978) *Atlas of Protein Sequence and Structure* (Natl. Biomed. Res. Found., Washington, D.C.), herein incorporated by reference. Conservative substitutions, such as exchanging one amino acid with another having similar properties, may be made.

Thus, the nucleotide sequences of the invention include both naturally occurring sequences as well as mutant forms. Likewise, the proteins of the invention encompass both naturally-occurring proteins as well as variations and modified forms thereof. Such variants whether protein or nucleotide will continue to possess the desired RAP2.7 or VGT1-like activity. It is recognized that variants need not retain all of the activities and/or properties of the native RAP2.7 or VGT1. Obviously, the mutations that will be made in the DNA encoding the RPA2.7 variant must not place the sequence out of reading frame and in some embodiments will not create complementary regions that could produce secondary mRNA structure. See, EP Patent Application Publication No. 75,444.

The deletions, insertions, and substitutions of the protein or nucleotide sequences encompassed herein are not expected to produce radical changes in the characteristics of the RAP 2.7 protein or VGT1 regulatory element. However, when it is difficult to predict the exact effect of the substitution, deletion, or insertion in advance of doing so, one skilled in the art will appreciate that the effect will be evaluated by routine screening assays. That is, the activity of RAP2.7 polypeptides or VGT1 can be evaluated by either a change in flowering time or maturity when the encoded protein or regulatory element is altered.

Variant nucleotide sequences and proteins also encompass sequences and proteins derived from a mutagenic and recombinogenic procedure such as DNA shuffling. With such a procedure, one or more different RAP2.7 or VGT1 coding sequences can be manipulated to create a new RAP2.7 or VGT1 possessing the desired properties. In this manner, libraries of recombinant polynucleotides are generated from a population of related sequence polynucleotides comprising sequence regions that have substantial sequence identity and can be homologously recombined in vitro or in vivo. For example, using this approach, sequence motifs encoding a domain of interest may be shuffled between the RAP2.7 encoding polynucleotide of the invention and other known flowering genes to obtain a new gene coding for a protein with an improved property of interest, such as an increased $K_m$ in the case of an enzyme. Strategies for such DNA shuffling are known in the art. See, for example, Stemmer (1994) *Proc. Natl. Acad. Sci. USA* 91:10747-10751; Stemmer (1994) *Nature* 370:389391; Crameri et al. (1997) *Nature Biotech.* 15:436-438; Moore et al. (1997) *J. Mol. Biol.* 272:336-347; Zhang et al. (1997) *Proc. Natl. Acad. Sci. USA* 94:4504-4509; Crameri et al. (1998) *Nature* 391:288-291; and U.S. Pat. Nos. 5,605,793 and 5,837,458.

The compositions of the invention also include isolated nucleic acid molecules comprising the promoter nucleotide sequences natively associated with the RAP2.7 polynucleotides. By "promoter" is intended a regulatory region of DNA usually comprising a TATA box capable of directing RNA polymerase II to initiate RNA synthesis at the appropriate transcription initiation site for a particular coding sequence. A promoter may additionally comprise other recognition sequences generally positioned upstream or 5' to the TATA box, referred to as upstream promoter elements, which influence the transcription initiation rate.

The nucleotide sequences of the invention can be used to isolate corresponding sequences from other organisms, particularly other plants, more particularly other crop plants. In this manner, methods such as PCR, hybridization, and the like can be used to identify such sequences based on their sequence homology to the sequences set forth herein. Sequences isolated based on their sequence identity to the nucleotide sequences set forth herein or to fragments thereof are encompassed by the present invention. Such sequences include sequences that are orthologs of the disclosed sequences. By "orthologs" is intended genes derived from a common ancestral gene and which are found in different species as a result of speciation. Genes found in different species are considered orthologs when their nucleotide sequences and/or their encoded protein sequences share substantial identity as defined elsewhere herein. Functions of orthologs are often highly conserved among species. Thus, isolated sequences that have RAP2.7 or VGT1 activity or encode a RAP2.7 protein and which hybridize under stringent conditions to RAP2.7 or VGT1 sequences disclosed herein, or to fragments thereof, are encompassed by the present invention.

In a PCR approach, oligonucleotide primers can be designed for use in PCR reactions to amplify corresponding DNA sequences from cDNA or genomic DNA extracted from any plant of interest. Methods for designing PCR primers and PCR cloning are generally known in the art and are disclosed in Sambrook et al. (1989) *Molecular Cloning: A Laboratory Manual* (2d ed., Cold Spring Harbor Laboratory Press Plainview, N.Y.). See also Innis et al., eds. (1990) *PCR Protocols: A Guide to Methods and Applications* (Academic Press, New York); Innis and Gelfand, eds. (1995) *PCR Strategies* (Academic Press, New York); and Innis and Gelfand, eds. (1999) *PCR Methods Manual* (Academic Press, New York). Known methods of PCR include, but are not limited to, methods using paired primers, nested primers, single specific primers, degenerate primers, gene-specific primers, vector-specific primers, partially-mismatched primers, and the like.

In hybridization techniques, all or part of a known nucleotide sequence is used as a probe that selectively hybridizes to other corresponding nucleotide sequences present it a population of cloned genomic DNA fragments or cDNA fragments (i.e., genomic or cDNA libraries) from a chosen organism. The hybridization probes may be genomic DNA fragments, cDNA fragments, RNA fragments, or other oligonucleotides, and may be labeled with a detectable group such as $^{32}P$, or any other detectable marker. Thus, for example, probes for hybridization can be made by labeling synthetic oligonucleotides based on the disease-resistant sequences of the invention. Methods for preparation of probes for hybridization and for construction of cDNA and genomic libraries are generally known in the art and are disclosed in Sambrook et al. (1989)

*Molecular Cloning: A Laboratory Manual* (2d ed., Cold Spring Harbor Laboratory Press, Plainview, N.Y.).

For example, an entire sequence disclosed herein, or one or more portions thereof, may be used as a probe capable of specifically hybridizing to corresponding flowering or maturity regulating sequences, including promoters and messenger RNAs. To achieve specific hybridization under a variety of conditions, such probes include sequences that are unique among flowering or maturity related sequences and may be at least about 10 or 15 or 17 nucleotides in length or at least about 20 or 22 or 25 nucleotides in length. Such probes may be used to amplify corresponding sequences from a chosen organism by PCR. This technique may be used to isolate additional coding sequences from a desired organism or as a diagnostic assay to determine the presence of coding sequences in an organism. Hybridization techniques include hybridization screening of plated DNA libraries (either plaques or colonies; see, for example, Sambrook et al. (1989) *Molecular Cloning: A Laboratory Manual* (2d ed., Cold Spring Harbor Laboratory Press, Plainview, N.Y.).

Hybridization of such sequences may be carried out under stringent conditions. By "stringent conditions" or "stringent hybridization conditions" is intended conditions under which a probe will hybridize to its target sequence to a detectably greater degree than to other sequences (e.g., at least 2-fold over background). Stringent conditions are sequence-dependent and will be different under different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing). Generally, a probe is less than about 1000 nucleotides in length or less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3. Incubation should be at a temperature of least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulfate) at 37° C., and a wash in 1× to 2×SSC (20×SSC=3.0 M NaCl, 0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C. for 20 minutes. Optionally, wash buffers may comprise about 0.1% to about 1% SDS. Duration of hybridization is generally less than about 24 hours, usually about 4 to about 12 hours.

Specificity is typically a function of post-hybridization washes, the critical factors being the ionic strength and temperature of the final wash solution. For DNA-DNA hybrids, the $T_m$ can be approximated from the equation of Meinkoth and Wahl (1984) *Anal. Biochem.* 138:267-284: $T_m$=81.5° C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization, and/or wash conditions can be adjusted to hybridize to sequences of the desired identity. For example, if sequences with >90% identity are sought, the $T_m$ can be decreased 10° C. Generally, stringent conditions are selected to be about 5° C. lower than the thermal melting point (Tm) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point (Tm); low stringency conditions can utilize a hybridization and/or wash at 11, 12, 13, 14, 15, or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), the SSC concentration may be increased so that a higher temperature can be used. An extensive guide to the hybridization of nucleic acids is found in Tijssen (1993) *Laboratory Techniques in Biochemistry and Molecular Biology-Hybridization with Nucleic Acid Probes*, Part I, Chapter 2 (Elsevier, N.Y.); and Ausubel et al., eds. (1995) *Current Protocols in Molecular Biology*, Chapter 2 (Greene Publishing and Wiley-Interscience, New York). See Sambrook et al. (1989) *Molecular Cloning: A Laboratory Manual* (2d ed., Cold Spring Harbor Laboratory Press, Plainview, N.Y.).

In general, sequences that encode a RAP2.7 protein or which encode a VGT1 regulatory element and which hybridize to the RAP2.7 or VGT1 sequences disclosed herein will be at least about 70% homologous, and even about 80%, 85%, 90%, 91%, 92%, 93%, 94%, 95%, 98%, 99% or more homologous with the disclosed sequences. That is, the sequence identity of the sequences may be from about 70% or 75%, and even about 80%, 85%, 87%, 90%, 91%, 92%, 93%, 94%, 95%, 96%, 97%, 98%, or 99% identical, or higher, so that the sequences may differ by only 10, 9, 8, 7, 6, 5, 4, 3, 2, or 1 amino acid residue or by 20, 19, 18, 17, 16, 15, 14, 13, 12, 11, 10, 9, 8, 7, 6, 5, 4, 3, 2, or 1 nucleic acid.

The following terms are used to describe the sequence relationships between two or more nucleic acids or polynucleotides: (a) "reference sequence," (b) "comparison window," (c) "sequence identity," (d) "percentage of sequence identity," and (e) "substantial identity."

(a) As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

(b) As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence a gap penalty is typically introduced and is subtracted from the number of matches.

Methods of alignment of sequences for comparison are well known in the art. Thus, the determination of percent sequence identity between any two sequences can be accomplished using a mathematical algorithm. Non-limiting examples of such mathematical algorithms are the algorithm of Myers and Miller (1988) *CABIOS* 4:11-17; the local homology algorithm of Smith et al. (1981) *Adv. Appl. Math.* 2:482; the homology alignment algorithm of Needleman and Wunsch (1970) *J. Mol. Biol.* 48:443-453; the search-for-similarity-method of Pearson and Lipman (1988) *Proc. Natl. Acad. Sci.* 85:2444-2448; the algorithm of Karlin and Altschul (1990) *Proc. Natl. Acad. Sci. USA* 872264, modified as in Karlin and Altschul (1993) *Proc. Natl. Acad. Sci. USA* 90:5873-5877.

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the Wisconsin Genetics Software Package, Version 8 (available from Genetics Computer Group (GCG), 575 Science Drive, Madison, Wis., USA). Alignments using these programs can be performed using the default parameters. The CLUSTAL program is well described by Higgins et al. (1988) *Gene* 73:237-244 (1988); Higgins et al. (1989) *CABIOS* 5:151-153; Corpet et al. (1988) *Nucleic Acids Res.* 16:10881-90; Huang et al. (1992) CABIOS 8:155-65; and Pearson et al. (1994) *Meth. Mol. Biol.* 24:307-331. The ALIGN program is based on the algorithm of Myers and Miller (1988) supra. A PAM 120 weight residue table, a gap length penalty of 12, and a gap penalty of 4 can be used with the ALIGN program when comparing amino acid sequences. The BLAST programs of Altschul et al (1990) J. Mol. *Biol.* 215:403 are based on the algorithm of Karlin and Altschul (1990) supra. BLAST nucleotide searches can be performed with the BLASTN program, score=100, wordlength=12, to obtain nucleotide sequences homologous to a nucleotide sequence encoding a protein of the invention. BLAST protein searches can be performed with the BLASTX program, score=50, wordlength=3, to obtain amino acid sequences homologous to a protein or polypeptide of the invention. To obtain gapped alignments for comparison purposes, Gapped BLAST (in BLAST 2.0) can be utilized as described in Altschul et al. (1997) *Nucleic Acids Res.* 25:3389. Alternatively, PSI-BLAST (in BLAST 2.0) can be used to perform an iterated search that detects distant relationships between molecules. See Altschul et al. (1997) supra. When utilizing BLAST, Gapped BLAST, or PSI-BLAST, the default parameters of the respective programs (e.g., BLASTN for nucleotide sequences, BLASTX for proteins) can be used (see information at www.ncbi.nlm.nih.gov). Alignment may also be performed manually by inspection.

Unless otherwise stated, sequence identity/similarity values provided herein refer to the value obtained using GAP version 10 using the following parameters: % identity using GAP Weight of 50 and Length Weight of 3; % similarity using Gap Weight of 12 and Length Weight of 4, or any equivalent program. By "equivalent program" is intended any sequence comparison program that, for any two sequences in question, generates an alignment having identical nucleotide or amino acid residue matches and an identical percent sequence identity when compared to the corresponding alignment generated by GAP Version 10. GAP uses the algorithm of Needleman and Wunsch (1970) J. *Mol. Biol.* 48:443-453, to find the alignment of two complete sequences that maximizes the number of matches and minimizes the number of gaps. GAP considers all possible alignments and gap positions and creates the alignment with the largest number of matched bases and the fewest gaps. It allows for the provision of a gap creation penalty and a gap extension penalty in units of matched bases. GAP must make a profit of gap creation penalty number of matches for each gap it inserts. If a gap extension penalty greater than zero is chosen, GAP must, in addition, make a profit for each gap inserted of the length of the gap times the gap extension penalty. Default gap creation penalty values and gap extension penalty values in Version 10 of the Wisconsin Genetics Software Package for protein sequences are 8 and 2, respectively. For nucleotide sequences the default gap creation penalty is 50 while the default gap extension penalty is 3. The gap creation and gap extension penalties can be expressed as an integer selected from the group of integers consisting of from 0 to 200. Thus, for example, the gap creation and gap extension penalties can be 0, 1, 2, 3, 4, 5, 6, 7, 8, 9, 10, 15, 20, 25, 30, 35, 40, 45, 50, 55, 60, 65 or greater.

GAP presents one member of the family of best alignments. There may be many members of this family, but no other member has a better quality. GAP displays four figures of merit for alignments: Quality, Ratio, Identity, and Similarity. The Quality is the metric maximized in order to align the sequences. Ratio is the quality divided by the number of bases in the shorter segment. Percent Identity is the percent of the symbols that actually match. Percent Similarity is the percent of the symbols that are similar. Symbols that are across from gaps are ignored. A similarity is scored when the scoring matrix value for a pair of symbols is greater than or equal to 0.50, the similarity threshold. The scoring matrix used in Version 10 of the Wisconsin Genetics Software Package is BLOSUM62 (see Henikoff and Henikoff (1989) *Proc. Natl. Acad. Sci. USA* 89:10915).

(c) As used herein, "sequence identity" or "identity" in the context of two nucleic acid or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity." Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

(e)(i) The term "substantial identity" of polynucleotide sequences means that a polynucleotide comprises a sequence that has at least 70%, 80%, 85%, 90%, 95%, or higher sequence identity compared to a reference sequence using one of the alignment programs described using standard parameters. One of skill in the art will recognize that these values can be appropriately adjusted to determine corresponding identity of proteins encoded by two nucleotide sequences by taking into account codon degeneracy, amino acid similarity, reading frame positioning, and the like. Substantial identity of amino acid sequences for these purposes normally means sequence identity of at least 50%, 55%, 60%, 65%, 70%, 75%, 80%, 85%, 90%, or at least 95% or higher sequence identity.

Another indication that nucleotide sequences are substantially identical is if two molecules hybridize to each other under stringent conditions. Generally, stringent conditions are selected to be about 5° C. lower than the thermal melting point (Trr,) for the specific sequence at a defined ionic strength and pH. However, stringent conditions encompass temperatures in the range of about 1° C. to about 20° C. lower than the $T_m$, depending upon the desired degree of stringency as otherwise qualified herein. Nucleic acids that do not hybridize to each other under stringent conditions are still substantially identical if the polypeptides they encode are substantially identical. This may occur, e.g., when a copy of a nucleic acid is created using the maximum codon degeneracy permitted by the genetic code. One indication that two nucleic acid sequences are substantially identical is when the polypeptide encoded by the first nucleic acid is immunologically cross-reactive with the polypeptide encoded by the second nucleic acid.

(e)(ii) The term "substantial identity" in the context of a peptide indicates that a peptide comprises a sequence with at least 70%, 75%, 80%, 83%, 85%, 88%, 90%, 93%, 95%, 96%, 97%, 98%, or 99% or higher sequence identity to the reference sequence over a specified comparison window. Preferably, optimal alignment is conducted using the homology alignment algorithm of Needleman and Wunsch (1970) *J Mol. Biol.* 48:443-453. An indication that two peptide sequences are substantially identical is that one peptide is immunologically reactive with antibodies raised against the second peptide. Thus, a peptide is substantially identical to a second peptide, for example, where the two peptides differ only by a conservative substitution. Peptides that are "substantially similar" share sequences as noted above except that residue positions that are not identical may differ by conservative amino acid changes.

Methods for altering flowering time in a plant are provided. In some embodiments, the methods involve stably transforming a plant with a DNA construct comprising a nucleotide sequence of the invention operably linked to a promoter that drives expression (or transcription) in a plant. While the choice of promoter will depend on the desired timing and location of expression of the nucleotide sequences, desirable promoters include constitutive and tissue specific promoters. These methods may find use in agriculture, particularly in changing the maturity of a particular crop plant to alter its area of adaptation. Thus, transformed plants, plant cells, plant tissues and seeds thereof are provided by the present invention.

In another embodiment, the methods of the present invention involve identifying phenotypes associated with an altered flowering time by loss of RAP2.7 or VGT1 activity in plants that contain transposon insertions within the nucleotide sequences herein.

In some embodiments, the nucleic acid molecules comprising RAP2.7 or VGT1 sequences of the invention are provided in expression cassettes or nucleotide constructs for expression/transcription in the plant of interest. Such cassettes will include 5' and 3' regulatory sequences operably linked to a RAP2.7 or VGT1 nucleotide sequence of the invention. By "operably linked" is intended a functional linkage between a promoter and a second sequence, wherein the promoter sequence initiates and mediates transcription of the DNA sequence corresponding to the second sequence. The cassette may additionally contain at least one additional nucleotide sequence to be cotransformed into the organism. Alternatively, the additional sequence(s) can be provided on multiple expression cassettes or nucleotide construct.

Such an expression cassette or nucleotide construct is provided with a plurality of restriction sites for insertion of the RAP2.7 or VGT1 sequence to be under the transcriptional regulation of the regulatory regions. The expression cassette or nucleotide construct may additionally contain selectable marker genes. The expression cassette will include in the 5'-3' direction of transcription, a transcriptional and if necessary a translational initiation region, a RAP2.7 or VGT1 nucleotide sequence of the invention, and a transcriptional and if necessary, translational termination region functional in plants. The transcriptional initiation region, or promoter, may be native or analogous or foreign or heterologous to the plant host. Additionally, the promoter may be the natural sequence or alternatively a synthetic sequence. By "foreign" is intended that the transcriptional initiation region is not found in the native plant into which the transcriptional initiation region is introduced. As used herein, a "chimeric gene" comprises a coding sequence operably linked to a transcription initiation region that is heterologous to the coding sequence.

While it may be preferable to regulate RAP2.7 or VGT1 sequences using heterologous promoters, the native promoter sequences may be used. Such constructs would change expression levels of the RAP2.7 or amounts of the VGT1 regulatory element present in the plant or plant cell. Thus, the phenotype of the plant or plant cell is altered.

The termination region may be native with the transcriptional initiation region, may be native with the operably linked DNA sequence of interest, or may be derived from another source. Convenient termination regions are available from the Ti-plasmid of *A. tumefaciens*, such as the octopine synthase and nopaline synthase termination regions. See also Guerineau et al. (1991) *Mol. Gen. Genet.* 262:141-144; Proudfoot (1991) *Cell* 64:671-674; Sanfacon et al. (1991) *Genes Dev.* 5:141-149; Mogen et al. (1990) *Plant Cell* 2:1261-1272; Munroe et al. (1990) *Gene* 91:151-158; Ballas et al. (1989) *Nucleic Acids Res.* 17:7891-7903; and Joshi et al. (1987) *Nucleic Acid Res.* 15:9627-9639. Where appropriate, the gene(s) may be optimized for increased expression in the transformed plant. That is, the genes can be synthesized using plant-preferred codons for improved expression. Methods are available in the art for synthesizing plant-preferred genes. See, for example, U.S. Pat. Nos. 5,380,831, and 5,436,391, and Murray et al. (1989) *Nucleic Acids Res.* 17:477-498, herein incorporated by reference.

Additional sequence modifications are known to enhance gene expression in a cellular host. These include elimination of sequences encoding spurious polyadenylation signals, exon-intron splice site signals, transposon-like repeats, and other such well characterized sequences that may be deleterious to gene expression. The G-C content of the sequence may be adjusted to enhance expression in a given host cell. When possible, the sequence is modified to avoid predicted hairpin secondary mRNA structures.

The expression cassettes/nucleotide constructs may additionally contain 5' leader sequences in the expression cassette construct. Such leader sequences can act to enhance translation. Translation leaders are known in the art and include: picornavirus leaders, for example, EMCV leader (Encephalomyocarditis 5' noncoding region) (Elroy-Stein et al. (1989) *Proc. Nat'l. Acad.* Sci. USA 86:6126-6130); potyvirus leaders, for example, TEV leader (Tobacco Etch Virus) (Allison et al. (1986); MDMV leader (Maize Dwarf Mosaic Virus); *Virology* 154:9-20), and human immunoglobulin heavy-chain binding protein (BiP), (Macejak et al. (1991) *Nature* 353:90-94); untranslated leader from the coat protein mRNA of alfalfa mosaic virus (AMV RNA 4) (Jobling et al. (1987) *Nature* 325:622625); tobacco mosaic virus leader (TMV) (Gallie et al. (1989) in *Molecular Biology of RNA*, ed. Cech (Liss, New York), pp. 237-256); and maize chlorotic mottle virus leader (MCMV) (Lommel et al. (1991) Virology 81:382-385). See also, Della-Cioppa et al. (1987) *Plant Physiol.* 84:965-968. Other methods known to enhance translation can also be utilized, for example, introns, and the like.

In those instances where it is desirable to have the expressed product of the heterologous nucleotide sequence of interest directed to a particular organelle, such as the chloroplast or mitochondrion, or secreted at the cell's surface or extracellularly, the expression cassette may further comprise a coding sequence for a transit peptide. Such transit peptides are well known in the art and include, but are not limited to, the transit peptide for the acyl carrier protein, the small subunit of RUBISCO, plant EPSP synthase, and the like.

In preparing the expression cassette/nucleotide construct, the various DNA fragments may be manipulated so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g., transitions and transversions, may be involved.

Generally, the expression cassette/nucleotide construct will comprise a selectable marker gene for the selection of transformed cells. Selectable marker genes are utilized for the selection of transformed cells or tissues. Marker genes include genes encoding antibiotic resistance, such as those encoding neomycin phosphotransferase II (NEO) and hygromycin phosphotransferase (HPT), as well as genes conferring resistance to herbicidal compounds, such as glufosinate ammonium, bromoxynil, imidazolinones, and 2,4-dichlorophenoxyacetate (2,4-D). See generally, Yarranton (1992) *Curr. Opin. Biotech.* 3:506-511; Christopherson et al. (1992) *Proc. Nad. Acad. Sci. USA* 89:6314-6318; Yao et al. (1992) *Cell* 71:63-72; Reznikoff (1992) *Mol. Microbiol.* 6:2419-2422; Barkley et al. (1980) in *The Operon*, pp. 177-220; Hu et al. (1987) *Cell* 48:555-566; Brown et al. (1987) *Cell* 49:603-612; Figge et al. (1988) *Cell* 52:713-722; Deuschle et al. (1989) *Proc. Nad. Acad. Sci. USA* 86:5400-5404; Fuerst et al. (1989) *Proc. Nad. Acad. Sci. USA* 86:2549-2553; Deuschle et al. (1990) *Science* 248:480-483; Gossen (1993) Ph.D. Thesis, University of Heidelberg; Reines et al. (1993) *Proc. Nad. Acad. Sci. USA* 90:1917-1921; Labow et al. (1990) *Mol. Cell. Biol.* 10:3343-3356; Zambretti et al. (1992) *Proc. Nad. Acad. Sci. USA* 89:3952-3956; Baim et al. (1991) *Proc. Nad. Acad. Sci. USA* 88:5072-5076; Wyborski et al. (1991) *Nucleic Acids Res.* 19:4647-4653; Hillenand-Wissman (1989) *Topics Mol. Struc. Biol.* 10:143-162; Degenkolb et al. (1991) *Antimicrob. Agents Chemother.* 35:1591-1595; Kleinschnidt et al. (1988) *Biochemisty* 27:1094-1104; Bonin (1993) Ph.D. Thesis, University of Heidelberg; Gossen et al. (1992) *Proc. Nad. Acad. Sci. USA* 89:5547-5551; Oliva et al. (1992) *Antimicrob. Agents Chemother.* 36:913-919; Hlavka et al. (1985) *Handbook of Experimental Pharmacology*, Vol. 78 (Springer-Verlag, Berlin); Gill et al. (1988) *Nature* 334:721-724. Such disclosures are herein incorporated by reference.

The above list of selectable marker genes is not meant to be limiting. Any selectable marker gene can be used in the present invention. A number of promoters can be used in the practice of the invention. The promoters can be selected based on the desired outcome. That is, the nucleic acids can be combined with constitutive, tissue-preferred, or other promoters for expression in plants. Constitutive promoters include, for example, the core promoter of the Rsyn7 promoter and other constitutive promoters disclosed in WO 99/43838 and U.S. Pat. No. 6,072,050; the core CaMV 35S promoter (Odell et al. (1985) *Nature* 313:810-812); rice actin (McElroy et al. (1990) *Plant Cell* 2:163-171); ubiquitin (Christensen et al. (1989) *Plant Mol. Biol.* 12:619-632 and Christensen et al. (1992) *Plant Mol. Biol.* 18:675-689); pEMU (Last et al. (1991) *Theor. Appl. Genet.* 81:581-588); MAS (Velten et al. (1984) *EMBO J.* 3:2723-2730); ALS promoter (U.S. Pat. No. 5,659,026), and the like. Other constitutive promoters include, for example, U.S. Pat. Nos. 5,608,149; 5,608,144; 5,604,121; 5,569,597; 5,466,785; 5,399,680; 5,268,463; 5,608,142; and 6,177,611.

Chemical-regulated promoters can be used to modulate the expression of a gene in a plant through the application of an exogenous chemical regulator. Depending upon the objective, the promoter may be a chemical-inducible promoter, where application of the chemical induces gene expression, or a chemical-repressible promoter, where application of the chemical represses gene expression. Chemical-inducible promoters are known in the art and include, but are not limited to: the maize In2-2 promoter, which is activated by benzenesulfonamide herbicide safeners; the maize GST promoter, which is activated by hydrophobic electrophilic compounds that are used as pre-emergent herbicides; and the tobacco PR-1 a promoter, which is activated by salicylic acid. Other chemical-regulated promoters of interest include steroid-responsive promoters. See, for example, the glucocorticoid-inducible promoter in Schena et al. (1991) *Proc. Nad. Acad. Sci. USA* 88:10421-10425 and McNellis et al. (1998) *Plant J.* 14(2):247-257) and tetracycline-inducible and tetracycline-repressible promoters (for example, Gatz et al. (1991) Mol. Gen. Genet. 227:229-237, and U.S. Pat. Nos. 5,814,618 and 5,789,156), herein incorporated by reference.

Tissue-preferred promoters can be utilized to target enhanced gene expression within a particular plant tissue. Tissue-preferred promoters include Yamamoto et al. (1997) Plant J 12(2):255-265; Kawamata et al. (1997) Plant Cell Physiol. 38(7):792-803; Hansen et al. (1997) *Mol. Gen. Genet.* 254(3):337-343; Russell et al. (1997) Transgenic Res. 6(2):157-168; Rinehart et al. (1996) Plant Physiol. 112(3): 1331-1341; Van Camp et al. (1996) Plant *Physiol.* 112(2): 525-535; Canevascini et al. (1996) Plant *Physiol.* 112(2):513-524; Yamamoto et al. (1994) Plant Cell Physiol. 35(5):773-

778; Lam (1994) Results Probl. Cell Differ. 20:181-196; Orozco et al. (1993) Plant Mol. Biol. 23(6):1129-1138; Matsuoka et al. (1993) Proc Natl. Acad. Sci. USA 90(20):9586-9590; and Guevara-Garcia et al. (1993) Plant J. 4(3):495-505. Such promoters can be modified, if necessary, for weak expression. Leaf-specific promoters are known in the art. See, for example, Yamamoto et al. (1997) Plant J. 12(2):255-265; Kwon et al. (1994) Plant Physiol. 105:357-67; Yamamoto et al. (1994) Plant Cell Physiol. 35(5):773-778; Gotor et al. (1993) Plant J 3:509-18; Orozco et al. (1993) Plant Mol. Biol. 23(6):1129-1138; and Matsuoka et al. (1993) Proc. Nad. Acad. Sci. USA 90(20):9586-9590.

Where low level expression is desired, weak promoters will be used. Generally, by "weak promoter" is intended a promoter that drives expression of a coding sequence at a low level. By low level is intended at levels of about 1/1000 transcripts to about 1/100,000 transcripts to about 1/500,000 transcripts per cell. Alternatively, it is recognized that weak promoters also include promoters that are expressed in only a few cells and not in others to give a total low level of expression. Where a promoter is expressed at unacceptably high levels, portions of the promoter sequence can be deleted or modified to decrease expression levels. Such weak constitutive promoters include, for example, the core promoter of the Rsyn7 promoter (WO 99/43838 and U.S. Pat. No. 6,072,050), the core 35S CaMV promoter, and the like. Other constitutive promoters include, for example, U.S. Pat. Nos. 5,608,149; 5,608,144; 5,604,121; 5,569,597; 5,466,785; 5,399,680; 5,268,463; and 5,608,142. See also, U.S. Pat. No. 6,177,611, herein incorporated by reference.

As used herein, "vector" refers to a molecule such as a plasmid, cosmid or bacterial phage for introducing a nucleotide construct and/or expression cassette into a host cell. Cloning vectors typically contain one or a small number of restriction endonuclease recognition sites at which foreign nucleotide sequences can be inserted in a determinable fashion without loss of essential biological function of the vector, as well as a marker gene that is suitable for use in the identification and selection of cells transformed with the cloning vector. Marker genes typically include genes that provide tetracycline resistance, hygromycin resistance or ampicillin resistance.

The methods of the invention involve introducing a nucleotide construct into a plant. By "introducing" is intended presenting to the plant the nucleotide construct in such a manner that the construct gains access to the interior of a cell of the plant. The methods of the invention do not depend on a particular method for introducing a nucleotide construct to a plant, only that the nucleotide construct gains access to the interior of at least one cell of the plant. Methods for introducing nucleotide constructs into plants are known in the art including, but not limited to, stable transformation methods, transient transformation methods, and virus-mediated methods.

By "stable transformation" is intended that the nucleotide construct introduced into a plant integrates into the genome of the plant and is capable of being inherited by progeny thereof. By "transient transformation" is intended that a nucleotide construct introduced into a plant does not integrate into the genome of the plant.

The nucleotide constructs of the invention may be introduced into plants by contacting plants with a virus or viral nucleic acids. Generally, such methods involve incorporating a nucleotide construct of the invention within a viral DNA or RNA molecule. It is recognized that the RAP2.7 protein of the invention may be initially synthesized as part of a viral polyprotein, which later may be processed by proteolysis in vivo or in vitro to produce the desired recombinant protein. Further, it is recognized that promoters of the invention also encompass promoters utilized for transcription by viral RNA polymerases. Methods for introducing nucleotide constructs into plants and expressing a protein encoded therein, involving viral DNA or RNA molecules, are known in the art. See, for example, U.S. Pat. Nos. 5,889,191, 5,889,190, 5,866,785, 5,589,367 and 5,316,931, herein incorporated by reference.

A variety of other transformation protocols are contemplated in the present invention. Transformation protocols as well as protocols for introducing nucleotide sequences into plants may vary depending on the type of plant or plant cell, i.e., monocot or dicot, targeted for transformation. Suitable methods of introducing nucleotide sequences into plant cells and subsequent insertion into the plant genome include microinjection (Crossway et al. (1986) Biotechniques 4:320-334), electroporation (Riggs et al. (1986) Proc. Nad. Acad. Sci. USA 83:5602-5606, Agrobacterium-mediated transformation (Townsend et al., U.S. Pat. No. 5,563,055; Zhao et al., U.S. Pat. No. 5,981,840), direct gene transfer (Paszkowski et al. (1984) EMBO J. 3:2717-2722), and ballistic particle acceleration (see, for example, Sanford et al., U.S. Pat. No. 4,945,050; Tomes et al., U.S. Pat. No. 5,879,918; Tomes et al., U.S. Pat. No. 5,886,244; Bidney et al., U.S. Pat. No. 5,932,782; Tomes et al. (1995) "Direct DNA Transfer into Intact Plant Cells via Microprojectile Bombardment," in Plant Cell, Tissue, and Organ Culture: Fundamental Methods, eds. Gamborg and Phillips (Springer-Verlag, Berlin); McCabe et al. (1988) Biotechnology 6:923-926); and Lecl transformation (WO 00/28058, published May 18, 2000). Also see Weissinger et al. (1988) Ann. Rev. Genet. 22:421-477; Sanford et al. (1987) Particulate Science and Technology 5:27-37 (onion); Christou et al. (1988) Plant Physiol. 87:671-674 (soybean); McCabe et al. (1988) Bio/Technology 6:923-926 (soybean); Finer and McMullen (1991) In Vitro Cell Dev. Biol. 27P:175-182 (soybean); Singh et al. (1998) Theor. Appl. Genet. 96:319-324 (soybean); Datta et al. (1990) Biotechnology 8:736-740 (rice); Klein et al. (1988) Proc. Nad. Acad. Sci. USA 85:43054309 (maize); Klein et al. (1988) Biotechnology 6:559-563 (maize); Tomes, U.S. Pat. No. 5,240,855; Buising et al., U.S. Pat. Nos. 5,322,783 and 5,324,646; Tomes et al. (1995) 'Direct DNA Transfer into Intact Plant Cells via Microprojectile Bombardment," in Plant Cell, Tissue, and Organ Culture Fundamental Methods, ed. Gamborg (Springer-Verlag, Berlin) (maize); Klein et al. (1988) Plant Physiol. 91:440-444 (maize); Fromm et al. (1990) Biotechnology 8:833-839 (maize); Hooykaas-Van Slogteren et al. (1984) Nature (London) 311:763-764; Bowen et al., U.S. Pat. No. 5,736,369 (cereals); Bytebier et al. (1987) Proc. Nad. Acad. Sci. USA 84:5345-5349 (Liliaceae); De Wet et al. (1985) in The Experimental Manipulation of Ovule Tissues, ed. Chapman et al. (Longman, N.Y.), pp. 197-209 (pollen); Kaeppler et al. (1990) Plant Cell Reports 9:415-418 and Kaeppler et al. (1992) Theor. Appl. Genet. 84:560-566 (whisker-mediated transformation); D'Halluin et al. (1992) Plant Cell 4:1495-1505 (electroporation); Li et al. (1993) Plant Cell Reports 12:250-255 and Christou and Ford (1995) Annals of Botany 75:407-413 (rice); Osjoda et al. (1996) Nature Biotechnology 14:745-750 (maize via Agrobacterium tumefaciens); all of which are herein incorporated by reference.

The cells that have been transformed may be grown into plants in accordance with conventional ways. See, for example, McCormick et al. (1986) Plant Cell Reports 5:81-84. These plants may then be grown, and either pollinated with the same transformed strain or different strains, and the resulting hybrid having constitutive expression of the desired phenotypic characteristic identified. Two or more generations may be grown to ensure that constitutive expression of the desired phenotypic characteristic is stably maintained and inherited and then seeds harvested to ensure constitutive expression of the desired phenotypic characteristic has been achieved.

The present invention may be used for transformation of any plant species, including, but not limited to, monocots and dicots. Examples of plant species of interest include, but are not limited to, corn (*Zea mays*), *Brassica* spp. (e.g., *B. napus, B. rapa, B. juncea*), particularly those *Brassica* species useful as sources of seed oil, alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassava (*Manihot esculenta*), coffee (*Coffea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), sugarcane (*Saccharum* spp.), oats, barley, vegetables, ornamentals, and conifers.

Vegetables include tomatoes (*Lycopersicon esculentum*), lettuce (e.g., *Lactuca sativa*), green beans (*Phaseolus vulgaris*), lima beans (*Phaseolus limensis*), peas (*Lathyrus* spp.), and members of the genus *Cucumis* such as cucumber (*C. sativus*), cantaloupe (*C. cantalupensis*), and musk melon (*C. melo*). Ornamentals include azalea (*Rhododendron* spp.), hydrangea (*Macrophylla hydrangea*), hibiscus (*Hibiscus rosasanensis*), roses (*Rosa* spp.), tulips (*Tulipa* spp.), daffodils (*Narcissus* spp.), petunias (*Petunia hybrida*), carnation (*Dianthus caryophyllus*), poinsettia (*Euphorbia pulcherrima*), and chrysanthemum.

Conifers that may be employed in practicing the present invention include, for example, pines such as loblolly pine (*Pinus taeda*), slash pine (*Pinus elliotii*), ponderosa pine (*Pinus ponderosa*), lodgepole pine (*Pinus contorta*), and Monterey pine (*Pinus radiata*); Douglas-fir (*Pseudotsuga menziesii*); Western hemlock (*Tsuga canadensis*); Sitka spruce (*Picea glauca*); redwood (*Sequoia sempervirens*); true firs such as silver fir (*Abies amabilis*) and balsam fir (*Abies balsamea*); and cedars such as Western red cedar (Thujaplicata) and Alaska yellow cedar (*Chamaecyparis nootkatensis*). Plants of the present invention may be crop plants (for example, alfalfa, sunflower, *Brassica*, cotton, safflower, peanut, sorghum, wheat, millet, tobacco, etc.), corn or soybean plants.

Plants of particular interest include grain plants that provide seeds of interest, oil-seed plants, and leguminous plants. Seeds of interest include grain seeds, such as corn, wheat, barley, rice, sorghum, rye, etc. Oil-seed plants include cotton, soybean, safflower, sunflower, *Brassica*, maize, alfalfa, palm, coconut, etc. Leguminous plants include beans and peas. Beans include guar, locust bean, fenugreek, soybean, garden beans, cowpea, mungbean, lima bean, fava bean, lentils, chickpea, etc.

It is recognized that with these nucleotide sequences, gene silencing such as antisense constructions complementary to at least a portion of the messenger RNA (mRNA) for RAP2.7 or VGT1 sequences can be constructed. Antisense nucleotides are constructed to hybridize with the corresponding mRNA. Modifications of the antisense sequences may be made as long as the sequences hybridize to and interfere with expression of the corresponding mRNA. In this manner, antisense constructions having 70%, 80%, 85%, 90%, 95% or more sequence identity to the corresponding antisense sequences may be used. Furthermore, portions of the antisense nucleotides may be used to disrupt the expression of the target gene. Generally, sequences of at least 50 nucleotides, 100 nucleotides, 200 nucleotides, or greater may be used.

Gene silencing refers to posttranscriptional interference with gene expression. Techniques such as antisense, co-suppression, and RNA interference (RNAi), for example, have been shown to be effective in gene silencing. (For reviews, see Arndt and Rank, Genome 40(6):785-797, 1997; Turner and Schuch, Journal of Chemical Technology and Biotechnology 75(10):869-882, 2000; Klink and Wolniak, Journal of Plant Growth Regulation 19(4):371-384, 2000)

Antisense technology can be used to control gene expression through antisense DNA or RNA or through double- or triple-helix formation. Antisense techniques are discussed, for example, in—Okano, J. Neurochem. 56: 560 (1991); OLIGODEOXYNUCLEOTIDES AS ANTISENSE INHIBITORS OF GENE EXPRESSION, CRC Press, Boca Raton, Fla. (1988). Triple helix formation is discussed in, for instance Lee et al., *Nucleic Acids Research* 6:3073 (1979); Cooney et al., *Science* 241:456 (1988); and Dervan et al., *Science* 251: 1360 (1991). The methods are based on binding of a polynucleotide to a complementary DNA or RNA. For example, the 5' coding portion of a polynucleotide that encodes the mature polypeptide of the present invention may be used to design an antisense RNA oligonucleotide of from about 10 to 40 base pairs in length. A DNA oligonucleotide is designed to be complementary to a region of the gene involved in transcription, thereby preventing transcription and the production of cytokinin biosynthetic enzymes. The antisense RNA oligonucleotide hybridizes to the mRNA in vivo and blocks translation of the mRNA molecule into cytokinin biosynthetic enzymes. The oligonucleotides described above can also be delivered to cells such that the antisense RNA or DNA may be expressed in vivo to inhibit production of cytokinin biosynthetic enzymes. The DNAs of this invention may also be employed to co-suppress or silence the cytokinin metabolic enzyme genes; for example, as described in PCT Patent Application Publication WO 98/36083.

The RAP 2.7 nucleotide sequence operably linked to the regulatory elements herein can be an antisense sequence for a targeted gene. By "antisense DNA nucleotide sequence" is intended a sequence that is in inverse orientation to the 5'-to-3' normal orientation of that nucleotide sequence. When delivered into a plant cell, expression of the antisense DNA sequence prevents normal expression of the DNA nucleotide sequence for the targeted gene. The antisense nucleotide sequence encodes an RNA transcript that is complementary to and capable of hybridizing with the endogenous messenger RNA (mRNA) produced by transcription of the DNA nucleotide sequence for the targeted gene. In this case, production of the native protein encoded by the targeted gene is inhibited to achieve a desired phenotypic response. Thus the regulatory sequences disclosed herein can be operably linked to antisense DNA sequences to reduce or inhibit expression of a native protein in the plant seed.

It is also recognized that the level and/or activity of the polypeptide may be modulated by employing a polynucleotide that is not capable of directing, in a transformed plant, the expression of a protein or an RNA. For example, the polynucleotides of the invention may be used to design polynucleotide constructs that can be employed in methods for altering or mutating a genomic nucleotide sequence in an organism. Such polynucleotide constructs include, but are not limited to, RNA:DNA vectors, RNA:DNA mutational vectors, RNA:DNA repair vectors, mixed-duplex oligonucleotides, self-complementary RNA:DNA oligonucleotides, and recombinogenic oligonucleobases. Such nucleotide constructs and methods of use are known in the art. See, U.S. Pat. Nos. 5,565,350; 5,731,181; 5,756,325; 5,760,012; 5,795,972; and 5,871,984; all of which are herein incorporated by reference. See also, WO 98/49350, WO 99/07865, WO 99/25821, and Beetham et al. (1999) Proc. Natl. Acad. Sci. USA 96:8774-8778; herein incorporated by reference. It is therefore recognized that methods of the present invention do not depend on the incorporation of the entire polynucleotide into the genome, only that the plant or cell thereof is altered as a result of the introduction of the polynucleotide into a cell. In one embodiment of the invention, the genome may be altered following the introduction of the polynucleotide into a cell. For example, the polynucleotide, or any part thereof, may incorporate into the genome of the plant. Alterations to the genome of the present invention include, but are not limited to, additions, deletions, and substitutions of nucleotides into the genome. While the methods of the present invention do not depend on additions, deletions, and substitutions of any particular number of nucleotides, it is recognized that such additions, deletions, or substitutions comprises at least one nucleotide.

Methods are provided to reduce or eliminate the activity of a RAP2.7 polypeptide of the invention by transforming a plant cell with an expression cassette that expresses a polynucleotide that inhibits the expression of the RAP2.7 polypeptide. The polynucleotide may inhibit the expression of the Rap2.7 polypeptide directly, by preventing translation of the RAP2.7 messenger RNA, or indirectly, by encoding a polypeptide that inhibits the transcription or translation of a RAP2.7 gene encoding a RAP2.7 polypeptide. Methods for inhibiting or eliminating the expression of a gene in a plant are well known in the art, and any such method may be used in the present invention to inhibit the expression of a RAP2.7 polypeptide.

In some embodiments of the present invention, a plant is transformed with an expression cassette that is capable of expressing a polynucleotide that inhibits the expression of a RAP2.7 polypeptide of the invention. The term "expression" as used herein refers to the biosynthesis of a gene product, including the transcription and/or translation of said gene product. For example, for the purposes of the present invention, an expression cassette capable of expressing a polynucleotide that inhibits the expression of at least one RAP2.7 polypeptide is an expression cassette capable of producing an RNA molecule that inhibits the transcription and/or translation of at least one RAP2.7 polypeptide of the invention. The "expression" or "production" of a protein or polypeptide from a DNA molecule refers to the transcription and translation of the coding sequence to produce the protein or polypeptide, while the "expression" or "production" of a protein or polypeptide from an RNA molecule refers to the translation of the RNA coding sequence to produce the protein or polypeptide.

Examples of polynucleotides that inhibit the expression of a RAP2.7 polypeptide are given below.

i. Sense Suppression/Cosuppression

In some embodiments of the invention, inhibition of the expression of a RAP2.7 polypeptide may be obtained by sense suppression or cosuppression. For cosuppression, an expression cassette is designed to express an RNA molecule corresponding to all or part of a messenger RNA encoding a RAP2.7 polypeptide in the "sense" orientation. Over expression of the RNA molecule can result in reduced expression of the native gene. Accordingly, multiple plant lines transformed with the cosuppression expression cassette are screened to identify those that show the greatest inhibition of RAP2.7 polypeptide expression.

The polynucleotide used for cosuppression may correspond to all or part of the sequence encoding the RAP2.7 polypeptide, all or part of the 5' and/or 3' untranslated region of a RAP2.7 polypeptide transcript, or all or part of both the coding sequence and the untranslated regions of a transcript encoding a RAP2.7 polypeptide. In some embodiments where the polynucleotide comprises all or part of the coding region for the RAP2.7 polypeptide, the expression cassette is designed to eliminate the start codon of the polynucleotide so that no protein product will be translated.

Cosuppression may be used to inhibit the expression of plant genes to produce plants having undetectable protein levels for the proteins encoded by these genes. See, for example, Broin et al. (2002) Plant Cell 14:1417-1432. Cosuppression may also be used to inhibit the expression of multiple proteins in the same plant. See, for example, U.S. Pat. No. 5,942,657. Methods for using cosuppression to inhibit the expression of endogenous genes in plants are described in Flavell et al. (1994) Proc. Natl. Acad. Sci. USA 91:3490-3496; Jorgensen et al. (1996) Plant Mol. Biol. 31:957-973; Johansen and Carrington (2001) Plant Physiol. 126:930-938; Broin et al. (2002) Plant Cell 14:1417-1432; Stoutjesdijk et al. (2002) Plant Physiol. 129:1723-1731; Yu et al. (2003) Phytochemistry 63:753-763; and U.S. Pat. Nos. 5,034,323, 5,283,184, and 5,942,657; each of which is herein incorporated by reference. The efficiency of cosuppression may be increased by including a poly-dT region in the expression cassette at a position 3' to the sense sequence and 5' of the polyadenylation signal. See, U.S. Patent Publication No. 2002004-8814, herein incorporated by reference. Typically, such a nucleotide sequence has substantial sequence identity to the sequence of the transcript of the endogenous gene, optimally greater than about 65% sequence identity, more optimally greater than about 85% sequence identity, most optimally greater than about 95% sequence identity. See, U.S. Pat. Nos. 5,283,184 and 5,034,323; herein incorporated by reference.

ii. Antisense Suppression

In some embodiments of the invention, inhibition of the expression of the RAP2.7 polypeptide may be obtained by antisense suppression. For antisense suppression, the expression cassette is designed to express an RNA molecule complementary to all or part of a messenger RNA encoding the RAP2.7 polypeptide. Over expression of the antisense RNA molecule can result in reduced expression of the native gene. Accordingly, multiple plant lines transformed with the antisense suppression expression cassette are screened to identify those that show the greatest inhibition of RAP2.7 polypeptide expression.

The polynucleotide for use in antisense suppression may correspond to all or part of the complement of the sequence encoding the RAP2.7 polypeptide, all or part of the complement of the 5' and/or 3' untranslated region of the RAP2.7 transcript, or all or part of the complement of both the coding sequence and the untranslated regions of a transcript encoding the RAP2.7 polypeptide. In addition, the antisense polynucleotide may be fully complementary (i.e., 100% identical to the complement of the target sequence) or partially complementary (i.e., less than 100% identical to the complement of the target sequence) to the target sequence. Antisense suppression may be used to inhibit the expression of multiple proteins in the same plant. See, for example, U.S. Pat. No. 5,942,657. Furthermore, portions of the antisense nucleotides may be used to disrupt the expression of the target gene. Generally, sequences of at least 50 nucleotides, 100 nucleotides, 200 nucleotides, 300, 400, 450, 500, 550, or greater may be used. Methods for using antisense suppression to inhibit the expression of endogenous genes in plants are described, for example, in Liu et al. (2002) *Plant Physiol.* 129:1732-1743 and U.S. Pat. Nos. 5,759,829 and 5,942,657, each of which is herein incorporated by reference. Efficiency of antisense suppression may be increased by including a poly-dT region in the expression cassette at a position 3' to the antisense sequence and 5' of the polyadenylation signal. See, U.S. Patent Publication No. 20020048814, herein incorporated by reference.

iii. Double-Stranded RNA Interference

In some embodiments of the invention, inhibition of the expression of a RAP2.7 polypeptide may be obtained by double-stranded RNA (dsRNA) interference. For dsRNA interference, a sense RNA molecule like that described above for cosuppression and an antisense RNA molecule that is fully or partially complementary to the sense RNA molecule are expressed in the same cell, resulting in inhibition of the expression of the corresponding endogenous messenger RNA.

Expression of the sense and antisense molecules can be accomplished by designing the expression cassette to comprise both a sense sequence and an antisense sequence. Alternatively, separate expression cassettes may be used for the sense and antisense sequences. Multiple plant lines transformed with the dsRNA interference expression cassette or expression cassettes are then screened to identify plant lines that show the greatest inhibition of RAP2.7 polypeptide expression. Methods for using dsRNA interference to inhibit the expression of endogenous plant genes are described in Waterhouse et al. (1998) *Proc. Natl. Acad. Sci. USA* 95:13959-13964, Liu et al. (2002) *Plant Physiol.* 129:1732-1743, and WO 99/49029, WO 99/53050, WO 99/61631, and WO 00/49035; each of which is herein incorporated by reference.

iv. Hairpin RNA Interference and Intron-Containing Hairpin RNA Interference

In some embodiments of the invention, inhibition of the expression of one or a RAP2.7 polypeptide may be obtained by hairpin RNA (hpRNA) interference or intron-containing hairpin RNA (ihpRNA) interference. These methods are highly efficient at inhibiting the expression of endogenous genes. See, Waterhouse and Helliwell (2003) *Nat. Rev. Genet.* 4:29-38 and the references cited therein.

For hpRNA interference, the expression cassette is designed to express an RNA molecule that hybridizes with itself to form a hairpin structure that comprises a single-stranded loop region and a base-paired stem. The base-paired stem region comprises a sense sequence corresponding to all or part of the endogenous messenger RNA encoding the gene whose expression is to be inhibited, and an antisense sequence that is fully or partially complementary to the sense sequence. Thus, the base-paired stem region of the molecule generally determines the specificity of the RNA interference. hpRNA molecules are highly efficient at inhibiting the expression of endogenous genes, and the RNA interference they induce is inherited by subsequent generations of plants. See, for example, Chuang and Meyerowitz (2000) *Proc. Natl. Acad. Sci. USA* 97:4985-4990; Stoutjesdijk et al. (2002) *Plant Physiol.* 129:1723-1731; and Waterhouse and Helliwell (2003) *Nat. Rev. Genet.* 4:29-38. Methods for using hpRNA interference to inhibit or silence the expression of genes are described, for example, in Chuang and Meyerowitz (2000) *Proc. Natl. Acad. Sci. USA* 97:4985-4990; Stoutjesdijk et al. (2002) *Plant Physiol.* 129:1723-1731; Waterhouse and Helliwell (2003) *Nat. Rev. Genet.* 4:29-38; Pandolfini et al. *BMC Biotechnology* 3:7, and U.S. Patent Publication No. 20030175965; each of which is herein incorporated by reference. A transient assay for the efficiency of hpRNA constructs to silence gene expression in vivo has been described by Panstruga et al. (2003) *Mol. Biol. Rep.* 30:135-140, herein incorporated by reference.

For ihpRNA, the interfering molecules have the same general structure as for hpRNA, but the RNA molecule additionally comprises an intron that is capable of being spliced in the cell in which the ihpRNA is expressed. The use of an intron minimizes the size of the loop in the hairpin RNA molecule following splicing, and this increases the efficiency of interference. See, for example, Smith et al. (2000) *Nature* 407: 319-320. In fact, Smith et al. show 100% suppression of endogenous gene expression using ihpRNA-mediated interference. Methods for using ihpRNA interference to inhibit the expression of endogenous plant genes are described, for example, in Smith et al. (2000) *Nature* 407:319-320; Wesley et al. (2001) *Plant J.* 27:581-590; Wang and Waterhouse (2001) *Curr. Opin. Plant Biol.* 5:146-150; Waterhouse and Helliwell (2003) *Nat. Rev. Genet.* 4:29-38; Helliwell and Waterhouse (2003) *Methods* 30:289-295, and U.S. Patent Publication No. 20030180945, each of which is herein incorporated by reference.

The expression cassette for hpRNA interference may also be designed such that the sense sequence and the antisense sequence do not correspond to an endogenous RNA. In this embodiment, the sense and antisense sequence flank a loop sequence that comprises a nucleotide sequence corresponding to all or part of the endogenous messenger RNA of the target gene. Thus, it is the loop region that determines the specificity of the RNA interference. See, for example, WO 02/00904, herein incorporated by reference.

v. Amplicon-Mediated Interference

Amplicon expression cassettes comprise a plant virus-derived sequence that contains all or part of the target gene but generally not all of the genes of the native virus. The viral sequences present in the transcription product of the expression cassette allow the transcription product to direct its own replication. The transcripts produced by the amplicon may be either sense or antisense relative to the target sequence (i.e., the messenger RNA for the RAP2.7 polypeptide). Methods of using amplicons to inhibit the expression of endogenous plant genes are described, for example, in Angell and Baulcombe (1997) *EMBO J.* 16:3675-3684, Angell and Baulcombe (1999) *Plant J.* 20:357-362, and U.S. Pat. No. 6,646,805, each of which is herein incorporated by reference.

vi. Ribozymes

In some embodiments, the polynucleotide expressed by the expression cassette of the invention is catalytic RNA or has ribozyme activity specific for the messenger RNA of the RAP2.7 polypeptide. Thus, the polynucleotide causes the degradation of the endogenous messenger RNA, resulting in reduced expression of the RAP2.7 polypeptide. This method is described, for example, in U.S. Pat. No. 4,987,071, herein incorporated by reference.

vii. Small Interfering RNA or Micro RNA

In some embodiments of the invention, inhibition of the expression of a RAP2.7 polypeptide may be obtained by RNA interference by expression of a gene encoding a micro RNA (miRNA). miRNAs are regulatory agents consisting of about 22 ribonucleotides. miRNA are highly efficient at inhibiting the expression of endogenous genes. See, for example Javier et al. (2003) *Nature* 425: 257-263, herein incorporated by reference.

For miRNA interference, the expression cassette is designed to express an RNA molecule that is modeled on an endogenous miRNA gene. The miRNA gene encodes an RNA that forms a hairpin structure containing a 22-nucleotide sequence that is complementary to another endogenous gene (target sequence). For suppression of RAP2.7 expression, the 22-nucleotide sequence is selected from a RAP2.7 transcript sequence and contains 22 nucleotides of said RAP2.7 sequence in sense orientation and 21 nucleotides of a corresponding antisense sequence that is complementary to the sense sequence. miRNA molecules are highly efficient at inhibiting the expression of endogenous genes, and the RNA interference they induce is inherited by subsequent generations of plants.

The availability of reverse genetics systems, which are well-known in the art, makes the generation and isolation of down-regulated or null mutants feasible, given the availability of a defined nucleic acid sequence, as provided herein. One such system (the Trait Utility System for Corn, i.e., TUSC) is based on successful systems from other organisms (Ballinger et al., Proc. Natl. Acad. Sci. USA, 86, 9402-9406 (1989); Kaiser et al. (1990), Proc. Natl. Acad. Sci. USA, 87, 1686-1690; and Rushforth et al., Mol. Cell. Biol., 13, 902-910 (1993)). The central feature of the system is to identify Mu transposon insertions within a DNA sequence of interest in anticipation that at least some of these insertion alleles will be mutants. See U.S. Pat. Nos. 6,300,542 and 5,962,764. To develop the system, DNA was collected from a large population of Mutator transposon stocks that were then self-pollinated to produced F2 seed. To find Mu transposon insertions within a specific DNA sequence, the collection of DNA samples is screened via PCR using a gene-specific primer and a primer that anneals to the inverted repeats of Mu transposons. A PCR product is expected only when the template DNA comes from a plant that contains a Mu transposon insertion within the target gene. Once such a DNA sample is identified, F2 seed from the corresponding plant is screened for a transposon insertion allele. Transposon insertion mutations of the an1 gene have been obtained via the TUSC procedure (Bensen et al. (1995)). This system is applicable to other plant species, at times modified in accordance with knowledge and skills reasonably attributed to ordinary artisans.

The use of the term "nucleotide constructs" herein is not intended to limit the present invention to nucleotide constructs comprising DNA. Those of ordinary skill in the art will recognize that nucleotide constructs, particularly polynucleotides and oligonucleotides, comprised of ribonucleotides and combinations of ribonucleotides and deoxyribonucleotides may also be employed in the methods disclosed herein. Thus, the nucleotide constructs of the present invention encompass all nucleotide constructs that can be employed in the methods of the present invention for transforming plants including, but not limited to, those comprised of deoxyribonucleotides, ribonucleotides, and combinations thereof. Such deoxyribonucleotides and ribonucleotides include both naturally occurring molecules and synthetic analogues. The nucleotide constructs of the invention also encompass all forms of nucleotide constructs including, but not limited to, single-stranded forms, double-stranded forms, hairpins, stem-and-loop structures, and the like.

Furthermore, it is recognized that the methods of the invention may employ a nucleotide construct that is capable of directing, in a transformed plant, the expression of at least one protein, or at least one RNA, such as, for example, an antisense RNA that is complementary to at least a portion of an mRNA. Typically such a nucleotide construct is comprised of a coding sequence for a protein or an RNA operably linked to 5' and 3' transcriptional regulatory regions. Alternatively, it is also recognized that the methods of the invention may employ a nucleotide construct that is not capable of directing, in a transformed plant, the expression of a protein or an RNA.

In addition, it is recognized that methods of the present invention do not depend on the incorporation of the entire nucleotide construct into the genome. Rather, the methods of the present invention only require that the plant or cell thereof is altered as a result of the introduction of the nucleotide construct into a cell. In one embodiment of the invention, the genome may be altered following the introduction of the nucleotide construct into a cell. or example, the nucleotide construct, or any part thereof, may incorporate into the genome of the plant. Alterations to the genome of the present invention include, but are not limited to, additions, deletions, and substitutions of nucleotides in the genome. While the methods of the present invention do not depend on additions, deletions, or substitutions of any particular number of nucleotides, it is recognized that such additions, deletions, or substitutions comprise at least one nucleotide.

In certain embodiments the nucleic acid sequences of the present invention can be used in combination ("stacked") with other polynucleotide sequences of interest in order to create plants with a desired phenotype. The combinations generated can include multiple copies of any one or more of the polynucleotides of interest. The polynucleotides of the present invention may be stacked with any gene or combination of genes to produce plants with a variety of desired trait combinations, including but not limited to traits desirable for animal feed such as high oil genes (e.g., U.S. Pat. No. 6,232, 529); balanced amino acids (e.g. hordothionins (U.S. Pat. Nos. 5,990,389; 5,885,801; 5,885,802; and 5,703,409); barley high lysine (Williamson et al. (1987) *Eur. J. Biochem.* 165:99-106; and WO 98/20122); and high methionine proteins (Pedersen et al. (1986) *J. Biol. Chem.* 261:6279; Kirihara et al. (1988) *Gene* 71:359; and Musumura et al. (1989) *Plant Mol. Biol.* 12: 123)); increased digestibility (e.g., modified storage proteins (U.S. application Ser. No. 10/053,410, filed Nov. 7, 2001); and thioredoxins (U.S. application Ser. No. 10/005,429, filed Dec. 3, 2001)), the disclosures of which are herein incorporated by reference. The polynucleotides of the present invention can also be stacked with traits desirable for insect, disease or herbicide resistance (e.g., *Bacillus thuringiensis* toxic proteins (U.S. Pat. Nos. 5,366,892; 5,747, 450; 5,737,514; 5,723,756; 5,593,881; Geiser et al (1986) *Gene* 48:109); lectins (Van Damme et al. (1994) *Plant Mol. Biol.* 24:825); fumonisin detoxification genes (U.S. Pat. No. 5,792,931); avirulence and disease resistance genes (Jones et al. (1994) *Science* 266:789; Martin et al. (1993) *Science* 262: 1432; Mindrinos et al. (1994) *Cell* 78:1089); acetolactate synthase (ALS) mutants that lead to herbicide resistance such as the S4 and/or Hra mutations; inhibitors of glutamine synthase such as phosphinothricin or basta (e.g., bar gene); and glyphosate resistance (EPSPS gene)); and traits desirable for processing or process products such as high oil (e.g., U.S. Pat. No. 6,232,529); modified oils (e.g., fatty acid desaturase genes (U.S. Pat. No. 5,952,544; WO 94/11516)); modified starches (e.g., ADPG pyrophosphorylases (AGPase), starch synthases (SS), starch branching enzymes (SBE) and starch debranching enzymes (SDBE)); and polymers or bioplastics (e.g., U.S. Pat. No. 5,602,321; beta-ketothiolase, polyhydroxybutyrate synthase, and acetoacetyl-CoA reductase (Schubert et al. (1988) *J. Bacteriol.* 170:5837-5847) facilitate expression of polyhydroxyalkanoates (PHAs)), the disclosures of which are herein incorporated by reference. One could also combine the polynucleotides of the present invention with polynucleotides affecting agronomic traits such as male sterility (e.g., see U.S. Pat. No. 5,583,210), stalk strength, flowering time, or transformation technology traits such as cell cycle regulation or gene targeting (e.g. WO 99/61619; WO 00/17364; WO 99/25821), the disclosures of which are herein incorporated by reference.

These stacked combinations can be created by any method, including but not limited to cross breeding plants by any conventional or TopCross methodology, or genetic transformation. If the traits are stacked by genetically transforming the plants, the polynucleotide sequences of interest can be combined at any time and in any order. For example, a transgenic plant comprising one or more desired traits can be used as the target to introduce further traits by subsequent transformation. The traits can be introduced simultaneously in a co-transformation protocol with the polynucleotides of interest provided by any combination of transformation cassettes. For example, if two sequences will be introduced, the two sequences can be contained in separate transformation cassettes (trans) or contained on the same transformation cassette (cis). Expression of the sequences of interest can be driven by the same promoter or by different promoters. In certain cases, it may be desirable to introduce a transformation cassette that will suppress the expression of a polynucleotide of interest. This may be accompanied by any combination of other suppression cassettes or overexpression cassettes to generate the desired combination of traits in the plant.

The nucleotide constructs of the invention also encompass nucleotide constructs that may be employed in methods for altering or mutating a genomic nucleotide sequence in an organism, including, but not limited to, chimeric vectors, chimeric mutational vectors, chimeric repair vectors, mixed-duplex oligonucleotides, self-complementary chimeric oligonucleotides, and recombinogenic oligonucleobases. Such nucleotide constructs and methods of use, such as, for example, chimeraplasty, are known in the art. Chimeraplasty involves the use of such nucleotide constructs to introduce site-specific changes into the sequence of genomic DNA within an organism. eg, U.S. Pat. Nos. 5,565,350; 5,731,181; 5,756,325; 5,760,012; 5,795,972; and 5,871,984; all of which are herein incorporated by reference. See also, WO 98/49350, WO 99/07865, WO 99/25821, and Beetham et al. (1999) *Proc. Nad. Acad. Sci. USA* 96:8774-8778; herein incorporated by reference. The following examples are offered by way of illustration and not by way of limitation. All references cited herein are hereby expressly incorporated in their entirety herein by reference.

Other embodiments of the invention include the use of VGT1 and its alternate forms described herein as markers to screen for and identify plants which may have altered maturity. The invention thus relates to genetic markers for plants with altered maturity. The markers represent polymorphic variants of the non-coding regulatory element VGT1 that are associated with RAP2.7 regulation and thus provides a method of genotyping plants to determine those more likely to have flowering time that is altered from wildtype.

Thus, the invention relates to genetic markers and methods of identifying those markers in plants, whereby the plant is more likely to have a maturity that is earlier than normal by means of a mutant VGT1 which does not down regulate RAP2.7 appropriately.

Any method of identifying the presence or absence of these markers may be used, including, for example, single-strand conformation polymorphism (SSCP) analysis, base excision sequence scanning (BESS), RFLP analysis, heteroduplex analysis, denaturing gradient gel electrophoresis, and temperature gradient electrophoresis, allelic PCR, ligase chain reaction direct sequencing, mini sequencing, nucleic acid hybridization, micro-array-type detection of the VGT1 regulatory element.

The following is a general overview of techniques which can be used to assay for the polymorphisms of the invention.

In the present invention, a sample of genetic material is obtained from a plant.

Isolation and Amplification of Nucleic Acid

Samples of genomic DNA are isolated from any convenient source including any suitable cell or tissue sample with intact interphase nuclei or metaphase cells. The cells can be obtained from solid tissue as from a fresh or preserved plant part or from a tissue sample. The sample can contain compounds which are not naturally intermixed with the biological material such as preservatives, anticoagulants, buffers, fixatives, nutrients, antibiotics, or the like.

Methods for isolation of genomic DNA from these various sources are described in, for example, Kirby, *DNA Fingerprinting, An Introduction*, W.H. Freeman & Co. New York (1992). Genomic DNA can also be isolated from cultured primary or secondary cell cultures or from transformed cell lines derived from any of the aforementioned tissue samples.

Samples of RNA can also be used. RNA can be isolated from tissues as described in Sambrook et al., supra. RNA can be total cellular RNA, mRNA, poly A+ RNA, or any combination thereof. For best results, the RNA is purified, but can also be unpurified cytoplasmic RNA. RNA can be reverse transcribed to form DNA which is then used as the amplification template, such that the PCR indirectly amplifies a specific population of RNA transcripts. See, e.g., Sambrook, supra, Kawasaki et al., Chapter 8 in *PCR Technology*, (1992) supra, and Berg et al., *Hum. Genet.* 85:655-658 (1990).

PCR Amplification

The most common means for amplification is polymerase chain reaction (PCR), as described in U.S. Pat. Nos. 4,683,195; 4,683,202; and 4,965,188 each of which is hereby incorporated by reference. Tissues should be roughly minced using a sterile, disposable scalpel and a sterile needle (or two scalpels) in a 5 mm Petri dish. Procedures for removing paraffin from tissue sections are described in a variety of specialized handbooks well known to those skilled in the art.

To amplify a target nucleic acid sequence in a sample by PCR, the sequence must be accessible to the components of the amplification system. Kits for the extraction of high-molecular weight DNA for PCR include a Genomic Isolation Kit A.S.A.P. (Boehringer Mannheim, Indianapolis, Ind.), Genomic DNA Isolation System (GIBCO BRL, Gaithersburg, Md.), Elu-Quik DNA Purification Kit (Schleicher & Schuell, Keene, N. H.), DNA Extraction Kit (Stratagene, LaJolla, Calif.), TurboGen Isolation Kit (Invitrogen, San Diego, Calif.), and the like. Use of these kits according to the manufacturer's instructions is generally acceptable for purification of DNA prior to practicing the methods of the present invention.

The concentration and purity of the extracted DNA can be determined by spectrophotometric analysis of the absorbance of a diluted aliquot at 260 nm and 280 nm. After extraction of the DNA, PCR amplification may proceed. The first step of each cycle of the PCR involves the separation of the nucleic acid duplex formed by the primer extension. Once the strands are separated, the next step in PCR involves hybridizing the separated strands with primers that flank the target sequence. The primers are then extended to form complementary copies of the target strands. For successful PCR amplification, the primers are designed so that the position at which each primer hybridizes along a duplex sequence is such that an extension product synthesized from one primer, when separated from the template (complement), serves as a template for the extension of the other primer. The cycle of denaturation, hybridization, and extension is repeated as many times as necessary to obtain the desired amount of amplified nucleic acid.

In a particularly useful embodiment of PCR amplification, strand separation is achieved by heating the reaction to a sufficiently high temperature for a sufficient time to cause the denaturation of the duplex but not to cause an irreversible denaturation of the polymerase (see U.S. Pat. No. 4,965,188, incorporated herein by reference). Typical heat denaturation involves temperatures ranging from about 80° C. to 105° C. for times ranging from seconds to minutes. Strand separation, however, can be accomplished by any suitable denaturing method including physical, chemical, or enzymatic means. Strand separation may be induced by a helicase, for example, or an enzyme capable of exhibiting helicase activity. For example, the enzyme RecA has helicase activity in the presence of ATP. The reaction conditions suitable for strand separation by helicases are known in the art (see Kuhn Hoffman-Berling, 1978, *CSH-Quantitative Biology*, 43:63-67; and Radding, 1982, *Ann. Rev. Genetics* 16:405-436, each of which is incorporated herein by reference).

Template-dependent extension of primers in PCR is catalyzed by a polymerizing agent in the presence of adequate amounts of four deoxyribonucleotide triphosphates (typically dATP, dGTP, dCTP, and dTTP) in a reaction medium comprised of the appropriate salts, metal cations, and pH buffering systems. Suitable polymerizing agents are enzymes known to catalyze template-dependent DNA synthesis. In some cases, the target regions may encode at least a portion of a protein expressed by the cell. In this instance, mRNA may be used for amplification of the target region. Alternatively, PCR can be used to generate a cDNA library from RNA for further amplification, the initial template for primer extension is RNA. Polymerizing agents suitable for synthesizing a complementary, copy-DNA (cDNA) sequence from the RNA template are reverse transcriptase (RT), such as avian myeloblastosis virus RT, Moloney murine leukemia virus RT, or *Thermus thermophilus* (Tth) DNA polymerase, a thermostable DNA polymerase with reverse transcriptase activity marketed by Perkin Elmer Cetus, Inc. Typically, the genomic RNA template is heat degraded during the first denaturation step after the initial reverse transcription step leaving only DNA template. Suitable polymerases for use with a DNA template include, for example, *E. coli* DNA polymerase I or its Klenow fragment, T4 DNA polymerase, Tth polymerase, and Taq polymerase, a heat-stable DNA polymerase isolated from *Thermus aquaticus* and commercially available from Perkin Elmer Cetus, Inc. The latter enzyme is widely used in the amplification and sequencing of nucleic acids. The reaction conditions for using Taq polymerase are known in the art and are described in Gelfand, 1989, *PCR Technology*, supra.

Allele Specific PCR

Allele-specific PCR differentiates between target regions differing in the presence of absence of a variation or polymorphism. PCR amplification primers are chosen which bind only to certain alleles of the target sequence. This method is described by Gibbs, *Nucleic Acid Res.* 17:12427-2448 (1989).

Allele Specific Oligonucleotide Screening Methods

Further diagnostic screening methods employ the allele-specific oligonucleotide (ASO) screening methods, as described by Saiki et al., *Nature* 324:163-166 (1986). Oligonucleotides with one or more base pair mismatches are generated for any particular allele. ASO screening methods detect mismatches between variant target genomic or PCR amplified DNA and non-mutant oligonucleotides, showing decreased binding of the oligonucleotide relative to a mutant oligonucleotide. Oligonucleotide probes can be designed so that under low stringency, they will bind to both polymorphic forms of the allele, but at high stringency, bind to the allele to which they correspond. Alternatively, stringency conditions can be devised in which an essentially binary response is obtained, i.e., an ASO corresponding to a variant form of the target gene will hybridize to that allele, and not to the wild-type allele.

Ligase Mediated Allele Detection Method

Target regions of a test subject's DNA can be compared with target regions in unaffected and affected family members by ligase-mediated allele detection. See Landegren et al., *Science* 241:107-1080 (1988). Ligase may also be used to detect point mutations in the ligation amplification reaction described in Wu et al., *Genomics* 4:560-569 (1989). The ligation amplification reaction (LAR) utilizes amplification of specific DNA sequence using sequential rounds of template dependent ligation as described in Wu, supra, and Barany, *Proc. Nat. Acad. Sci.* 88:189-193 (1990).

Denaturing Gradient Gel Electrophoresis

Amplification products generated using the polymerase chain reaction can be analyzed by the use of denaturing gradient gel electrophoresis. Different alleles can be identified based on the different sequence-dependent melting properties and electrophoretic migration of DNA in solution. DNA molecules melt in segments, termed melting domains, under conditions of increased temperature or denaturation. Each melting domain melts cooperatively at a distinct, base-specific melting temperature ($T_m$). Melting domains are at least 20 base pairs in length, and may be up to several hundred base pairs in length.

Differentiation between alleles based on sequence specific melting domain differences can be assessed using polyacrylamide gel electrophoresis, as described in Chapter 7 of Erlich, ed., *PCR Technology*, "Principles and Applications for DNA Amplification", W.H. Freeman and Co., New York (1992), the contents of which are hereby incorporated by reference.

Generally, a target region to be analyzed by denaturing gradient gel electrophoresis is amplified using PCR primers flanking the target region. The amplified PCR product is applied to a polyacrylamide gel with a linear denaturing gradient as described in Myers et al., *Meth. Enzymol.* 155:501-527 (1986), and Myers et al., in *Genomic Analysis, A Practical Approach*, K. Davies Ed. IRL Press Limited, Oxford, pp. 95-139 (1988), the contents of which are hereby incorporated by reference. The electrophoresis system is maintained at a temperature slightly below the Tm of the melting domains of the target sequences.

In an alternative method of denaturing gradient gel electrophoresis, the target sequences may be initially attached to a stretch of GC nucleotides, termed a GC clamp, as described in Chapter 7 of Erlich, supra. Preferably, at least 80% of the nucleotides in the GC clamp are either guanine or cytosine.

Preferably, the GC clamp is at least 30 bases long. This method is particularly suited to target sequences with high $T_m$'s.

Generally, the target region is amplified by the polymerase chain reaction as described above. One of the oligonucleotide PCR primers carries at its 5' end, the GC clamp region, at least 30 bases of the GC rich sequence, which is incorporated into the 5' end of the target region during amplification. The resulting amplified target region is run on an electrophoresis gel under denaturing gradient conditions as described above. DNA fragments differing by a single base change will migrate through the gel to different positions, which may be visualized by ethidium bromide staining.

Temperature Gradient Gel Electrophoresis

Temperature gradient gel electrophoresis (TGGE) is based on the same underlying principles as denaturing gradient gel electrophoresis, except the denaturing gradient is produced by differences in temperature instead of differences in the concentration of a chemical denaturant. Standard TGGE utilizes an electrophoresis apparatus with a temperature gradient running along the electrophoresis path. As samples migrate through a gel with a uniform concentration of a chemical denaturant, they encounter increasing temperatures. An alternative method of TGGE, temporal temperature gradient gel electrophoresis (TTGE or tGGE) uses a steadily increasing temperature of the entire electrophoresis gel to achieve the same result. As the samples migrate through the gel the temperature of the entire gel increases, leading the samples to encounter increasing temperature as they migrate through the gel. Preparation of samples, including PCR amplification with incorporation of a GC clamp, and visualization of products are the same as for denaturing gradient gel electrophoresis.

Single-Strand Conformation Polymorphism Analysis

Target sequences or alleles at the VGT1 loci can be differentiated using single-strand conformation polymorphism analysis, which identifies base differences by alteration in electrophoretic migration of single-stranded PCR products, as described in Orita et al., *Proc. Nat. Acad. Sci.* 85:2766-2770 (1989). Amplified PCR products can be generated as described above, and heated or otherwise denatured, to form single-stranded amplification products. Single-stranded nucleic acids may refold or form secondary structures which are partially dependent on the base sequence. Thus, electrophoretic mobility of single-stranded amplification products can detect base-sequence difference between alleles or target sequences.

Chemical or Enzymatic Cleavage of Mismatches

Differences between target sequences can also be detected by differential chemical cleavage of mismatched base pairs, as described in Grompe et al., *Am. J. Hum. Genet.* 48:212-222 (1991). In another method, differences between target sequences can be detected by enzymatic cleavage of mismatched base pairs, as described in Nelson et al., *Nature Genetics* 4:11-18 (1993). Briefly, genetic material from a plant and an affected family member may be used to generate mismatch free heterohybrid DNA duplexes. As used herein, "heterohybrid" means a DNA duplex strand comprising one strand of DNA from one plant, and a second DNA strand from another plant, usually a plant differing in the phenotype for the trait of interest. Positive selection for heterohybrids free of mismatches allows determination of small insertions, deletions or other polymorphisms that may be associated with VGT1 polymorphisms.

Non-Gel Systems

Other possible techniques include non-gel systems such as TAQMAN™ (Perkin Elmer). In this system, oligonucleotide PCR primers are designed that flank the mutation in question and allow PCR amplification of the region. A third oligonucleotide probe is then designed to hybridize to the region containing the base subject to change between different alleles of the gene. This probe is labeled with fluorescent dyes at both the 5' and 3' ends. These dyes are chosen such that while in this proximity to each other the fluorescence of one of them is quenched by the other and cannot be detected. Extension by Taq DNA polymerase from the PCR primer positioned 5' on the template relative to the probe leads to the cleavage of the dye attached to the 5' end of the annealed probe through the 5' nuclease activity of the Taq DNA polymerase. This removes the quenching effect allowing detection of the fluorescence from the dye at the 3' end of the probe. The discrimination between different DNA sequences arises through the fact that if the hybridization of the probe to the template molecule is not complete, i.e., there is a mismatch of some form, the cleavage of the dye does not take place. Thus, only if the nucleotide sequence of the oligonucleotide probe is completely complimentary to the template molecule to which it is bound will quenching be removed. A reaction mix can contain two different probe sequences each designed against different alleles that might be present thus allowing the detection of both alleles in one reaction.

Yet another technique includes an Invader Assay, which includes isothermic amplification that relies on a catalytic release of fluorescence. See Third Wave Technology at world wide web at twt.com.

Non-PCR Based DNA Screening

Hybridization probes are generally oligonucleotides which bind through complementary base pairing to all or part of a target nucleic acid. Probes typically bind target sequences lacking complete complementarity with the probe sequence depending on the stringency of the hybridization conditions. The probes are preferably labeled directly or indirectly, such that by assaying for the presence or absence of the probe, one can detect the presence or absence of the target sequence. Direct labeling methods include radioisotope labeling, such as with $P^{32}$ or $S^{35}$. Indirect labeling methods include fluorescent tags, biotin complexes which may be bound to avidin or streptavidin, or peptide or protein tags. Visual detection methods include photoluminescents, Texas red, rhodamine and its derivatives, red leuco dye and 3,3',5,5'-tetramethylbenzidine (TMB), fluorescein, and its derivatives, dansyl, umbelliferone and the like or with horse radish peroxidase, alkaline phosphatase and the like.

Hybridization probes include any nucleotide sequence capable of hybridizing to the chromosome where VGT1 resides, and thus defining a genetic marker linked to VGT1, including a restriction fragment length polymorphism, a hypervariable region, repetitive element, or a variable number tandem repeat. Further suitable hybridization probes include exon fragments or portions of cDNAs or genes known to map to the relevant region of the chromosome.

Preferred tandem repeat hybridization probes for use according to the present invention are those that recognize a small number of fragments at a specific locus at high stringency hybridization conditions, or that recognize a larger number of fragments at that locus when the stringency conditions are lowered.

One or more additional restriction enzymes and/or probes and/or primers can be used. Additional enzymes, constructed probes, and primers can be determined by routine experimentation by those of ordinary skill in the art and are intended to be within the scope of the invention.

Although the methods described herein may be in terms of the use of a single restriction enzyme and a single set of primers, the methods are not so limited. One or more additional restriction enzymes and/or probes and/or primers can be used, if desired. Indeed, in some situations it may be preferable to use combinations of markers giving specific haplotypes. Additional enzymes, constructed probes and primers can be determined through routine experimentation, combined with the teachings provided and incorporated herein.

The sequences surrounding the polymorphism will facilitate the development of alternate PCR tests in which a primer of about 4-30 contiguous bases taken from the sequence immediately adjacent to the polymorphism is used in connection with a polymerase chain reaction to greatly amplify the region before treatment with the desired restriction enzyme. The primers need not be the exact complement; substantially equivalent sequences are acceptable. The design of primers for amplification by PCR is known to those of skill in the art and is discussed in detail in Ausubel (ed.), *Short Protocols in Molecular Biology*, 4th Edition, John Wiley and Sons (1999).

The following is a brief description of primer design.

Primer Design Strategy

Increased use of polymerase chain reaction (PCR) methods has stimulated the development of many programs to aid in the design or selection of oligonucleotides used as primers for PCR. Four examples of such programs that are freely available via the Internet are: PRIMER by Mark Daly and Steve Lincoln of the Whitehead Institute (UNIX, VMS, DOS, and Macintosh), Oligonucleotide Selection Program (OSP) by Phil Green and LaDeana Hiller of Washington University in St. Louis (UNIX, VMS, DOS, and Macintosh), PGEN by Yoshi (DOS only), and Amplify by Bill Engels of the University of Wisconsin (Macintosh only). Generally these programs help in the design of PCR primers by searching for bits of known repeated-sequence elements and then optimizing the $T_m$ by analyzing the length and GC content of a putative primer. Commercial software is also available and primer selection procedures are rapidly being included in most general sequence analysis packages.

Sequencing and PCR Primers

Designing oligonucleotides for use as either sequencing or PCR primers requires selection of an appropriate sequence that specifically recognizes the target, and then testing the sequence to eliminate the possibility that the oligonucleotide will have a stable secondary structure. Inverted repeats in the sequence can be identified using a repeat-identification or RNA-folding program such as those described above. If a possible stem structure is observed, the sequence of the primer can be shifted a few nucleotides in either direction to minimize the predicted secondary structure. The sequence of the oligonucleotide should also be compared with the sequences of both strands of the appropriate vector and insert DNA. Obviously, a sequencing primer should only have a single match to the target DNA. It is also advisable to exclude primers that have only a single mismatch with an undesired target DNA sequence. For PCR primers used to amplify genomic DNA, the primer sequence should be compared to the sequences in the GenBank database to determine if any significant matches occur. If the oligonucleotide sequence is present in any known DNA sequence or, more importantly, in any known repetitive elements, the primer sequence should be changed.

The following examples serve to better illustrate the invention and are not intended to limit the scope of the invention in any way. All references and patents disclosed herein are specifically incorporated herein in their entirety by reference.

Salvi S., Morgante M., Fengler K., Meeley R., Ananiev E., Svitashev S., Bruggemann E., Niu X., Li B., Tingey SV., Tomes D., Miao G.-H., Phillips R L., Tuberosa R. Progress in the positional cloning of Vgt1, a QTL controlling flowering time in maize (2003). Proceedings of $57^{th}$ Corn and *Sorghum* and $32^{nd}$ Soybean Seed Research Conference. Dec. 11-13, 2002, Chicago.

Phillips R. L., Kim T. S., Kaeppler S. M., Parentoni S, N., Shaver D. L., Stucker R. I. and Openshaw S. J. 1992. Genetic dissection of maturity using RFLPs. Proc. $47^{th}$ Ann. Corn and *Sorghum* Res. Conf. 47:135-150.

Vladutu, C., McLaughlin J. and Phillips R. L. 1999. Fine Mapping and Characterization of Linked Quantitative Trait Loci Involved in the Transition of the Maize Apical Meristem From Vegetative to Generative Structures. Genetics 153: 993-1007.

Salvi S., Tuberosa R., Chiapparino E., Maccaferri M., Veillet S., van Beuningen L., Isaac P., Edward K. J., Phillips R. L. (2002). Toward positional cloning of Vgt1, a QTL controlling the transition from the vegetative to the reproductive phase in maize. Plant Mol Biol 48:601-613.

EXAMPLES

Example 1

RAP2.7 Expression Level is Associated with Differences in Maturity

It was determined that RAP2.7 gene expression level determines the transition to flowering in plants and that vgt1 is a cis-element that regulates RAP2.7 transcription. Two plants with different maturities (N28 and C22-4) were then screened to identify if the RAP2.7 expression levels differ between them.

RNA was synthesized from N28 and C22-4 from different tissues and stages of development, and RAP2.7 expression was measured by RT-PCR.

Tissue Types:
  Mature leaves—exposed, blades+sheaths
  Immature leaves—in whorl, blades+sheaths
  Shoot apical meristems
  Roots—whole, including root apical meristems
  Stalks—leftovers Developmental Stages

|  | Sample Number | | | | |
| --- | --- | --- | --- | --- | --- |
| Genotype | 1 | 2 | 3 | 4 | 5 |
| N28 (late) | veg | veg | veg | trans | rep |
| C22-4 (early) | veg | trans | rep | rep | rep |

Gene Expression Assay

First total RNA was prepared from frozen tissue samples. cDNA was then made by reverse transcriptase and the PAR2.7 region was amplified using PCR with agarose gel and ethidium bromide staining. Band fluorescence was quantified and tubulin was used as an internal control, and to normalize expression levels.

FIG. 1 shows the levels of RAP2.7 expression at Day: 14 before transition, C22-4 on transition at 20 days, and N28 at transition at 27 days. Last two dates have 3 samples of each. P values are significantly different at the first two sampling dates, but not at the latest date. There is RAP2.7 signal from meristems, and other tissues. RAP2.7 is a repressor of flowering, and must be below a particular level for flowering to occur.

The results indicate that RAP2.7 is expressed in every tissue type. RAP2.7 expression levels are lower in C22-4 than in N28 before the reproductive transition (mature leaves), and RAP2.7 expression levels decrease during development in both C22-4 and N28. Thus, overexpression of RAP2.7 will delay transition from vegetative state to flowering.

Example 2

Over-Expression of Maize RAP2.7 Under a Moderate-Strength Constitutive Promoter

The cDNA sequences of RAP2.7 were obtained from a RT-PCR experiment. Specifically, total RNA from C22-4 leaves was isolated and used as template in RT-PCR with gene-specific primers. The gene-specific primers were designed based on RAP2.7 genomic sequences from B73 genotype. The primer sequences are sense—ATGCAGTTG-GATCTGAACGT (SEQ ID NO: 9) and antisense—GCCAT-CACCATCCCCGCTGA (SEQ ID NO:10).

Figure 2:
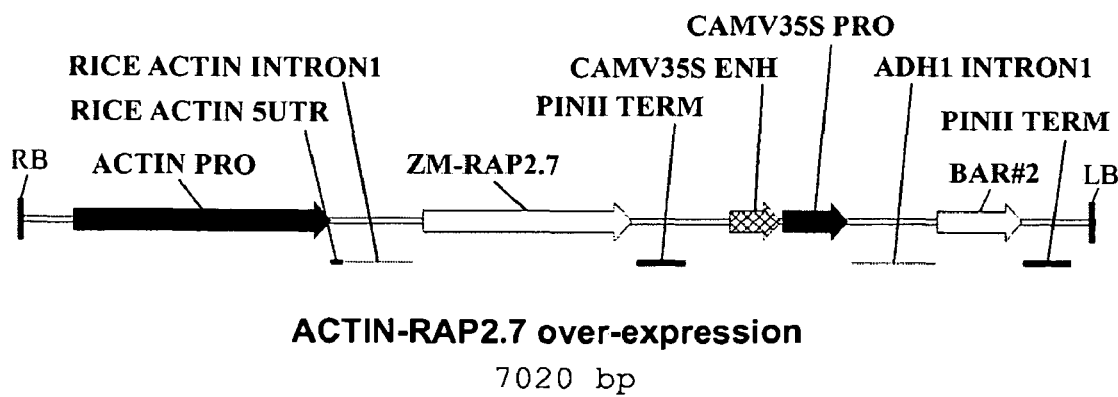
FIG. 2 is an illustration of the over-expression vector used in transformation, showing the portion between the right and left T-DNA borders (RB, LB). The transformation vector for RAP2.7 over-expression, PHP20922, was created by electroporating the JT vector PHP20921 into Agrobacterium. The Invitrogen (Carlsbad, Calif.) Gateway technology was used to create PHP20921. Specifically, the RAP2.7 coding region was first amplified by PCR with 5'-primer SEQ ID NO: 9 (ggggacaagtttgtacaaaaaagcaggctatgcagttggatctgaacgt) and 3' primer SEQ ID NO: 10 (ggggaccactttgtacaa-gaaagctgggttcagcggggatggtgatg). These primers contain Gateway attB recombination sites. The PCR product was confirmed by sequencing and cloned into a 25 Gateway vector pDONR221 via a BP recombination reaction as described by the vendor (Invitrogen, Carlsbad, Calif.). This resulted in the entry clone, PHP20923. Two other entry clones, PHP20830 containing the rice actin promoter, PHP20234 containing the pinII terminator, have been previously created using similar cloning strategies. A destination vector PHP20909 was also created from pDESTR4-R3 vector (Invitrogen, Carlsbad, Calif.) by inserting an expression cassette of the CaMV35S promoter driving the herbicide resistance gene Bar followed by a pinII terminator. The four vectors, PHP20923, 20830, 20234 and 20909, were then used to create the JT vector, PHP20921, via a LR recombination reaction following vendor's instructions (Invitrogen, Carlsbad, Calif.).

The RT-PCR amplified fragment of RAP2.7, including the entire 1371-bp sequence including the ATG start codon and the TAG stop codon, was fused to the rice actin promoter and pinII terminator to produce an expression cassette. This expression cassette was then linked to a selectable marker cassette containing a bar gene driven by CaMV 35S promoter and a pinII terminator in FIG. 2.

Transgenic maize plants were produced by transforming Immature GS3 maize embryos with this expression cassette, using the *Agrobacterium*-based transformation method described as below.

For *Agrobacterium*-mediated transformation of maize with the expression cassette comprising the rice actin promoter operably linked to the maize RAP2.7 gene, the method of Zhao was employed (U.S. Pat. No. 5,981,840, and PCT patent publication WO98/32326; the contents of which are hereby incorporated by reference). While the method below is described for the transformation of maize plants with the actin promoter—RAP2.7 expression cassette, those of ordinary skill in the art recognize that this method can be used to produce transformed maize plants with any nucleotide construct or expression cassette of the invention that comprises a promoter operably linked to maize RAP2.7 gene for expression in a plant.

Briefly, immature embryos were isolated from maize and the embryos contacted with a suspension of *Agrobacterium*, where the bacteria are capable of transferring the ACTIN promoter-RAP2.7 expression cassette (illustrated above) to at least one cell of at least one of the immature embryos (step 1: the infection step). In this step the immature embryos were immersed in an *Agrobacterium* suspension for the initiation of inoculation. The embryos were co-cultured for a time with the *Agrobacterium* (step 2: the co-cultivation step). The immature embryos were cultured on solid medium following the infection step. Following this co-cultivation period an optional "resting" step was included. In this resting step, the embryos were incubated in the presence of at least one antibiotic known to inhibit the growth of *Agrobacterium* without the addition of a selective agent for plant transformants (step 3: resting step). The immature embryos were cultured on solid medium with antibiotic, but without a selecting agent, for elimination of *Agrobacterium* and for a resting phase for the infected cells. Next, inoculated embryos were cultured on medium containing a selective agent and growing transformed callus was recovered (step 4: the selection step). Preferably, the immature embryos were cultured on solid medium with a selective agent resulting in the selective growth of transformed cells. The resulting calli were then regenerated into plants by culturing the calli on solid, selective medium (step 5: the regeneration step).

The transformation produced 15 events in GS3XGaspe flint, an early-flowering genotype. Transformation in GS3XHC69, a normal maturity genotype, was problematic during shoot regeneration process and only produced 5 events. The problem was presumed to be related to the transgene. Two of the 5 events had delays in flowering time for up to 30 days. In GS3XGaspe flint genotype, majority (16 out of 20) of the events had various degrees of delay in flowering time, from 16 days to 36 days. In almost all events with delayed flowering, there was significant change in plant architecture, mostly increase in plant height and internode length.

Ectopic expression of Rap2.7 with the rice actin promoter resulted in over expression of the gene, and significantly delayed flowering as measured by the number of leaves (nodes) produced prior to flowering. According to the invention, vectors for transformation were produced in two corn genetic backgrounds (GS3 X HC69, and GS3 X GF, gaspe flint) using the Rap2.7 structural gene with the rice actin promoter.

A brief summary of the T0 phenotype from over-expressing RAP2.7 in maize is shown in the following tables. As a reference, GS3XGaspe plants coming out of tissue culture get pollinated (exuding silks) within 45-60 days, and have 10 or less leaves. Since these are T0 plants, accurate counts for leaf number and days to flowering are not possible. The plants that were late in flowering also had substantial increase in internode elongation, resulting in increase in plant height. These plants also had delayed senescence.

| Events | GS3XHC69 | GS3XGaspe |
| --- | --- | --- |
| Late | 2 | 16 |
| Total | 5 | 20 |

| | GS3XGaspe Events |
| --- | --- |
| Days to Pollination | |
| <60 days | 4 |
| 61-70 days | 5 |
| 71-80 days | 7 |
| >81 days | 1 |
| no ear | 3 |
| Leaf Number (estimated) | |
| <10 | 4 |
| 10-12 | 10 |
| 13-14 | 4 |
| >15 | 2 |

Example 3

Down-Regulation of Maize Rap2.7 by RNA Interference

Two fragments from the cDNA sequences of RAP2.7 from genotype C22-4 were cloned by PCR to create an inverted repeat as illustrated below. Specifically, a 955-bp fragment starting at 9-bp downstream from ATG was cloned by PCR and designated as ZM-RAP2.7 (TR1) as a truncated form. Another fragment, 499-bp in length starting from the same position, was cloned and designated as ZM-RAP2.7 (IR1) for inverted repeat FIG. 5.

Figure 5:
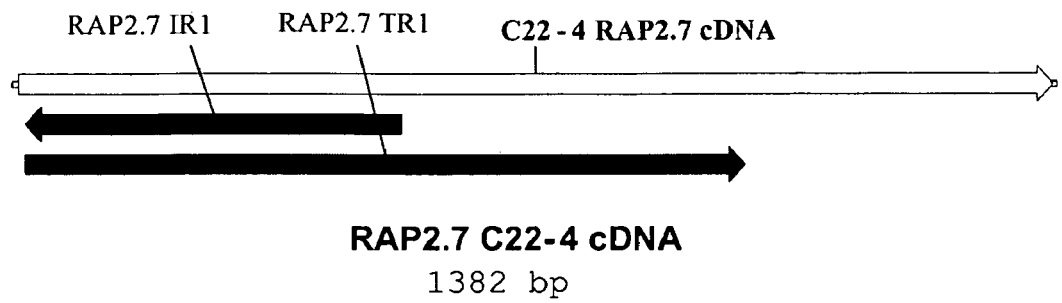
FIG. 5 is an illustration of construction of the RAP2.7 gene fragments for the RNA interference vector. Fragment TR1 (Truncated1) was created by PCR using forward (SEQ ID NO: 11) (ggatccgatctgaacgtggccgag) and reverse primers (SEQ ID NO: 12) (gaattcctaggcagctgttcttgtctctttg) 15 corresponding to roughly ⅔ of the coding sequence starting from 9 bp downstream of ATG. Fragment IR1 (Inverted1) was generated similarly by PCR with forward (SEQ ID NO: 13) (gcggccgcgatctgaacgtggccgag) and reverse primers (SEQ ID NO: 14) (gaattctgtgggactcccagcggcctgtgc) starting from the same position as TR1, although IR1 is only half the length of TR1.

FIG. 5 Illustration of construction of the RAP2.7 gene fragments for RNA interference vector. TR1 fragment was then ligated to IR1, with IR1 in reverse orientation. The ligated 2-piece fragment was then linked to rice actin promoter with actin 5'-UTR and actin intron1 to create a full expression cassette. This expression cassette was then linked to a selectable marker cassette containing a bar gene driven by CaMV 35S promoter and a pinII terminator.

Figure 6:
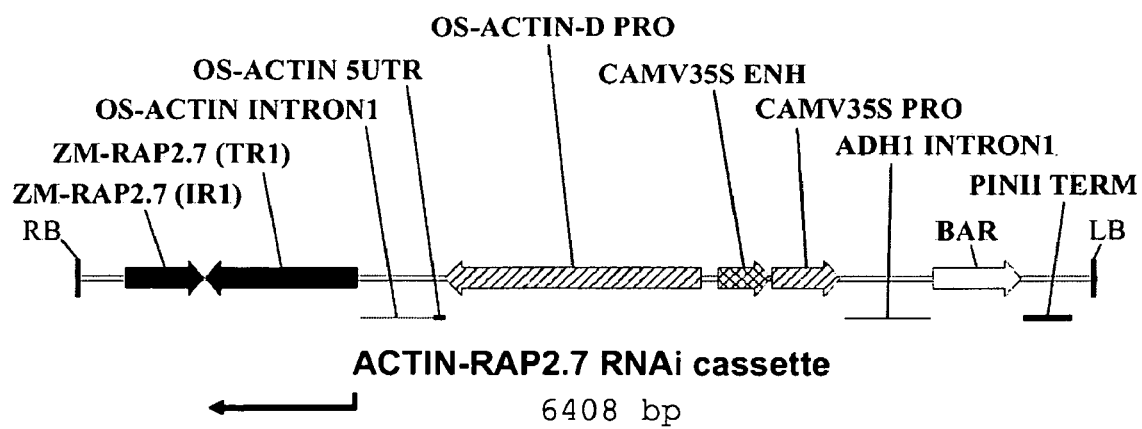
FIG. 6 is an illustration of the vector used in transformation showing only the portion between the right and left T-DNA borders (RB, LB). As described in FIG. 5, fragments corresponding to truncated coding regions to be used for the RNA interference construct were generated by as TR1, flanked by BamH1 and EcoR1, and IR1, flanked by NotI and EcoR1 restriction sites. Vector PHP16501 containing the rice actin promoter was linearized with NotI and BamH1. In a 3-piece ligation, TR1 was cloned in downstream of NotI followed by IR1 in reverse orientation. The resulting cassette vector, PHP21767, was then cloned into a JT vector containing the CaMV35S promoter driving the herbicide resistance gene Bar. The transformation vector for RAP2.7 down regulation, PHP21842, was generated by electroporating PHP21798 into *Agrobacterium*.

FIG. 6 is an illustration of the vector used in transformation. Note only the portion between the right and left T-DNA borders (RB, LB) is shown. Transgenic maize plants were produced by transforming Immature GS3 maize embryos with this expression cassette, using the *Agrobacterium*-based transformation method described for the RAP2.7 over-expression study. The transformation produced 20 transgenic events from GS3XHC69, a genotype with a normal maturity; and 15 events from GS3XGaspe flint, an early-flowering genotype. Based on preliminary observation on T0 plants, all 15 events from the GS3XGaspe flint background showed no visible change in flowering time. However, 9 out of the 20 GS3XHC69 transgenic events had various degrees of early flowering phenotype. The earliest event flowered approximately 2 week earlier compared to other events with the same construct, and to other unrelated transgenic plants in the same greenhouse room. All plants had normal plant architecture.

The T0 data shows that if you down regulate RAP2.7 earlier flowering is observed. The following table shows the next (T1) generation of plants. We can see from this data that the phenotype is heritable and stable and the initial trend of decreased days to pollination is still observed.

| PHP21842 T1 Phenotype | | | |
|---|---|---|---|
| Event-Plant | Transgene | Leaf # | Days to Pollination |
| 1-1 | + | 15 | 58 |
| 1-2 | + | 13 | 55 |
| 1-3 | + | 15 | 57 |
| 2-1 | + | 14 | 57 |
| 2-2 | + | 14 | 54 |
| 2-3 | + | 13 | 53 |
| 3-1 | + | 14 | 57 |
| 3-2 | + | 13 | 57 |
| 3-3 | + | 14 | 59 |
| Control average (n = 20) | + | 19.2 | 66 |

Example 4

Positional Cloning of Vgt1

Figure 7:
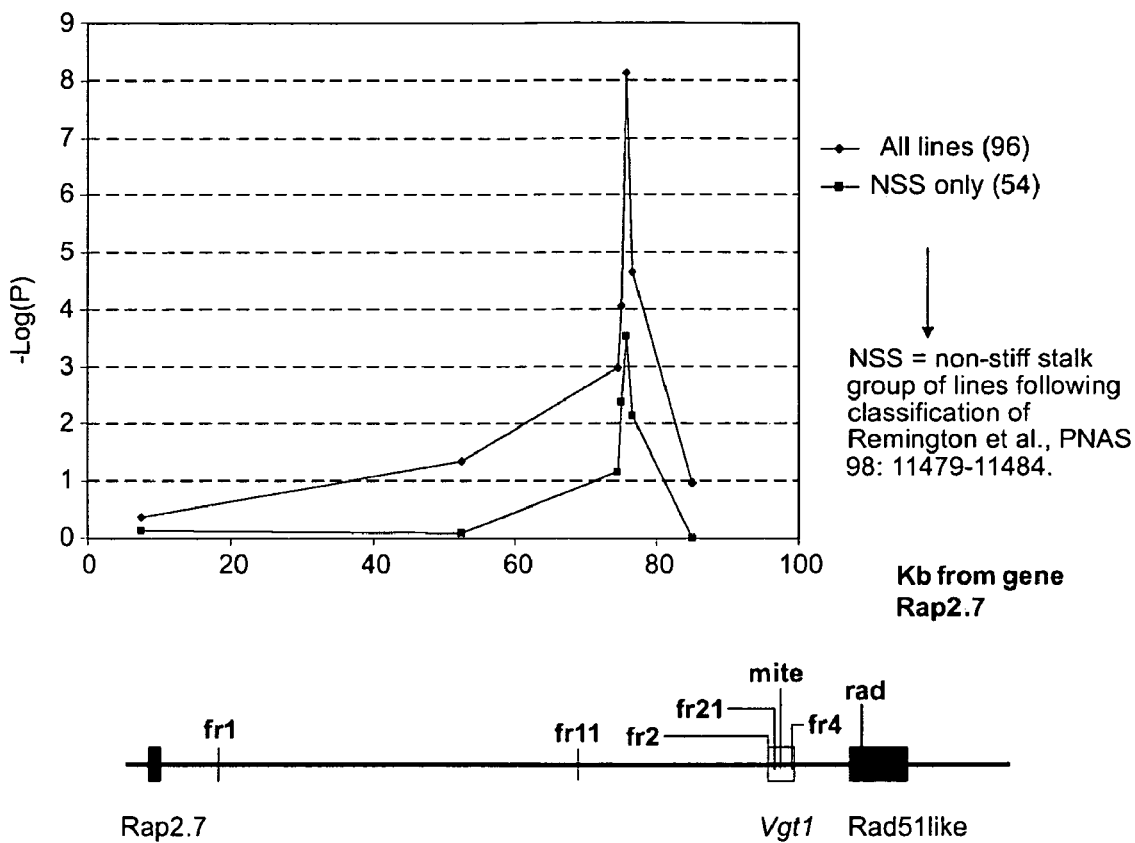
FIG. 7 is the data showing the fine genetic and physical mapping of VGT1. First row indicates physical distance (in kb) from Rap2.7, based on sequence derived from the relevant Mo17 BAC clone from library. Second row indicates the type of molecular marker. Third row indicates the name of the molecular markers. Rows from 4 to 21 indicate the genotype of parental lines (N28 and C22-4) and of the 17 segmental QTL-Nearly Isogenic Lines. The VGT1 column shows where the QTL was mapped. The last two columns provide the phenotypic scores for DPS (Days to Pollen Shed) and ND (plant node number).

Positional cloning was completed after mapping Vgt1 in a 1.3-cM interval flanked by two AFLP markers (Salvi et al., 2002), in a cross between two nearly isogenic lines, N28 and its early derivative C22-4 (Vladutu et al., 1999). Following BAC library screening and the analysis of the relevant BAC contig, further development of new markers and genetic mapping allowed for the delimiting of Vgt1 within a ca. 2.7-kb region (FIG. 7.)

Sequencing of the relevant BAC clone and of the corresponding DNA region from the parental lines involved in the cross showed that Vgt1 lies within an intergenic region, ca. 75 kb upstream of an Ap-2 like gene (Rap2.7) and ca. 10 kb downstream of a RAD51-like gene. The 2.7 kb region found to be completely associated with Vgt1 is essentially a low-copy region with a number of polymorphisms between N28 and C22-4 (one of the polymorphisms is caused by the insertion of a MITE transposable element in C22-4). Surprisingly, this sequence does not code for any known protein. It is hypothesized to either be a RNAi element or a regulatory RNA or DNA element that either directly regulates expression of flowering genes such as Rap2.7 or specifically targets expression of other genes which control flowering genes such as Rap2.7.

Example 5

Vgt1 is Associated with Maturity Shift in Inbred Lines

The information gathered with the positional cloning study allowed the testing of the 2.7 kb region as candidate for controlling flowering time through association mapping. Several SNPs and other polymorphisms identified at and around Vgt1 were screened on a panel of ca. 100 lines representative of cultivated maize germplasm (Remington et al., 2001) and a panel of elite proprietary lines.

Linkage disequilibrium at the Vgt1 region was quickly dissipated over distance of ca. 1 kb within the panel of 100 lines. Association analysis showed that among the genes and sequence at and around Vgt1, the only DNA region statistically associated with flowering time was a sub-region of ca. 2 kb within the same 2.7 kb region identified by positional cloning (FIG. 8.).

This element thus can be used as a sequence-based marker to identify inbred and hybrids which have altered maturity.

What is claimed is:

1. A method for altering flowering time in a plant comprising: transforming a plant cell with a nucleic acid molecule operably linked to a promoter that regulates transcription of said molecule in a plant cell and regenerating a plant from said plant cell; wherein said nucleic acid molecule comprises a nucleotide sequence selected from the group consisting of:
  (a) a nucleotide sequence comprising the sequence set forth in SEQ ID NO: 1
  (b) a nucleotide sequence encoding the amino acid sequence of SEQ ID NO: 2;
  (c) a nucleotide sequence having at least 98% sequence identity to the sequence of SEQ ID NOS: 1, wherein said nucleotide sequence encodes a protein which regulates flowering in plants, wherein said nucleic acid molecule is in a vector for inhibiting expression of RAP2.7.

2. The method of claim 1 wherein said vector is an RNA interference vector.

3. The method of claim 2 wherein said plant flowers earlier than a plant which does not have an RNA interference vector incorporated therein.

4. A method for altering maturity of a plant, said method comprising:
  transforming a plant with a nucleic acid molecule comprising a heterologous sequence operably linked to a promoter that induces transcription of said heterologous sequence in a plant cell; and regenerating stably transformed plants from said plant cell, wherein said heterologous sequence comprises a nucleotide sequence selected from the group consisting of:
  (a) a nucleotide sequence comprising the sequence set forth in SEQ ID NOS: 1; and
  (b) a nucleotide sequence having at least 98% sequence identity to the sequence of SEQ ID NO: 1, wherein said nucleotide sequence encodes a protein which regulates flowering in plants; wherein said nucleic acid molecule is in a vector for inhibiting expression of RAP2.7.

5. The method of claim 4 wherein said vector is an RNA interference vector.

6. The method of claim 5 wherein said plant matures earlier than a plant which does not have an RNA interference vector incorporated therein.

* * * * *